United States Patent [19]

Kumazawa et al.

[11] Patent Number: 5,239,083
[45] Date of Patent: Aug. 24, 1993

[54] INDOLE DERIVATIVES WHICH INHIBIT STEROID 5α REDUCTASE

[75] Inventors: Toshiaki Kumazawa; Hitoshi Takami; Hiroyuki Obase; Nobuyuki Kishibayashi; Akio Ishii, all of Shizuoka, Japan

[73] Assignee: Kyowa Hakko Kogyo Co., Ltd., Tokyo, Japan

[21] Appl. No.: 850,334

[22] Filed: Mar. 10, 1992

[30] Foreign Application Priority Data

Mar. 11, 1991 [JP] Japan .................................. 3-044941

[51] Int. Cl.$^5$ .................. C07D 209/04; C07D 211/68; C07D 257/04; C07D 413/12
[52] U.S. Cl. ...................................... 548/465; 546/273; 548/491; 548/494; 548/495; 548/496
[58] Field of Search ................. 546/273; 548/465, 496, 548/491, 494, 495; 514/339, 414, 419, 381

[56] References Cited

U.S. PATENT DOCUMENTS

| | | | |
|---|---|---|---|
| 3,109,844 | 11/1963 | Perron et al. | 548/494 X |
| 3,569,011 | 2/1971 | Yamamoto et al. | 548/491 X |
| 4,239,902 | 12/1980 | Schnabel | 548/496 X |

(List continued on next page.)

*Primary Examiner*—Floyd D. Higel
*Attorney, Agent, or Firm*—Pennie & Edmonds

[57] ABSTRACT

The present invention provides Indole derivatives represented by the formula (I)

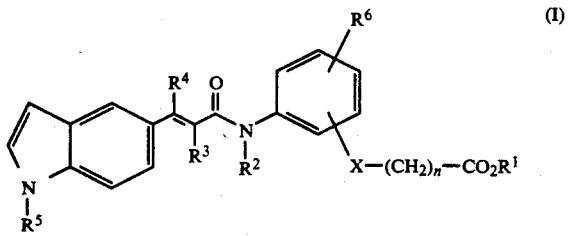

wherein $R^1$, $R^2$ and $R^3$ independently represent hydrogen or lower alkyl;

$R^4$ represents hydrogen, lower alkyl or cycloalkyl;
$R^5$ represents hydrogen, substituted or unsubstituted cycloalkyl, substituted or unsubstituted cycloalkenyl, —$CHR^7R^8$ where $R^7$ and $R^8$ independently represent hydrogen, alkyl, alkenyl, alkynyl, substituted or unsubstituted cycloalkyl, —$(CH_2)_mOR^9$ (wherein m is an integer of 1-3 and $R^9$ is lower alkyl), substituted or unsubstituted aryl, substituted or unsubstituted pyridyl, substituted or unsubstituted furyl, or substituted or unsubstituted thienyl],

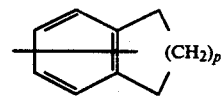

(wherein p is an integer of 1-3) or

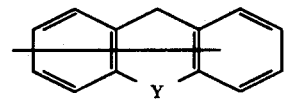

(wherein Y is $CH_2$, O, S, $CH_2$—$CH_2$, CH=CH, $CH_2$—O or $CH_2$—S); $R^6$ represents hydrogen, lower alkyl or lower alkoxy or halogen;
X represents O or $S(O)q$ (wherein q is an integer of 0-2); and n represents an integer of 1-6) or pharmaceutically acceptable salt thereof.

The compound shows prominent inhibition effects on steroid 5α-reductase activity, and are useful in treating benign prostatic hypertrophy, prostate cancer, baldness and acne.

9 Claims, No Drawings

U.S. PATENT DOCUMENTS

| | | | |
|---|---|---|---|
| 4,814,463 | 3/1989 | Kim, I | 548/495 |
| 4,859,692 | 8/1989 | Bernstein et al. | 548/491 X |
| 4,902,708 | 2/1990 | Kim, II | 514/419 |
| 5,041,460 | 8/1991 | Matassa | 514/414 X |
| 5,049,679 | 9/1991 | Bernstein | 548/491 |
| 5,084,455 | 1/1992 | Clemence et al. | 514/247 |
| 5,087,701 | 2/1992 | Lubowitz et al. | 548/465 |
| 5,118,700 | 6/1992 | Butler et al. | 548/494 X |

FOREIGN PATENT DOCUMENTS

| | | | |
|---|---|---|---|
| 173516 | 3/1986 | European Pat. Off. | 548/491 |
| 294035 | 12/1988 | European Pat. Off. | 548/491 |
| 294937 | 12/1988 | European Pat. Off. | 548/491 |

OTHER PUBLICATIONS

European Search Report of EP 92104088.7, Dated 14 Sep. 1992.

Patent Abstracts of Japan, vol. 12, No. 50 (C–476) [2897], Feb. 16, 1988, Abstract of Japanese Patent Document 62-198653.

Goodman and Gilman's, The Pharmacological Basis of Therapeutics, Eighth Edition, pp. 1427–1430, 1987.

Cecil, Textbook of Medicine, Wyngaarden, J. B., et al., pp. 1400–1401, 1422–1425 (1988).

The Testis, Scientific America, Inc., Section II, pp. 1–2, 8–9 and 12–15 (1991).

Encyclopedia of Human Biology, 4:243–244, 1987.

The Merck Index, Eleventh Edition, p. 4869 (Indole) (1989). I.

The Merck Index, Eleventh Edition, p. 7888 (Proscar) (1989). II.

Petrow, The Prostate, 9:344–361 (1986), "The Dihydrotestosterone (DHT) Hypothesis of Prostate Cancer and its Therapeutic Implications."

Rittmaster et al., Journal of Andrology, 10:259–262 (1989), "Effect of MK-906, a Specific 5α-reductase Inhibitor, on Serum Androgens and Androgen Conjugates in Normal Men."

Geller, I The Prostate Supplement, 2:95–104 (1989), "Pathogenesis and Medical Treatment of Benign Prostatic Hyperplasia."

Gormley et al., Journal of Clinical Endocinology and Metabolism, 70:1136–1141 (1990), "The Effects of Finasteride (MK-906), a 5α-Reductase Inhibitor, on Circulating Androgens in Male Volunteers."

Imperato-McGinley et al., Journal of Clinical Endocrinology and Metabolism, 70:777–782 (1990), "$C_{19}$ and $C_{21}$ 5β/5α Metabolic . . . ".

Geller, II, Journal ofClinical Endocrinology and Metabolism, 71:1552–1555 (1990), "Effect of Finasteride . . .".

Tenover, Endocrinol. Metab. Clin. North Amer., 20:893–909 (1991) (abstract only), "The Potential Medical Uses of Steroid 5alpha-reductase Inhibitors." Abstract only.

M. Bologna et al., Curr. Ther. Res. Clin. Exp., 51:799–813 (1992) (abstract only), "Antiandrogens and 5-alpha Reductase Inhibition of the Proliferation Rate . . . " Abstract only.

1

INDOLE DERIVATIVES WHICH INHIBIT STEROID 5α REDUCTASE

INTRODUCTION

The present invention relates to novel indole derivatives useful as therapeutic agents for benign prostatic hypertrophy (BPH), prostate cancer, baldness and acne because of the inhibitory effects of the indole derivatives on steroid 5α-reductase.

BACKGROUND OF THE INVENTION

In prostate tissues of patients with BPH, the rise of steroid 5α-reductase activity in prostate tissue causes accumulation of the large amount of dihydrotestosterone (the product of steroid 5α-reductase). Hence, it was suggested that dihydrotestosterone plays an important role in the attack of BPH and that steroid 5α-reductase inhibitor is useful for the treatment of BPH [The Prostate Supplement 2: 95 (1989)]. It has been reported that the growth of prostate cancer is dependent upon dihydrotestosterone and is independent of testosterone so that steroid 5α-reductase inhibitor is useful for the therapy of prostate cancer [The Prostate 9: 343 (1986)]. Furthermore, it has been known that dihydrotestosterone plays a key role in the attack of acne and baldness.

The compound represented by the formula (A) shown below is disclosed as a synthetic intermediate of leukotriene antagonist in European Patent No. 290145.

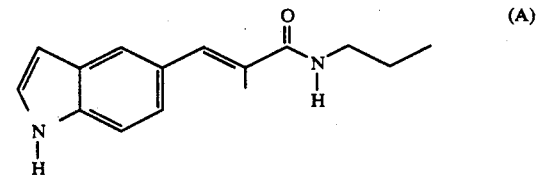

(A)

SUMMARY OF THE INVENTION

An object of the invention is to provide novel indole derivatives having inhibitory effects on steroid 5α-reductase.

The present invention relates to indole derivatives represented by the formula (I) [hereafter referred to as compound (I) and other compounds having a formula number are also termed by the same manner].

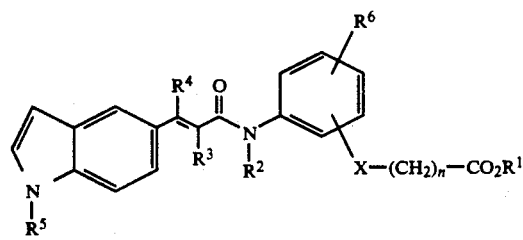

(I)

wherein $R^1$, $R^2$ and $R^3$ independently represent hydrogen or lower alkyl;
$R^4$ represents hydrogen, lower alkyl or cycloalkyl;
$R^5$ represents hydrogen, substituted or unsubstituted cycloalkyl, substituted or unsubstituted cycloalkenyl,
—$CHR^7R^8$ where $R^7$ and $R^8$ independently represent hydrogen, alkyl, alkenyl, alkynyl, substituted or unsubstituted cycloalkyl, —$(CH_2)_mOR^9$ (wherein m is an integer of 1-3 and $R^9$ is lower alkyl), substituted or unsubstituted aryl, substituted or unsubstituted pyridyl, substituted or unsubstituted furyl, or substituted or unsubstituted thienyl,

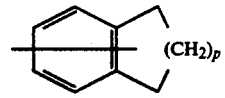

(wherein p is an integer of 1-3) or

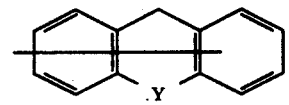

(wherein Y is $CH_2$, O, S, $CH_2$—$CH_2$, $CH$=$CH$, $CH_2$—O or $CH_2$—S); $R^6$ represents hydrogen, lower alkyl, lower alkoxy or halogen;
X represents O or $S(O)_q$ (wherein q is an integer of 0-2); and n represents an integer of 1-6 or pharmaceutically acceptable salts thereof.

DETAILED DESCRIPTION OF THE INVENTION

In the definition of the respective group in the formula (I), the lower alkyl or the alkyl moiety of the lower alkoxy means straight or branched alkyls having 1-6 carbon atoms, such as methyl, ethyl, propyl, isopropyl, butyl, isobutyl, sec-butyl, tert-butyl, pentyl, and hexyl, etc; the cycloalkyl includes compounds having 3-8 membered carbon ring, such as cyclopropyl, cyclobutyl, cyclopentyl, cyclohexyl, cycloheptyl and cyclooctyl, etc; the cycloalkenyl includes compounds having 3-8 membered carbon ring, such as cyclopropenyl, cyclobutenyl, cyclopentenyl, cyclohexenyl, cycloheptenyl, and cyclooctenyl, etc; the alkyl includes straight or branched alkyls having 1-10 carbon atoms, such as methyl, ethyl, propyl, butyl, pentyl, hexyl, heptyl, octyl, nonyl, decyl, isopropyl, sec-butyl, tert-butyl, 1-methylbutyl, 1-ethylpropyl, 1-methylpentyl, 1-ethylbutyl, 1-methylhexyl, 1-ethylpentyl, 1-methylheptyl, 1-ethylhexyl, 1,2-dimethylpropyl, 1,2-dimethylbutyl, 2-methylbutyl, 3-methylbutyl, 4-methylpentyl, 5-methylhexyl, 1-(1-methylethyl)butyl, and 1-butylpentyl, etc; the alkenyl includes straight or branched alkenyls having 2-10 carbon atoms, such as vinyl, allyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, isopentenyl, and geranyl, etc; the alkynyl includes straight or branched alkynyls having 2-10 carbon atoms, such as ethynyl and 2-propynyl, etc; the aryl includes phenyl and naphthyl, etc; the halogen includes fluorine, chlorine, bromine, and iodine.

The number of substituents in the substituted cycloalkyl and substituted cycloalkenyl is 1-2. The substituents are the same or different and are lower alkyl. Said lower alkyl is the same lower alkyl as defined above. The number of substituents in the substituted aryl, substituted pyridyl, substituted furyl and substituted thienyl is 1-3. The substituents are the same or different and are lower alkyl, hydroxy, lower alkoxy, lower alkylamino, trifluoromethyl, or halogen, etc. The alkyl moiety of the lower alkyl, the lower alkoxy and the lower alkylamino, and the halogen are the same meaning as defined above.

Pharmaceutically acceptable salt of the compound (I) include pharmaceutically acceptable acid addition salts such as inorganic acid salts (e.g., hydrochloride, sulfate, phosphate) and organic acid salts (e.g., maleate, fumarate, citrate), pharmaceutically acceptable base addition salts such as ammonium salts, and pharmaceutically acceptable metal salts such as lithium salts, sodium salts, potassium salts, calcium salts, and magnesium salts.

The compound (I) is prepared according to the following process:

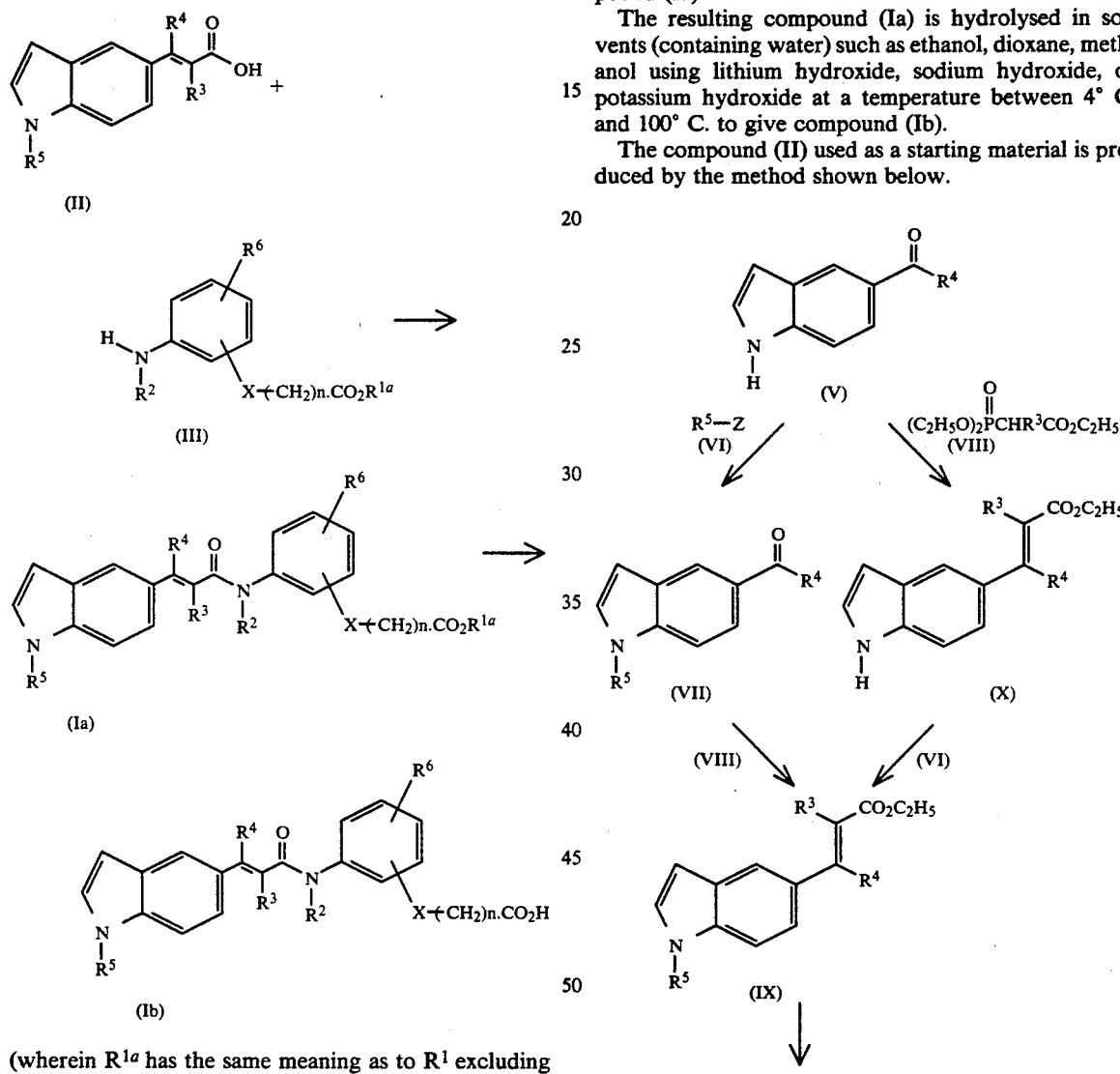

(wherein $R^{1a}$ has the same meaning as to $R^1$ excluding hydrogen and $R^2$, $R^3$, $R^4$, $R^5$, $R^6$, X and n have the same meaning as described above).

The compound (Ia) in which $R^1$ is lower alkyl in the compound (I) is obtained by the condensation of carboxylic acid (II) and aniline (III). The compound (Ib) in which $R^1$ is hydrogen in the compound (I) is obtained by the hydrolysis of the compound (Ia).

The examples of condensation methods are, (1) the method that the compound (II) is converted to reactive carboxylic acid derivatives such as acidic chloride or mixed acid anhydrides and the reactive derivatives are then condensed with the compound (III), (2) the method that the compounds (II) and (III) are condensed using condensing agents such as 1,3-dicyclohexylcarbodiimide, 2-chloro-1-methylpyridinium iodide, N,N-bis(2-oxo-3-oxazolidinyl)phosphoric chloride or the like and other methods.

The proceeding of the method (2) is as follows.

Compound (II) is reacted with 1-5 equivalents of compound (III), in the presence of 1-2 equivalents of 2-chloro-1-methylpyridium iodide and 1-3 equivalents of base such as triethylamine, tributhylamine or diisopropylamine, in organic solvents such as dichloromethane, chloroform, 1,2-dichloroethane at a temperature between 4° C. and 100° C. for 0.5-6 hours to give compound (Ia).

The resulting compound (Ia) is hydrolysed in solvents (containing water) such as ethanol, dioxane, methanol using lithium hydroxide, sodium hydroxide, or potassium hydroxide at a temperature between 4° C. and 100° C. to give compound (Ib).

The compound (II) used as a starting material is produced by the method shown below.

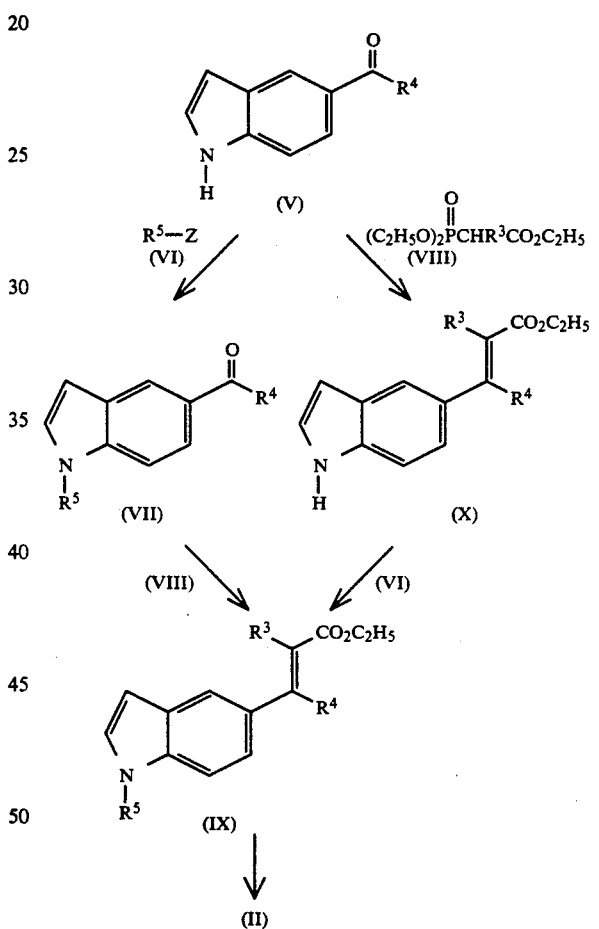

(wherein Z is chlorine, bromine, iodine, methanesulfonyloxy, trifluoromethanesulfonyloxy or p-toluenesulfonyloxy, and $R^3$, $R^4$ and $R^5$ have the same meaning as defined above).

Compound (V) is treated in solvents such as ether, tetrahydrofuran, dimenthylformamide or dimethyl sulfoxide, in the presence of bases such as 1-1.5 equivalents of lithium hydroxide, sodium hydroxide, potassium hydroxide, sodium hydride, or potassiumtert-butyrate, at −78° C. to 50° C. for 5 minutes to 1 hour. After treatment, the resulting compound is reacted with compound (VI) at −78° C. to 50° C. for 5 minutes to 6 hour to give compound (VII).

In the presence of 1-10 equivalents of bases such as sodium hydride, or potassiumtert-butyrate or lithium-diisopropylamide, compound (VIII) equivalent to the amount of the base is treated in solvents such as tetrahydrofuran, dimethylformamide or dimethyl sulfoxide at −50° C. to 50° C. for 5 minutes to 3 hours. After treatment, the compound (VII) is reacted with the resulting compound at 4° C. to 100° C. for 1-12 hours to give compound (IX).

Compound (IX) can be prepared by the other method described as follows. In the presence of 1-10 equivalents of base such as sodium hydride, or potassiumtert-butyrate, 1-2 equivalents of compound (VIII) is treated in solvents such as tetrahydrofuran, dimethylformamide or dimethyl sulfoxide at 0° to 50° C. for 5 minutes to 3 hours. After treatment, the compound (V) is reacted with the resulting compound at a temperature between 4° C. and 100° C. for 1-12 hours to give compound (X). The compound (X) is treated in solvents such as ether, tetrahydrofuran, dimethylformamide or dimethyl sulfoxide, in the presence of 1-3 equivalents of lithium hydroxide, sodium hydroxide, potassium hydroxide, sodium hydride, or potassiumtert-butyrate, at −78° C. to 50° C. for 5 minutes to 1 hour. After treatment, the resulting compound is reacted with 1-10 equivalents of the compound (VI) at −78° C. to 50° C. for 5 minutes to 6 hour to give compound (IX). Compound (IX) can also be prepared by using trimethyl silyl acetate instead of Compound (VIII).

The resulting compound (IX) is hydrolysed in organic solvents (containing water) such as ethanol, dioxane or methanol in the presence of lithium hydroxide, sodium hydroxide or potassium hydroxide at a temperature between 4° C. and 100° C. to give compound (II).

The compound (III) used as a starting material is prepared, for example, according to the method described in Japanese Published Unexamined Patent Application No. 139558/1989(EP294035A).

The intermediates and desired compounds prepared in the process described above may be isolated and purified by methods typically used in synthetic organic chemistry, such as filtration, extraction, washing, drying, concentration, recrystallization, and various chromatographies.

The intermediates obtained in the reaction process can be immediately used in the subsequent reaction, without any particular purification. In case that salt of Compound (I) are desired to be obtained and when Compound (I) is obtained in the form of salt, the Compound (I) salts are purified as it is, but when Compound (I) is obtained in the free form, the free compound (I) is dissolved or suspended in appropriate solvents and acid or base is added to form salt of compound (I).

Compound (I) and pharmaceutically acceptable salt thereof may be existed in the form of additional products formed with water or various solvents. The present invention also includes these additional products. The compound (I) obtained in the process described above can be existed as E/Z geometrical isomers. The present invention also includes all possible isomers and their mixtures in addition to geometrical isomers.

Table 1 shows the examples of compound (I) produced by the process of the present invention.

TABLE 1

| Comp. No. | $R^1$ | $R^2$ | $R^3$ | $R^4$ | $R^5$ | $R^6$ | X |
|---|---|---|---|---|---|---|---|
| 1 | $C_2H_5$ | H | H | $CH_3$ | CH(C6H5)2 | H | O |
| 2 | H | H | H | $CH_3$ | CH(C6H5)2 | H | O |
| 3 | H | H | H | $CH_3$ | —$CH_3$ | H | O |
| 4 | H | H | H | $CH_3$ | —$(CH_2)_2CH_3$ | H | O |
| 5 | H | H | H | $CH_3$ | —$(CH_2)_3CH_3$ | H | O |
| 6 | H | H | H | $CH_3$ | —$(CH_2)_4CH_3$ | H | O |
| 7 | H | H | H | $CH_3$ | —$(CH_2)_5CH_3$ | H | O |
| 8 | H | H | H | $CH_3$ | —$(CH_2)_6CH_3$ | H | O |
| 9 | H | H | H | $CH_3$ | —$CH_2CH(CH_3)_2$ | H | O |
| 10 | H | H | H | $CH_3$ | —$CH_2C(CH_3)_3$ | H | O |
| 11 | H | H | H | $CH_3$ | —$(CH_2)_3CH(CH_3)_2$ | H | O |
| 12 | H | H | H | $CH_3$ | —$CH_2CH=C(CH_3)_2$ | H | O |
| 13 | H | H | H | $CH_3$ | —$(CH_2)_2OCH_2CH_3$ | H | O |

TABLE 1-continued

| | | | | | | | |
|---|---|---|---|---|---|---|---|
| 14 | H | H | H | CH₃ | −CH₂CH(CH₃)(CH₂)₂CH₃ | H | O |
| 15 | H | H | H | CH₃ | −CH(CH₃)(CH₂CH₃) | H | O |
| 16 | H | H | H | CH₃ | −CH(CH₃)(CH₂)₂CH₃ | H | O |
| 17 | H | H | H | CH₃ | −CH(CH₃)(CH₂)₃CH₃ | H | O |
| 18 | H | H | H | CH₃ | −CH(CH₂CH₃)(CH₂)₃CH₃ | H | O |
| 19 | H | H | H | CH₃ | −CH((CH₂)₂CH₃)₂ | H | O |
| 20 | H | H | H | CH₃ | −CH((CH₂)₃CH₃)₂ | H | O |
| 21 | H | H | H | CH₃ | −CH(CH(CH₃)₂)((CH₂)₂CH₃) | H | O |
| 22 | H | H | H | CH₃ | −CH(CH₃)CH(CH₃)(CH₂)₂CH₃ | H | O |
| 23 | H | H | H | CH₃ | −CH₂−cyclohexyl | H | O |
| 24 | H | H | H | CH₃ | cyclohexyl | H | O |
| 25 | H | H | H | CH₃ | cyclohexenyl | H | O |
| 26 | H | H | H | CH₃ | −CH₂−phenyl | H | O |
| 27 | H | H | H | H | −CH₂−phenyl | H | O |
| 28 | H | H | CH₃ | H | −CH₂−phenyl | H | O |

TABLE 1-continued

| | | | | | | | |
|---|---|---|---|---|---|---|---|
| 29 | H | H | CH₃ | CH₃ | −CH₂−C₆H₅ | H | O |
| 30 | H | H | H | CH₃ | −CH₂−C₆H₄−F (4-) | H | O |
| 31 | H | H | H | CH₃ | −CH₂−C₆H₄−CH₃ (2-) | H | O |
| 32 | H | H | H | CH₃ | −CH₂−C₆H₄−CH₃ (3-) | H | O |
| 33 | H | H | H | CH₃ | −CH₂−C₆H₄−CH₃ (4-) | H | O |
| 34 | H | H | H | CH₃ | −CH₂−C₆H₄−CF₃ (4-) | H | O |
| 35 | H | H | H | CH₃ | −CH₂−C₆H₄−OCH₃ (4-) | H | O |
| 36 | H | H | H | CH₃ | −CH₂−C₆H₄−(CH₂)₃CH₃ (4-) | H | O |
| 37 | H | H | H | CH₃ | −CH₂−C₆H₄−C(CH₃)₃ (4-) | H | O |
| 38 | H | H | H | CH₃ | −CH(CH₃)−C₆H₅ | H | O |
| 39 | H | CH₃ | H | CH₃ | −CH(CH₃)−C₆H₅ | H | O |
| 40 | H | H | H | CH₃ | −CH(C₂H₅)−C₆H₅ | H | O |
| 41 | H | H | H | CH₃ | −CH((CH₂)₂CH₃)−C₆H₅ | H | O |

TABLE 1-continued
| | | | | | | | |
|---|---|---|---|---|---|---|---|
| 42 | H | H | H | CH₃ | 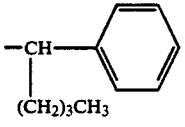 | H | O |
| 43 | H | H | H | CH₃ | 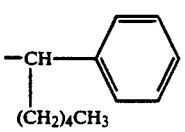 | H | O |
| 44 | H | H | H | CH₃ | 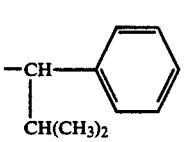 | H | O |
| 45 | H | H | H | CH₃ | 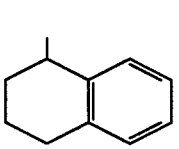 | H | O |
| 46 | H | H | H | CH₃ | 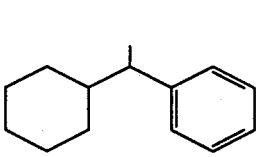 | H | O |
| 47 | H | H | H | CH₃ | 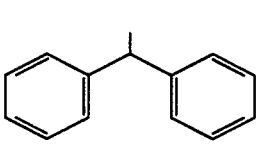 | 5-Cl | O |
| 48 | H | H | H | CH₃ | 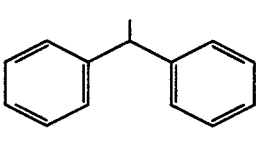 | 4-F | O |
| 49 | H | H | H | CH₃ | 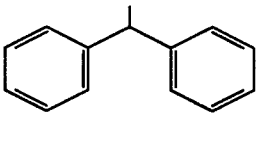 | 4-CH₃ | O |
| 50 | H | H | H | CH₃ | 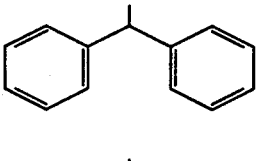 | 5-CH₃ | O |
| 51 | H | H | H | CH₃ | 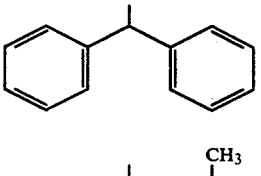 | H | S |
| 52 | H | H | H | CH₃ | 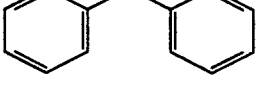 | H | O |

TABLE 1-continued
| 53 | H | H | H | CH₃ | 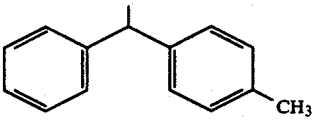 | H | O |
| 54 | H | H | H | CH₃ | 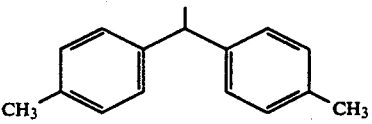 | H | O |
| 55 | H | H | H | CH₃ | 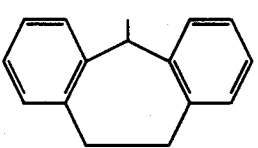 | H | O |
| 56 | H | H | H | CH₃ | 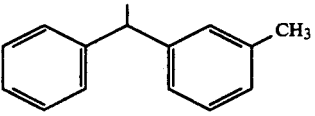 | H | O |
| 57 | H | H | H | CH₃ | 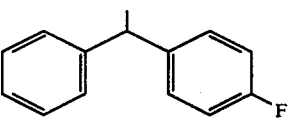 | H | O |
| 58 | H | H | H | CH₃ | 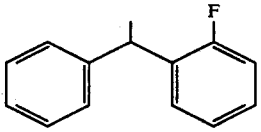 | H | O |
| 59 | H | H | H | CH₃ | 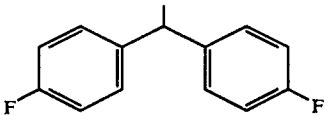 | H | O |
| 60 | H | H | H | CH₃ | 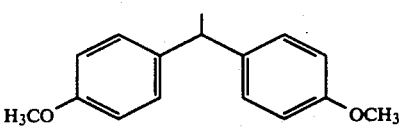 | H | O |
| 61 | H | H | H | CH₃ | 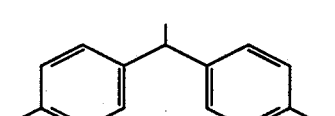 | H | O |
| 62 | H | H | H | CH₃ | 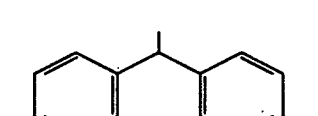 | 4-F | O |
| 63 | H | H | H | CH₃ | 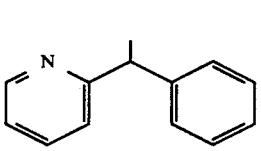 | H | O |

TABLE 1-continued
| 64 | H | H | H | CH$_3$ | 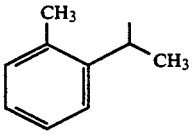 | H | O |
| 65 | H | H | H | CH$_3$ | 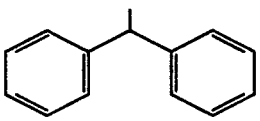 | 3-F | O |
| 66 | H | H | H | CH$_3$ | 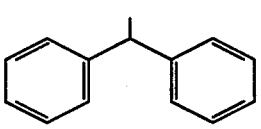 | 5-F | O |
| 67 | H | H | H | CH$_3$ | 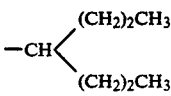 | 4-F | O |
| 68 | H | H | H | CH$_3$ | 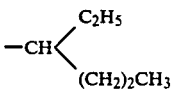 | H | O |
| 69 | H | H | H | CH$_3$ | 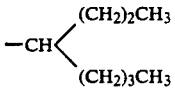 | H | O |
| 70 | H | H | H | CH$_3$ | 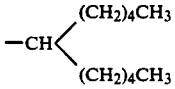 | H | O |
| 71 | H | H | H | CH$_3$ | 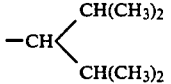 | H | O |
| 72 | H | H | H | CH$_3$ | 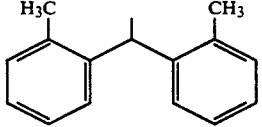 | H | O |
| 73 | H | H | H | CH$_3$ | 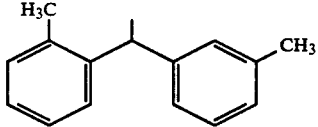 | H | O |
| 74 | H | H | H | CH$_3$ | 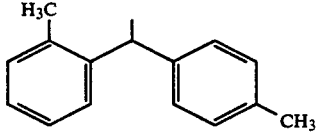 | H | O |
| 75 | H | H | H | CH$_3$ | 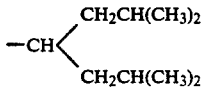 | H | O |
| 76 | H | H | H | CH$_3$ | 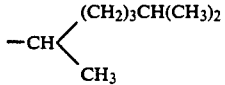 | H | O |

TABLE 1-continued
| | | | | | | | |
|---|---|---|---|---|---|---|---|
| 77 | H | H | H | CH₃ | 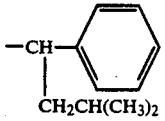 | H | O |
| 78 | H | H | H | CH₃ | 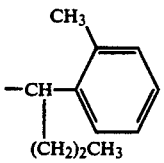 | H | O |
| 79 | H | H | H | CH₃ | 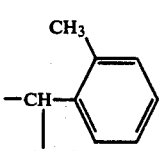 | H | O |
| 80 | H | H | H | CH₃ | 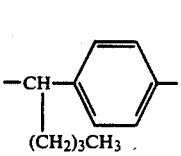 | H | O |
| 81 | H | H | H | CH₃ | 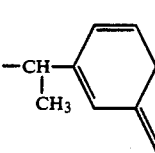 | H | O |
| 82 | H | H | H | CH₃ | 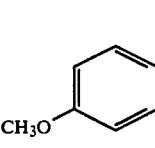 | H | O |
| 83 | H | H | H | CH₃ | 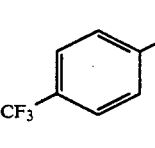 | H | O |
| 84 | H | H | H | CH₃ | 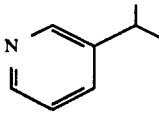 | H | O |
| 85 | H | H | H | CH₃ | 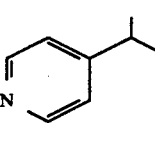 | H | O |
| 88 | H | H | H | CH₂CH₃ | 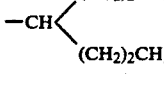 | H | O |
| 89 | H | H | H | CH₂CH₃ | 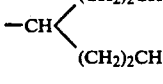 | 4-F | O |
| 90 | H | H | H | CH₂CH₃ | 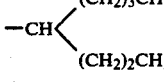 | H | O |

TABLE 1-continued
| | R3 | R4 | R5 | R1 | R2 | R6 | X | |
|---|---|---|---|---|---|---|---|---|
| 91 | H | H | H | CH₂CH₃ | —CH((CH₂)₃CH₃)((CH₂)₂CH₃) | 4-F | O | |
| 92 | H | H | H | CH₂CH₃ | —CH(CH₂CH(CH₃)₂)(CH₂CH(CH₃)₂) | H | O | |
| 93 | H | H | H | CH₂CH₃ | —CH(C₆H₅)₂ | H | O | |
| 94 | H | H | H | CH₂CH₃ | —CH(4-F-C₆H₄)₂ | H | O | |
| 95 | H | H | H | CH(CH₃)₂ | —CH(4-F-C₆H₄)₂ | H | O | |
| 96 | H | H | H | (CH₂)₂CH₃ | —CH((CH₂)₂CH₃)₂ | H | O | |
| 97 | H | H | H | (CH₂)₂CH₃ | —CH(4-F-C₆H₄)₂ | H | O | |
| 98 | H | H | H | (CH₂)₂CH₃ | —CH(4-F-C₆H₄)₂ | 4-F | O | |
| 99 | H | H | H | —CH(CH₂CH₂) (cyclopropyl) | —CH(4-F-C₆H₄)₂ | H | O | |
| | R3 | R4 | R5 | R1 | R2 | R6 | X | pos |
|---|---|---|---|---|---|---|---|---|
| 86 | H | H | H | CH₃ | —CH((CH₂)₂CH₃)₂ | H | O | 3 |
| 87 | H | H | H | CH₃ | —CH((CH₂)₂CH₃)₂ | H | O | 4 |

The pharmacological effects of the compound (I) are illustrated below.

Experiment 1

Acute Toxicity Test

Test compounds (300 mg/kg) were orally administered to male dd mice weighing 20±1 g (each group consists of three animals). Minimum lethal dose (MLD) was determined by observing mortality seven days after the administration. The results are shown in Table 2.

TABLE 2

| Comp. No. | Acute toxicity (MLD) mg/kg | Comp. No. | Acute toxicity (MLD) mg/kg |
|---|---|---|---|
| 2 | >300 | 6 | >300 |
| 7 | >300 | 15 | >300 |
| 16 | >300 | 17 | >300 |
| 18 | >300 | 20 | >300 |
| 41 | >300 | 42 | >300 |
| 43 | >300 | 44 | >300 |
| 45 | >300 | 52 | >300 |
| 53 | >300 | 54 | >300 |

Experiment 2

Inhibition effects on steroid 5α-reductase activity

The measurements of inhibition effects of test compounds on steroid 5α-reductase activity were performed according to the method described by Liang et al. [J. Biol. Chem., 259, 734 (1984)] as follows.

The prostates from male rats were homogenated in three tissue volumes of 20 mM sodium phosphate buffer (pH 6.5; containing 0.32M sucrose and 1 mM dithiothreitol). The homogenate was centrifuged at 140,000 X g for one hour. The precipitate was suspended in the buffer described above and the suspension was centrifuged at 140,000 X g for one hour. The precipitate was resuspended in the buffer described above and the solution (30–50 mg protein/ml) was used as enzyme in following assay.

[4-$^{14}$C]-testosterone (1.5 nmol), NADPH (75 nmol), the enzyme (1 mg protein) and test compound in a total volume of 0.5 ml of 40 mM sodium phosphate buffer [pH 6.5, containing 1 mM dithiothreitol] was incubated at 37° C. After 20 minutes the enzyme activity was stopped by the addition of 2 ml of ethyl acetate. The mixture was then centrifuged at 1,000 g, for 5 minutes. The ethyl acetate layer was transferred to another tube and evaporated to dryness. The steroids were taken up in 50 μl of ethyl acetate and separated by thin layer chromatography (TLC) on silica gel in a developing solvent (ethyl acetate: cyclohexane = 1:1). The radioactivity of testosterone and dihydrotestosterone on the TLC plate was measured by a TLC scanner. Hence the enzyme activity and inhibition rate of enzyme activity were calculated. The results were shown in Table 3-1 and Table 3-2.

TABLE 3-1

| Comp. No. | inhibition rate (%), $10^{-7}$M | Comp. No. | inhibition rate (%), $10^{-7}$M |
|---|---|---|---|
| 2 | 95 | 40 | 78 |
| 6 | 81 | 41 | 90 |
| 16 | 88 | 42 | 89 |
| 17 | 94 | 43 | 74 |
| 18 | 90 | 44 | 78 |
| 19 | 94 | 45 | 77 |
| 20 | 79 | 48 | 93 |
| 21 | 88 | 52 | 90 |
| 22 | 70 | 53 | 84 |
| 38 | 78 | 54 | 89 |

TABLE 3-2

| Comp. No. | inhibition rate (%), $10^{-7}$M | Comp. No. | inhibition rate (%), $10^{-7}$M |
|---|---|---|---|
| 57 | 92 | 80 | 74 |
| 58 | 93 | 82 | 87 |
| 59 | 92 | 83 | 90 |
| 60 | 87 | 84 | 66 |
| 63 | 72 | 85 | 78 |
| 67 | 98 | 88 | 95 |
| 68 | 92 | 89 | 95 |
| 69 | 92 | 90 | 79 |
| 75 | 90 | 91 | 98 |
| 76 | 70 | 92 | 91 |
| 77 | 97 | 93 | 94 |
| 78 | 94 | 94 | 97 |
| 79 | 90 | 95 | 75 |

Compound (I) or pharmaceutically acceptable salts thereof can be administered directly but it is preferable that compound (I) can be administered by various pharmaceutical compositions with pharmaceutically acceptable carrier. These pharmaceutical compositions are used for animals and humans. The administration route of compound (I) includes a peroral route or parenteral routes such as an intrarectal, perifoneal, subcutaneous, intramuscular, or intravenous rout and any of pharmaceutical carriers are used. It is preferable that the most therapeutically effective route is selected as administration route of Compound (I).

An administrative form may be capsules, tablets, granules, powders, syrups, emulsions, suppository and injection. Liquid preparations such as emulsions and syrups suitable for oral administration may be prepared using water, saccharides such as sucrose, sorbitol and fructose, glycols such as polyethylene glycol and propylene glycol, oils such as sesame oil, olive oil and soybean oil, preservatives such as p-hydroxybenzoic acid esters and flavors such as strawberry and peppermint. Capsules, tablets and granules may be prepared using excipients such as lactose, glucose, sucrose and mannitol, disintegrants such as starch and alginic acid soda, lubricants such as magnesium stearate and talc, binders such as poly vinyl alcohol, hydroxypropylcellulose and gelatin, surfectant such as fatty acid ester and plasticizer such as glycerin.

Parenterally suitable preparations may be preferably sterilized aqueous ones containing active compounds isotonic to blood. For example, injections are prepared using carrier comprising salt solution, glucose solution or a mixture of salt and glucose.

Preparations for local use are prepared by dissolving or suspending active compounds in one or more solvent(s) such as mineral oil, petroleum and multivalent alcohol or in other agents used for pharmaceutical preparations.

Preparations for intrerectal administration are used as suppository formed with carriers such as cacao butter and hydrogenated fatty acid.

Parenterally suitable preparations may contain one or more ingredients used for preparations for oral administration, such as diluents, perfume, preservatives, oxidants, excipients, disintegrants, binders, surfactants and plasticizers.

The effective dosage and the number of administration of compound (I) or pharmaceutically acceptable salts thereof may depend on an administrative form and the ages, weights, symptoms and conditions of patients. In the case of oral administration, a typical administrative dosage is 1 mg–1 g/adult once or few times a day. In the case of parenteral administration, a typical administrative dosage is 0.1–100 mg/adult once or few times a day for intravenous administration and 10 $\mu$g–100 mg/adult once or few times a day for transdermal administration. An administrative dosage depends on various conditions described above.

The present invention is further illustrated by the following Reference Examples, Examples and Formulation Examples.

REFERENCE EXAMPLE 1

Ethyl 3-(indol-5-yl)isocrotonate (Compound A)

After 12.5 g of sodium hydride (60% oil) was washed with pentane under nitrogen stream, 180 ml of tetrahydrofuran (THF) was added. 2–3 drops of ethanol were added to the suspension ethyl diethylphosphonoacetate (70.4 g) was added dropwise at 0° C. After the mixture was stirred at 0° C. for 30 minutes, 10.0 g of 5-acetylindole in 70 ml of THF was added dropwise. The reaction mixture was stirred at room temperature for 30 minutes and then refluxed for 8 hour. Water was added and the mixture was extracted with ethyl acetate. The organic layer was washed with water and then with saturated brine, dried over anhydrous magnesium sulfate, filtered and concentrated under reduced pressure. The residue obtained was purified by silica gel column chromatography (hexane: ethyl acetate=5:1) to give 9.6 g of compound A as a yellow syrup.

IR (liquid film) cm$^{-1}$: 1680, 1603, 1195, 1101.

$^1$HNMR (CDCl$_3$) ($\delta$, ppm): 1.32(t, 3H, J=7 Hz), 2.67(d, 3H, J=1 Hz), 4.22 (q, 2H, J=7 Hz), 6.21(d, 1H, J=1 Hz), 6.56(dd, 1H, J=2 & 3 Hz), 7.33 (s, 2H), 7.79(s, 1H), 8.3 (brs, 1H).

REFERENCE EXAMPLE 2

3-(Penylindol-5-yl)isocrotonic acid (Compound B)

To a solution of 2.29 g of compound A in 30 ml of dimethylformamide (DMF) was added 1.39 g of potassium tert-butoxide at 0° C. and the mixture was stirred for 30 minutes. Then 1.7 ml of 1-iodopentane in 10 ml of DMF was added dropwise to the reaction mixture at 0° C. After the reaction mixture was stirred at 0° C. for 1 hour, water was added and then the mixture was extracted with ethyl acetate. The organic layer was washed with water and then with saturated brine, dried over anhydrous magnesium sulfate, filtered and concentrated under reduced pressure. The residue obtained was purified by silica gel column chromatography (hexane: ethyl acetate=5:1) to give 2.28 g of ethyl 3-(1-penylindol-5-yl)isocrotonate as an oil.

IR (liquid film) cm$^{-1}$: 2956, 2930, 1709, 1611, 1151.

$^1$HNMR (CDCl$_3$) ($\delta$, ppm): 0.88(t, 3H, J=6 Hz), 1.24–1.39(m, 7H), 1.65–2.05 (m, 2H), 2.67(s, 3H), 4.0–4.32(m, 4H), 6.19(s, 1H), 6.49(d, 1H, J=3 Hz), 7.08(d, 1H, J=3 Hz), 7.15–7.62(m, 2H), 7.77(s, 1H).

A mixture of 2.20 g of ethyl 3-(1-pentylindol-5-yl)isocrotonate, 22 ml of 1N lithium hydroxide and 40 ml of 1,4-dioxane was stirred at 70°–80° C. for 4 hours. The reaction mixture was concentrated under reduced pressure and 50 ml of water was added. The pH of the mixture was adjusted to 2 with 4N hydrochloric acid and the mixture was stirred at room temperature for 1 hour. The precipitated crystals were collected by filtration, washed and dried to give 1.92 g of a crude product. The crude product was recrystallized from isopropylether to give 0.91 g of the compound B as white crystalls.

Melting point: 69°–75° C.

IR (KBr) cm$^{-1}$; 3500, 2970, 1692, 1590, 1216.

$^1$HNMR (CDCl$_3$) ($\delta$, ppm): 0.89(t, 3H, J=6 Hz), 1.2–1.6(m, 4H), 1.65–2.05(s, 2H), 2.69(s, 3H), 4.11(t, 2H, J=7 Hz), 6.24(d, 1H, J=1 Hz), 6.55(d, 1H, J=3 Hz), 7.11(d, 1H, J=3 Hz), 7.34–7.37(m, 2H), 7.81(s, 1H).

REFERENCE EXAMPLES 3

5-Acetyl-1-benzyhydrylindole (Compound C)

To a solution of 8.0 g of 5-acetylindole in 120 ml of DMF was added 6.76 g of potassium tert-butoxide at 0° C. and the mixture was stirred for 30 minutes. A solution of 18.6 g of benzhydryl bromide in 50 ml of DMF was added dropwise to the reaction mixture at 0° C. The reaction mixture was stirred at 0° C. for 1 hour and then at room temperature for 3 hours. After addition of water, the reaction mixture was extracted with ethyl acetate. The organic layer was washed with water and then with saturated brine, dried over anhydrous magnesium sulfate, filtered and concentrated under reduced pressure. The residue obtained was purified by silica gel column chromatography (hexane: ethyl acetate=5.1) to give 13.71 g of compound C as a white crystals.

IR (KBr)cm$^{-1}$: 1669, 1607, 1452, 1361.

$^1$HNMR (CDCl$_3$) ($\delta$, ppm): 2.62(s, 3H), 6.60(d, 1H, J=3 Hz), 6.84(s, 1H), 6.90(d, 1H, J=3 Hz), 7.03–7.85(m, 12H), 8.30(d, 1H, J=1 Hz).

REFERENCE EXAMPLE 4

3-(1-Benzhydrylindol-5-yl)isocrotonic acid (Compound D)

After 8.42 g of sodium hydride (60% oil) was washed with pentane under nitrogen stream, 110 ml of THF was added. After addition of 2–3 drops of ethanol, 47.08 g of ethyl diethylphosphonoacetate was added dropwise to the suspension at 0° C. The mixture was stirred at 0° C. for 30 minutes and then a solution of 13.70 g of the compound C in 50 ml of THF was added dropwise. After being stirred at room temperature for 30 minutes, the reaction mixture was refluxed for 7 hours. After addition of water, the mixture was extracted with ethyl acetate. The organic layer was washed with water and then with saturated brine, dried over anhydrous magnesium sulfate, filtered and concentrated under reduced pressure. The residue obtained was purified by silica gel column chromatography (hexane: ethyl acetate=3:1) to give 14.31 g of ethyl 3-(1-benzhydrylindol-5-yl)isocrotonate as an oil.

IR (liquid film) cm$^{-1}$: 1708, 1620, 1608, 1451, 1151.

$^1$HNMR (CDCl$_3$) ($\delta$, ppm): 1.30(t, 3H, J=7 Hz), 2.64(d, 3H, J=1 Hz), 4.20 (q, 2H, J=7 Hz), 6.17(d, 1H, J=1 Hz), 6.50(d, 1H, J=3 Hz), 6.81(s, 1H), 6.85(d, 1H, J=3 Hz), 7.03–7.36(m, 12H), 7.79(s, 1H).

A mixture of 4.30 g of ethyl 3-(1-benzhydrylindol-5-yl)isocrotonate, 80 ml of 1N lithium hydroxide and 130 ml of 1,4-dioxane was stirred at 60°–70° C. for 10 hours. The reaction mixture was concentrated under reduced pressure and then 200 ml of water was added. After the pH of the mixture was adjusted to 2 with hydrochloric acid, the mixture was stirred at room temperature for 1 hour. The precipitated crystals were collected by filtration, washed and dried to give 12.69 g of a crude product. The crude product was recrystallized from isopropylether to give 6.0 g of compound D as a white crystals. Melting point: 173°-175° C.

IR (KBr)cm$^{-1}$: 3500, 1680, 1602, 1447.

$^1$HNMR (CDCl$_3$) (δ, ppm): 2.66(d, 3H, J=1 Hz), 6.21(d, 1H, J=1 Hz), 6.52 (d, 1H, J=3 Hz), 6.81(s, 1H), 6.86(d, 1H, J=3 Hz), 7.04-7.36(m, 12H), 7.81(s, 1H).

REFERENCE EXAMPLE 5

[5-cyclopropylcarbonyl-1-(4,4'-difluorobenzhydryl)indol-5-yl]-trans-2-acrylic acid (Compound E).

To a solution of 0.53 ml of diisopropylamine in 2 ml of THF, 2.33 ml of 1.65M n-butyllithium in hexane was added dropwise at 0° C. After being stirred at 0° C. for 30 min, the reaction mixture was cooled to −78° C., then 0.59 ml of ethyl trimethylsilylacetate was added. After the mixture was stirred at the same temperature for 40 min., 0.62 g of 5-cyclopropyl-1-(4,4'-difluorobenzhydryl) indole in 3.2 ml of THF was added. Then the mixture was stirred for 1 hour at 0° C.

After addition of water, the reaction mixture was extracted with ethyl acetate. The organic layer was washed with 1N HCl, saturated sodium hydrogen carbonate, saturated brine successively, dried, filtered, and concentrated under reduced pressure. The resulting residue was purified by silica gel column chromatography (hexane: ethyl acetate=6:1) to give 0.24 g of ethyl [5-cyclopropylcarbonyl-1-(4,4'-diflurobenzhydryl)indol-5-yl]-trans-2-acrylate as an oil.

A mixture of 0.2 g of ethyl [5-cyclopropylcarbonyl-1-(4,4' difluorobenzhydryl)indol-5-yl]-trans-2-acrylate, 1.75 ml of 1N lithium hydroxide and 8.0 ml of 1,4-dioxane was stirred at 60°-70° C. for 3 days. The reaction mixture was concentrated under reduced pressure and 20 ml of water was added. The pH of the mixture was adjusted to 3 with 4N HCl. The reaction mixture was extracted with ethyl acetate, which was washed with water, dried over anhydrous magnesium sulfate, filtered and concentrated under reduced pressure to give 0.15 g of compound E as an amorphous form.

$^1$H-NMR (CDCl$_3$) (δ, ppm): 0.50-0.64(m, 2H), 0.80-0.97(m, 2H), 2.90-3.20(m, 1H), 5.87 (s, 1H), 6.49(d, 1H, J=3.3 Hz), 6.76(s, 1H), 6.80(d, 1H, J=3.3 Hz), 6.89-7.18(m, 10H), 7.44 (d, 1H, J=0.9 Hz).

REFERENCE EXAMPLE 6

Ethyl 4-{3-[3-[1-(1-propylbutyl)indol-5-yl]isocrotonoylamino]phenoxy} butyrate (Compound F)

To a mixture of 0.60 g of ethyl 4-(3-aminophenoxy)acetate, 0.50 g of 3-[1-(1-propylbutyl)indol-5-yl]isocrotonic acid obtained by the same procedure described in reference example 1-4, 0.51 g of N,N-bis(2-oxo-3-oxazolidinyl)phosphinic chloride and 11 ml of dichloromethane was added 0.51 ml of triethylamine, and the reaction mixture was stirred at room temperature for 1 hour. After addition of water, the reaction mixture was extracted with ethyl acetate. The organic layer was washed with saturated brine, dried over anhydrous magnesium sulfate, filtered and concentrated under reduced pressure. The resulting residue was purified by silica gel column chromatography (hexane: ethyl acetate=3:1) to give 0.35 g of compound F as an yellow oil.

$^1$H-NMR (CDCl$_3$) (δ, ppm): 0.70-1.10(m, 6H), 1.05-1.50(m, 7H), 1.65-2.25(m, 6H), 2.69 (t, 2H, J=7.3 Hz), 2.69(s, 3H), 3.80-4.40(m, 5H), 6.25(s, 1H), 6.40-6.70(m, 1H), 6.48(d, 1H, J=3.6 Hz), 7.00-7.50(m, 5H), 7.28(s, 2H), 7.72(s, 1H), 7.96(s, 1H).

EXAMPLE

Example 1

Ethyl 4-{2-[3-(1-benzhydrylindol-5-yl)isocrotonoylamino]phenoxy}butyrate (Compound 1)

To a mixture of 1.76 g of ethyl 4-(2-aminophenoxy)butyrate, 1.20 g of 2-chloro-1-methylpyridinium iodide, 2.25 ml of tributylamine and 10 ml of dichloromethane was added at reflux a suspension of 1.45 g of compound D (obtained in Reference example 4) in 6 ml of dichloromethane and then the mixture was refluxed for 3 hours. After addition of water, the organic layer was extracted with ethyl ether. The organic layer was washed with water and then with saturated brine, dried over anhydrous magnesium sulfate, filtered and concentrated under reduced pressure. The residue obtained was purified by silica gel column chromatography (toluene: ethyl acetate=98:2) to give 1.0 g of compound 1 as an oil.

IR (liquid film) cm$^{-1}$: 3370, 1726, 1672, 1601, 1520, 1520, 1449.

$^1$HNMR (CDCl$_3$) (δ, ppm): 1.11(t, 3H, J=7 Hz), 2.05-2.60(m, 4H), 2.72(d, 1H, J=1 Hz), 3.92-4.17(m, 4H), 6.41(d, 1H, J=1 Hz), 6.52(d, 1H, J=3 Hz), 6.81-7.45(m, 16 H), 7.83(d, 1H, J=1 Hz), 8.03 (brs, 1H), 8.46-8.56 (m, 1H).

Example 2

4-{2-[3-(1-benzhydrylindol-5-yl)isocrotonoylamino]phenoxy}butyric acid (Compound 2)

A mixture of 990 mg of compound 1 (obtained in Example 1), 3.5 ml of 1N lithium hydroxide/ethanol (4:6) and 3.5 ml of 1,4-dioxane was stirred at room temperature overnight. The reaction mixture was concentrated under reduced pressure and 10 ml of water was added to the residue. The pH of the mixture was adjusted to 2 with hydrochloric acid and the mixture was stirred at room temperature for 1 hour. The precipitated crystals were collected by filtration, washed and dried to give 729 mg of a crude product. The crude product was recrystallized from isopropanol to give 662 mg of compound 2 as a white crystals.

Melting point: 158°-162° C.

IR (KBr)cm$^{-1}$: 3450, 3340, 1717, 1638, 1603, 1596, 1539, 1452. $^1$HNMR (CDCl$_3$) (δ, ppm): 2.02-2.60(m, 4H), 2.69(d, 3H, J=1.1 Hz), 4.08 (t, 2H, J=6.1 Hz), 6.30(d, 1H, J=1.1 Hz), 6.51(d, 1H, J=3.3 Hz), 6.81-7.36(m, 17H), 7.79(s, 1H), 7.90(s, 1H), 8.3-8.8(m, 1H).

EXAMPLE 3

4-{2-[3-(1-methylindol-5-yl)isocrotonoylamino]phenoxy}butyric acid (Compound 3)

0.46 g of compound 3 was obtained in a similar manner to those described in the Example 1 and 2 using 2.16 g of ethyl 4-(2-aminophenoxy)butyrate and 1.04 g of 3-(1-methylindol-5-yl)isocrotonic acid obtained according to the procedures described in the Reference Examples 1-4.

Melting point: 132°-133.5° C.

| Elementary analysis (%): C₂₃H₂₄N₂O₄ | | | |
|---|---|---|---|
| | C | H | N |
| Calculated value; | 70.39 | 6.16 | 7.14 |
| Observed value; | 70.61 | 6.34 | 6.96 |

IR (KBr)cm⁻¹: 3330, 1714, 1643, 1610, 1595, 1532, 1455.

¹HNMR (CDCl₃) (δ, ppm): 2.05-2.61(m, 4H), 2.70(d, 3H, J=1.3 Hz), 3.77 (s, 3H), 6.31(d, 1H, J=1 Hz), 6.48(d, 1H, J=3 Hz), 6.70-7.45(m, 6H), 7.77 (s, 1H), 7.90 (brs, 1H), 8.32-8.50(m, 1H).

Example 4

4-{2-[3-(1-propylindole-5yl)isocrotonoyl amino]phenoxy}butyric acid (Compound 4)

177 mg of compound 4 was obtained in a similar manner to those described in the Example 1 and 2 using 481 mg of ethyl 4-(2-aminophenoxy)butyrate and 262 mg of 3-(1-propylindol-5-yl)isocrotonic acid obtained according to the procedures described in the Reference Examples 1-4.

Melting point: 153°-154° C.

| Elementary analysis (%): C₂₅H₂₈N₂O₄ | | | |
|---|---|---|---|
| | C | H | N |
| Calculated value; | 71.41 | 6.71 | 6.66 |
| Observed value: | 71.44 | 7.03 | 6.53 |

IR (KBr)cm⁻¹: 3450, 1718, 1633, 1610, 1595, 1540, 1455.

¹HNMR (DMSO-d₆) (δ, ppm): 0.84(t, 3H, J=7.4 Hz), 1.75-2.25(m, 4H), 2.63 (s, 3H), 4.0-4.22(m, 4H), 6.48(d, 1H, J=3.1 Hz), 6.69(s, 1H), 7.38(d, 1H, J=3.1 Hz), 7.46(s, 2H), 7.75-8.1(m, 3H), 7.80(s, 1H), 8.03(d, 1H, J=3 Hz), 8.92(s, 1H).

Example 5

4-{2-[3-(1-buthylindol-5-yl)isocrotonoyl amino]phenoxy}butyric acid (Compound 5)

90 mg of compound 5 was obtained in a similar manner to those described in the Example 1 and 2 using 179 mg of ethyl 4-(2-aminophenoxy)butyrate and 206 mg of 3-(1-butylindol-5-yl)isocrotonic acid obtained according to the procedures described in the Reference Examples 1-4.

Melting point: 154°-155.5° C.

| Elementary analysis (%): C₂₆H₃₀N₂O₄·0.5 H₂O | | | |
|---|---|---|---|
| | C | H | N |
| Calculated value; | 70.41 | 7.05 | 6.32 |
| Observed value; | 70.81 | 7.19 | 6.35 |

IR (KBr)cm⁻¹: 3316, 1720, 1630, 1610, 1594, 1536, 1452.

¹HNMR (CDCl₃+DMSO-d₆) (δ, ppm): 0.94(t, 3H, J=6.8 Hz), 1.21-2.60(m, 8H), 2.72(d, 3H, J=1.1 Hz), 4.06-4.21(m, 4H), 6.44(d, 1H, J=1.1 Hz), 6.52(d, 1H, J=3.1 Hz), 6.87-7.43(m, 7H), 7.82(s, 1H), 8.14 (brs, 1H), 8.4-8.5 (m, 1H).

Example 6

4-{2-[3-(1-pentylindol-5-yl)isocrotonoyl amino]phenoxy}butyric acid (Compound 6)

0.86 g of compound 6 was obtained in a similar manner to those described in Example 1 and 2 using 1.41 g of ethyl 4-(2-aminophenoxy)butyrate and 0.86 g of compound B obtained according to the procedures described in the Reference Example 2.

Melting point: 129°-132° C.

| Elementary analysis (%): C₂₇H₃₂N₂O₄ | | | |
|---|---|---|---|
| | C | H | N |
| Calculated value; | 72.30 | 7.19 | 6.25 |
| Observed value; | 72.54 | 7.58 | 6.35 |

IR (KBr)cm⁻¹: 3370, 2970, 1720, 1642, 1606, 1595, 1538, 1456.

¹HNMR (CDCl₃) (δ, ppm): 0.89(t, 3H, J=5.1 Hz), 1.15-1.5(m, 4H), 1.6-2.35(m, 4H), 2.54(t, 2H, J=6.4 Hz), 2.71(s, 3H), 4.09(t, 4H, J=6.4 Hz), 6.32(d, 1H, J=1.1 Hz), 6.51(d, 1H, J=3.5 Hz), 6.83-7.11(m, 4H), 7.35(s, 2H), 7.78(s, 1H), 7.92(s, 1H), 8.25-8.5(m, 1H).

EXAMPLE 7

4-{2-[3-(1-hexylindol-5-yl)isocrotonoylamino]phenoxy}butyric acid (Compound 7)

108 mg of compound 7 was obtained in a similar manner to those described in the Examples 1 and 2 using 580 mg of ethyl 4-(2-aminophenoxy)butyrate and 366 mg of 3-(1-hexylindol-5-yl)isocrotonic acid obtained according to the procedures described in the Reference Examples 1-4.

Melting point: 107°-108° C.

| Elementary analysis (%): C₂₈H₃₄N₂O₄ | | | |
|---|---|---|---|
| | C | H | N |
| Calculated value; | 72.70 | 7.41 | 6.06 |
| Observed value; | 72.65 | 7.69 | 5.98 |

IR (KBr)cm⁻¹: 3450, 3320, 2922, 1722, 1635, 1613, 1538, 1454.

¹HNMR (DMSO-d₆) (δ, ppm): 0.7-0.95(m, 3H), 1.25 (brs, 6H), 1.5-2.6(m, 6H), 2.62(s, 3H), 4.0-4.17(m, 4H), 6.48(d, 1H, J=3.1 Hz), 6.69(s, 1H), 7.37(d, 1H, J=3.1 Hz), 7.46(s, 2H), 7.80(s, 1H), 8.11(d, 1H, J=7 Hz), 8.92(s, 1H).

EXAMPLE 8

4-{2-[3-(1-heptylindol-5yl)isocrotonoylamino]phenoxy}butyric acid (Compound 8)

217 mg of compound 8 was obtained in a similar manner to those described in the Examples 1 and 2 using 701 mg of ethyl 4-(2-aminophenoxy)butyrate and 470 mg of 3-(1-heptylindol-5 -yl)isocrotonic acid obtained according to the procedures described in the Reference Examples 1-4.

Melting point: 95.5°-96.5° C.

| Elementary analysis (%): $C_{29}H_{36}N_2O_4$ | | | |
|---|---|---|---|
| | C | H | N |
| Calculated value; | 73.08 | 7.61 | 5.88 |
| Observed value; | 73.25 | 7.93 | 5.84 |

IR (KBr)cm$^{-1}$: 3430, 3330, 2930, 1723, 1635, 1613, 1598, 1537, 1455.

$^1$HNMR (CDCl$_3$) (δ, ppm): 0.87(t, 3H, J=5 Hz), 1.1–1.5(m, 8H), 1.6–2.65(m, 6H), 2.71(d, 3H, J=1.1 Hz), 4.09(t, 2H, J=6.5 Hz), 6.33(d, 1H, J=1.1 Hz), 6.48(d, 1H, J=3.1 Hz), 6.7–7.4(m, 6H), 7.70(s, 1H), 7.93(s, 1H), 8.3–8.55(m, 1H).

EXAMPLE 9

4-{2-[3-[1-(2-methylpropyl)indol-5-yl]iso-crotonoylamino]phenoxy}butyric acid (Compound 9)

0.58 g of compound 9 was obtained in a similar manner to those described in the Examples 1 and 2 using 1.10 g of ethyl 4-(2-aminophenoxy)butyrate and 0.64 g of 3-[1-(2-methylpropyl)indol-5-yl]isocrotonic acid obtained according to a similar manner to procedures described in the Reference Examples 1–4.

Melting point: 153°–155.5° C.

| Elementary analysis (%): $C_{26}H_{30}N_2O_4$ | | | |
|---|---|---|---|
| | C | H | N |
| Calculated value; | 71.87 | 6.96 | 6.45 |
| Observed value; | 71.82 | 7.20 | 6.42 |

IR (KBr)cm$^{-1}$: 3320, 2970, 1717, 1632, 1608, 1595, 1538, 1454.

$^1$HNMR (CDCl$_3$) (δ, ppm): 0.92(d, 6H, J=6.6 Hz), 1.95–2.35(m, 2H), 2.54 (t, 2H, J=6 Hz), 2.71(d, 3H, J=1.1 Hz), 3.89(d, 2H, J=7 Hz), 4.08(t, 2H, J=5.7 Hz), 6.32(d, 1H, J=1.1 Hz), 6.50(t, 1H, J=3.1 Hz), 6.6–7.4(m, 6H), 7.78(s, 1H), 7.91(s, 1H), 8.25–8.55(m, 1H).

Example 10

4-{2-[3-[1-(2,2-dimethylpropyl)indol-5-yl]iso-crotonoylamino]phenoxy}butyric acid (Compound 10)

1.74 g of compound 10 was obtained in a similar manner to those described in the Examples 1 and 2 using 3.16 g of ethyl 4-(2-aminophenoxy)butyrate and 1.93 g of 3-[1-(2,2-dimethylpropyl)indol-5-yl]isocrotonic acid obtained according to the procedures described in the Reference Examples 1–4.

Melting point: 141°–143° C.

| Elementary analysis (%): $C_{27}H_{32}N_2O_4 \cdot 0.33\ C_6H_5CH_3$ | | | |
|---|---|---|---|
| | C | H | N |
| Calculated value; | 73.04 | 7.25 | 6.00 |
| Observed value; | 72.96 | 7.64 | 5.75 |

IR (KBR)cm$^{-1}$: 3420, 3340, 2952, 1721, 1642, 1605, 1595, 1536, 1451.

$^1$HNMR (CDCl$_3$) (δ, ppm): 0.99(s, 9H), 2.05–2.6(m, 4H), 2.71(d, 3H, J=1.1 Hz), 3.87(s, 2H), 4.05(t, 2H, J=6 Hz), 6.28(d, 1H, J=1.1 Hz), 6.49(d, 1H, J=3 Hz), 6.82–7.3(m, 6H), 7.83(s, 1H), 7.90 (brs, 1H), 8.3–8.5(m, 1H).

EXAMPLE 11

4-{2-[3-[1-(4-methylpentyl)indol-5-yl]isocrotonoyl amino]phenoxy}butyric acid (Compound 11)

0.41 g of compound 11 was obtained in a similar manner to those described in the Examples 1 and 2 using 2.33 g of ethyl 4-(2-aminophenoxy)butyrate and 1.49 g of 3-[1-(4-methylpentyl)indol-5-yl]isocrotonic acid obtained according to the procedures described in the Reference Examples 1–4.

Melting point: 100°–101° C.

| Elementary analysis (%): $C_{28}H_{34}N_2O_4$ | | | |
|---|---|---|---|
| | C | H | N |
| Calculated value; | 72.70 | 7.41 | 6.06 |
| Observed value; | 73.00 | 7.77 | 6.11 |

IR (KBr)cm$^{-1}$: 3420, 3330, 2928, 1720, 1633, 1615, 1596, 1525, 1453.

$^1$HNMR (CDCl$_3$) (δ, ppm): 0.86(d, 6H, J=6.4 Hz), 1.03–2.33(m, 7H), 2.52 (t, 2H, J=6.8 Hz), 2.70(d, 3H, J=1.1 Hz), 4.07(t, 4H, J=6.8 Hz), 6.31 (d, 1H, J=1.1 Hz), 6.50(d, 1H, J=2.9 Hz), 6.77–7.37(m, 6H), 7.77(s, 1H), 7.91(s, 1H), 8.29–8.56(m, 1H).

EXAMPLE 12

4-{2-[3-[1-(3-methy-2-butenyl)indol-5-yl]isocrotonoyl amino]phenoxy}butyric acid (Compound 12)

137 mg of compound 12 was obtained in a similar manner to those described in the Examples 1 and 2 using 332 mg of ethyl 4-(2-aminophenoxy)butyrate and 200 mg of 3-[1-(3-methyl-2-butenyl)indol-5-yl]isocrotonic acid obtained according to the procedures described in the Reference Examples 1–4.

Melting point: 137°–140° C.

| Elementary analysis (%): $C_{27}H_{30}N_2O_4$ | | | |
|---|---|---|---|
| | C | H | N |
| Calculated value; | 72.62 | 6.77 | 6.27 |
| Observed value; | 72.74 | 7.07 | 6.14 |

IR (KBr)cm$^{-1}$: 3450, 3310, 1723, 1631, 1612, 1594, 1539, 1452.

$^1$HNMR (CDCl$_3$) (δ, ppm): 1.76(d, 3H, J=1.1 Hz), 1.81(s, 3H), 2.07–2.67 (m, 4H), 2.71(d, 3H, J=1.1 Hz), 4.08(t, 2H, J=6 Hz), 4.67(d, 2H, J=6.8 Hz), 5.30–5.38(m, 1H), 6.32(d, 1H, J=1.1 Hz), 6.50(d, 1H, J=3 Hz), 6.82–7.37 (m, 7H), 7.78(s, 1H), 7.91–7.95(m, 1H), 8.23–8.50(m, 1H).

EXAMPLE 13

4-}2-[3-[1-(2-ethoxyethyl)indo-5-yl]iso-crotonoylamino]phenoxy}butyric acid (Compound 13)

0.72 g of compound 13 was obtained in a similar manner to those described in the Examples 1 and 2 using 1.96 g of ethyl 4-(2-aminophenoxy)butyrate and 1.20 g of 3-[1-(2-ethoxyethyl)indol-5-yl]isoceotonic acid obtained according to the procedures described in the Reference Examples 1–4.

Melting point: 108°-108.5° C.

| Elementary analysis (%): $C_{26}H_{30}N_2O_5$ | | | |
|---|---|---|---|
| | C | H | N |
| Calculated value; | 69.31 | 6.71 | 6.22 |
| Observed value; | 69.50 | 7.00 | 6.61 |

IR (KBr)cm$^{-1}$: 3420, 3364, 1718, 1641, 1603, 1598, 1533, 1487, 1453.

$^1$HNMR (CDCl$_3$) (δ, ppm): 1.14(t, 3H, J=6.9 Hz), 1.98-2.29(m, 2H), 2.55 (t, 2H, J=6 Hz), 2.70(d, 1H, J=1.1 Hz), 3.42(q, 2H, J=7.1 Hz), 3.72(t, 2H, J=6 Hz), 4.08(t, 2H, J=6 Hz), 4.26(t, 2H, J=6 Hz), 6.32(d, 1H, J=1.1 Hz), 6.50(d, 1H, J=4 Hz), 6.7-7.02(m, 3H), 7.17(d, 1H, J=3.1 Hz), 7.35 (s, 1H), 7.75(s, 1H), 7.92(s, 1H), 8.28-8.52(m, 1H).

EXAMPLE 14

4-{2-[3-[1-(2-methylpentyl)indol-5-yl]isocrotonoylamino]phenoxy}butyric acid (Compound 14)

0.56 g of compound 14 was obtained in a similar manner to those described in the Examples 1 and 2 using 1.56 g of ethyl 4-(2-aminophenoxy)butyrate and 1.0 g of 3-[1-(2-methylpentyl)indol-5-yl]isocrotonic acid obtained according to the procedures described in the Reference Examples 1-4.

Melting point: 136°-138° C.

| Elementary analysis (%): $C_{28}H_{34}N_2O_4$ | | | |
|---|---|---|---|
| | C | H | N |
| Calculated value; | 72.70 | 7.41 | 6.06 |
| Observed value; | 72.88 | 7.67 | 6.10 |

IR (KBr)cm$^{-1}$: 3450, 3320, 1721, 1633, 1609, 1592, 1537, 1453.

$^1$HNMR (CDCl$_3$) (δ, ppm): 0.85(d, 3H, J=6.4 Hz), 0.89(t, 3H, J=5.8 Hz), 1.1-1.7(m, 4H), 1.8-2.4(m, 3H), 2.53(t, 2H, J=6 Hz), 2.70(d, 3H, J=0.9 Hz), 3.78-4.12(m, 4H), 6.31(d, 1H, J=0.9 Hz), 6.50(d, 1H, J=3.1 Hz), 6.77-7.50(m, 6H), 7.78(s, 1H), 7.93(s, 1H), 8.3-8.6(m, 1H).

EXAMPLE 15

4-{2-[3-[1-(1-methylpropyl)indol-5-yl]isocrotonoylamino]-phenoxy}butyric acid (Compound 15)

1.21 g compound 15 was obtained in a similar manner to those described in the Examples 1 and 2 using 1.80 g of ethyl 4-(2-aminophenoxy)butyrate and 1.04 g of 3-[1-(1-methylpropyl)indol-5-yl]isocrotonic acid obtained according to the procedures described in the Reference Examples 1-4.

Melting point: 137°-140° C.

| Elementary analysis (%): $C_{26}H_{30}N_2O_4$ | | | |
|---|---|---|---|
| | C | H | N |
| Calculated value; | 71.87 | 6.96 | 6.45 |
| Observed value; | 71.90 | 7.21 | 6.20 |

IR (KBr)cm$^{-1}$: 3350, 2958, 1722, 1644, 1606, 1598, 1538, 1456.

$^1$HNMR (CDCl$_3$) (δ, ppm): 0.82(t, 3H, J=7.4 Hz), 1.50(d, 3H, J=6.8 Hz), 1.72-2.59(m, 6H), 2.71(d, 3H, J=1.1 Hz), 4.08(t, 2H, J=5.8 Hz), 4.36 (q, 2H, J=6.8 Hz), 6.32(d, 1H, J=1.1 Hz), 6.55(d, 1H, J=3.1 Hz), 6.79-7.01 (m, 3H), 7.18(d, 1H, J=3.1 Hz), 7.36(s, 2H), 7.79(s, 1H), 7.93(s, 1H, 8.3-8.55(m, 1H).

EXAMPLE 16

4-{2-[3-[1-(1-methylbutyl)indol-5-yl]isocrotonoylamino]phenoxy}butyric acid (Compound 16)

1.20 g of compound 16 was obtained in a similar manner to those described in the Examples 1 and 2 using 2.63 g of ethyl 4-(2-aminophenoxy)butyrate and 1.60 g of 3-[1-(1-methylbutyl)indol-5-yl]isocrotonic acid obtained according to the procedures described in the Reference Examples 1-4.

Melting point: 167°-168° C.

| Elementary analysis (%): $C_{27}H_{32}N_2O_4$ | | | |
|---|---|---|---|
| | C | H | N |
| Calculated value; | 72.30 | 7.19 | 6.25 |
| Observed value; | 72.55 | 7.48 | 6.24 |

IR (KBr)cm$^{-1}$: 3440, 3350, 1722, 1644, 1606, 1598, 1537, 1456.

$^1$HNMR (CDCl$_3$) (δ, ppm): 0.87(t, 3H, J=6.8 Hz), 1.09-1.34(m, 2H), 1.50(d, 3H, J=6.8 Hz), 1.70-2.65(m, 6H), 2.71(d, 3H, J=1.1 Hz), 4.08(t, 2H, J=6 Hz), 4.30-4.60(m, 1H), 6.32(d, 1H, J=1.1 Hz), 6.54(d, 1H, J=3.3 Hz), 6.76-7.12(m, 3H), 7.18(d, 1H, J=3.3 Hz), 7.36(s, 2H), 7.78(s, 1H), 7.94(s, 1H), 8.3-8.6(m, 1H).

EXAMPLE 17

4-{2-[3-[1-(1-methylpentyl)indol-5-yl]isocrotonoylamino]phenoxy}butyrate (Compound 17)

1.15 g of compound 17 was obtained in a similar manner to those described in the Examples 1 and 2 using 2.22 g of ethyl 4-(2-aminophenoxy)butyrate and 1.42 g of 3-[1-(1-methylpentyl)indol-5-yl]isocrotonic acid obtained according to the procedures described in the Reference Examples 1-4.

Melting point: 157°-159° C.

| Elementary analysis (%): $C_{28}H_{34}N_2O_4$ | | | |
|---|---|---|---|
| | C | H | N |
| Calculated value; | 72.70 | 7.41 | 6.06 |
| Observed value; | 72.87 | 7.69 | 6.10 |

IR (KBr)cm$^{-1}$: 3450, 3360, 1721, 1643, 1610, 1598, 1538, 1455.

$^1$HNMR (CDCl$_3$) (δ, ppm): 0.84(t, 3H, J=6.7 Hz), 1.03-1.35(m, 2H), 1.50 (d, 3H, J=6.8 Hz), 1.65-2.60(m, 6H), 2.73(d, 3H, J=1.1 Hz), 4.10(t, 2H, J=5.9 Hz), 4.2-4.6(m, 1H), 6.41(d, 1H, J=1.1 Hz), 6.56(d, 1H, J=3.3 Hz), 6.7-7.5(m, 6H), 7.81(s, 1H), 8.07(s, 1H) 8.42-8.53(m, 1H).

Example 18

4-{2-[3-[1-(1-ethylpentyl)indol-5-yl]isocrotonoyl amino]phenoxy}butyric acid (Compound 18)

1.11 g of compound 18 was obtained in a similar manner to those described in the Examples 1 and 2 using 2.18 g of ethyl 4-(2-aminophenoxy)butyrate and 1.47 g of 3-[1-(1-ethylpentyl)indol-5-yl]isocrotonic acid obtained according to the procedures described in the Reference Examples 1-4.

Melting point: 144°-149° C.

| Elementary analysis (%): $C_{29}H_{36}N_2O_4$ | | | |
|---|---|---|---|
| | C | H | N |
| Calculated value; | 73.08 | 7.61 | 5.88 |
| Observed value; | 72.74 | 7.48 | 6.06 |

IR (KBr)cm$^{-1}$: 3450, 3360, 1723, 1640, 1599, 1536, 1477.

$^1$HNMR (CDCl$_3$) (δ, ppm): 0.74(t, 3H, J=7.8 Hz), 0.80(t, 3H, J=5.8 Hz), 0.95-1.56(m, 4H), 1.7-2.4(m, 6H), 2.53(t, 2H, J=6.5 Hz), 2.71(d, 1H, J=1 Hz), 4.01-4.33(m, 3H), 6.30(d, 1H, J=1 HZ), 6.56 (d, 1H, J=3 Hz), 6.75-7.01(m, 3H), 7.13(d, 1H, J=3 Hz), 7.34(s, 2H), 7.78(s, 1H), 7.93(s, 1H), 8.3-8.6(m, 1H).

Example 19

4-{2-[3-[1-(1-propylbutyl)indol-5-yl]isocrotonoyl amino]phenoxy}butyric acid (Compound 19) and sodium salts (Compound 19 Na)

0.79 g of compound 19 was obtained in a similar manner to those described in the Examples 1 and 2 using 1.70 g of ethyl 4-(2-aminophenoxy)butyrate and 1.10 g of 3-[1-(1-propylbutyl)indol-5-yl]isocrotonic acid obtained according to the procedures described in the Reference Examples 1-4.

Compound 19 was dissolved in 5 ml of methanol and 0.95 equivalent sodium methoxide was added. After the solvent was evaporated, the resultant residue was triturated in isopropyl ether to give 0.81 g of amorphous compound 19 Na.

| (COMPOUND 19Na) Elementary analysis (%): $C_{29}H_{35}N_2O_4Na \cdot H_2O$ | | | |
|---|---|---|---|
| | C | H | N |
| Calculated value; | 67.42 | 7.22 | 5.42 |
| Observed value; | 67.54 | 7.27 | 5.16 |

IR (KBr)cm$^{-1}$: 3400, 2850, 1657, 1562, 1547.

Compound 19

$^1$HNMR (CDCl$_3$) (δ, ppm): 0.86 (brd, 6H, J=6.4 Hz), 0.97-1.39(m, 4H), 1.69-2.0(m, 4H), 2.02-2.28(m, 2H), 2.45-2.61(m, 2H), 2.70(d, 3H, J=1 Hz), 4.06(t, 2H, J=6.0 Hz), 4.12-4.28(m, 1H), 6.31(d, 1H, J=1 Hz), 6.55(d, 1H, J=3.3 Hz), 6.76-7.0(m, 3H), 7.13(d, 1H, J=3.3 Hz), 7.34 (brs, 2H), 7.77 (brs, 1H), 7.84 (brs, 1H), 7.97 (brs, 1H), 8.25-8.50(m, 1H).

Example 20

4-{2-[3-[1-(1-butylpentyl)indol-5-yl]isocrotonoyl amino]phenoxy}butyric acid (Compound 20) and sodium salts (Compound 20 Na)

Compound 20 was obtained in a similar manner to those described in the Examples 1 and 2 using 2.18 g of ethyl 4-(2-aminophenoxy)butyrate and 1.68 g of 3-[1-(1-butylpentyl)indol-5-yl]isocrotonic acid obtained according to the procedures described in the Reference Examples 1-4.

0.66 g of amorphous compound 20 Na was obtained in a similar manner to that of the Example 19.

| (COMPOUND 20Na) Elementary analysis (%): $C_{31}H_{39}N_2O_4Na$ | | | |
|---|---|---|---|
| | C | H | N |
| Calculated value; | 70.70 | 7.46 | 5.32 |
| Observed value; | 71.10 | 7.69 | 5.29 |

IR (KBr)cm$^{-1}$: 1660, 1600, 1452, 1249.

Compound 20

$^1$HNMR (CDCl$_3$) (δ, ppm): 0.80(t, 3H, J=6.4 Hz), 0.9-1.5(m, 8H), 1.65-2.35 (m, 6H), 2.54(t, 2H, J=6 Hz), 2.71(d, 3H, J=1 Hz), 4.0-4.3(m, 3H), 6.32(d, 1H, J=1 Hz), 6.56(d, 1H, J=3.3 Hz), 6.75-7.0(m, 3H), 7.14(d, 1H, J=3.3 Hz), 7.35(s, 2H), 7.79(s, 1H), 7.93(s, 1H), 8.2-8.6(m, 1H).

Example 21

4-{2-[3-[1-(1-methylethyl)butylindol-5-yl]isocrotonoyl amino]phenoxy}butyric acid (Compound 21)

0.93 g of compound 21 was obtained in a similar manner to those described in the Examples 1 and 2 using 2.20 g of ethyl 4-(2-aminophenoxy)butyrate and 1.50 g of 3-[1-(1-methylethyl)butylindol-5-yl]isocrotonic acid obtained according to the procedures described in the Reference Examples 1-4.

Melting point: 119°-123° C.

| Elementary analysis (%): $C_{29}H_{36}N_2O_4 \cdot 0.2\ H_2O$ | | | |
|---|---|---|---|
| | C | H | N |
| Calculated value; | 72.53 | 7.64 | 5.83 |
| Observed value; | 72.62 | 7.73 | 5.65 |

IR (KBr)cm$^{-1}$: 3344, 2868, 1725, 1714, 1596.

$^1$HNMR (CDCl$_3$) (δ, ppm): 0.70(d, 3H, J=6.8 Hz), 0.78-1.03(m, 5H), 1.02 (d, 3H, J=6.6 Hz), 1.83-2.08(m, 3H), 2.11-2.47(m, 2H), 2.48-2.65(m, 2H), 2.71 (brs, 3H), 3.8-4.1(m, 1H), 4.08(t, 2H, J=6.2 Hz), 5.8-6.3(m, 1H), 6.31(d, 1H, J=0.9 Hz), 6.55(d, 1H, J=3.2 Hz), 6.88-7.03(m, 3H), 7.12(d, 1H, J=3.2 Hz), 7.34 (brs, 2H), 7.78 (brs, 1H), 7.94 (brs, 1H), 8.3-8.55 (m, 1H).

Example 22

4-{2-[3-[1-(1,2-dimethylpentyl)indol-5-yl]isocrotonoyl amino]phenoxy}butyric acid (Compound 22)

0.45 g of compound 22 was obtained in a similar manner to those described in the Examples 1 and 2 using 0.75 g of ethyl 4-(2-aminophenoxy)butyrate and 0.50 g of 3-[1-(1,2-dimethylpentyl)indol-5-yl]isocrotonic acid obtained according the procedures described in the Reference Examples 1-4.

Melting point: 125°-130° C.

| Elementary analysis (%): $C_{29}H_{36}N_2O_4.0.2\ H_2O$ | | | |
|---|---|---|---|
| | C | H | N |
| Calculated value; | 72.53 | 7.64 | 5.83 |
| Observed value; | 72.52 | 7.67 | 5.70 |

IR (KBr)cm$^{-1}$: 3350, 2900, 1706, 1660, 1549.

$^1$HNMR (CDCl$_3$) (δ, ppm): 0.73(d, 3H, J=6.8 Hz), 0.92(d, 3H, J=6.8 Hz), 0.94-1.44(m, 5H), 1.49(dd, 3H, J=3.0 &U 6.9 Hz), 2.16-2.23(m, 2H), 2.47-2.63(m, 2H), 2.71(d, 3H, J=1.1 Hz), 4.08(t, 2H, J=6.0 Hz), 4.15-4.35 (m, 1H), 4.6-5.3(m, 1H), 6.31(d, 1H, J=1.3 Hz), 6.53(d, 1H, J=3.1 Hz), 6.88-6.98(m, 3H), 7.17(d, 1H, J=3.1 Hz), 7.34 (brs, 2H), 7.78 (s, 1H), 7.94(s, 1H), 8.35-8.48(m, 1H).

Example 23

4-{2-(1-cyclohexylmethylindol-5-yl)isocrotonoyl amino]phenoxy}butyric acid (Compound 23)

0.88 g of compound 23 was obtained in a similar manner to those described in Examples 1 and 2 using 1.39 g of ethyl 4-(2-aminophenoxy)butyrate and 0.93 g of 3-(1-cyclohexylmethylindol-5-yl)isocrotonic acid obtained according the procedures described in the Reference Examples 1-4.

Melting point: 129°-130° C.

| Elementary analysis (%): $C_{29}H_{34}N_2O_4.0.25\ H_2O$ | | | |
|---|---|---|---|
| | C | H | N |
| Calculated value; | 72.78 | 7.26 | 5.85 |
| Observed value; | 72.80 | 7.31 | 5.93 |

IR (KBr)cm$^{-1}$: 3430, 3330, 1720, 1633, 1602, 1597, 1532, 1451.

$^1$HNMR (CDCl$_3$) (δ, ppm): 0.8-2.4(m, 13H), 2.53(t, 2H, J=6.6 Hz), 2.70 (s, 3H), 3.91(d, 2H, J=7.3 Hz), 4.07(t, 2H, J=6.1 Hz), 6.30(s, 1H), 6.49 (d, 1H, J=2.9 Hz), 6.7-7.5(m, 6H), 7.77(s, 1H), 7.92(s, 1H) 8.3-8.6(m, 1H).

Example 24

4-{2-[3-(1-cyclohexylindol-5-yl)isocrotonoyl amino]phenoxy}butyric acid (Compound 24)

0.22 g of compound 24 was obtained in a similar manner to those described in the Examples 1 to 2 using 0.47 g of ethyl 4-(2-aminophenoxy)butyrate and 0.30 g of 3-(1-cyclohexylindol-5-yl)isocrotonic acid obtained according to the procedures described in the Reference Examples 1-4.

Melting point: 68°-75° C.

| Elementary analysis (%): $C_{28}H_{32}N_2O_4.0.3\ H_2O$ | | | |
|---|---|---|---|
| | C | H | N |
| Calculated value; | 72.17 | 7.05 | 6.01 |
| Observed value; | 72.21 | 7.16 | 5.85 |

| -continued Elementary analysis (%): $C_{28}H_{32}N_2O_4.0.3\ H_2O$ | | | |
|---|---|---|---|
| | C | H | N |
| value; | | | |

IR (KBr)cm$^{-1}$: 3350, 2854, 1702, 1661, 1542.

$^1$HNMR (CDCl$_3$) (δ, ppm): 1.20-2.21(m, 12H), 2.46-2.62(m, 2H), 2.69(d, 3H, J=1 Hz), 4.0-4.3(m, 1H), 4.06(t, 2H, J=5.8 Hz), 5.3-5.8(m, 1H), 6.31 (d, 1H, J=1 Hz), 6.51(d, 1H, J=3.2 Hz), 6.87-7.02(m, 3H), 7.21(d, 1H, J=3.2 Hz), 7.35 (brs, 2H), 7.77 (brs, 1H), 7.95 (brs, 1H), 8.3-8.5(m, 1H).

Example 25

4-{2-[3-[1-(2-cyclohexane-1-yl)indol-5-yl]isocrotonoyl amino]phenoxy}butyric acid (Compound 25)

0.87 g of compound 25 was obtained in a similar manner to those described in the Examples 1 and 2 using 1.46 g of ethyl 4-(2-aminophenoxy)butyrate and 0.93 g of 3-(2-cyclohexane-1-yl)indol-5-yl-isocrotonic acid obtained according the procedures described in the Reference Examples 1-4.

Melting point: 91°-93° C.

| Elementary analysis (%): $C_{28}H_{30}N_2O_4$ | | | |
|---|---|---|---|
| | C | H | N |
| Calculated value | 73.34 | 6.59 | 6.11 |
| Observed value | 73.46 | 6.47 | 6.17 |

IR (KBr)cm$^{-1}$: 3420, 3350, 2934, 1720, 1641, 1599, 1538, 1452.

$^1$HNMR (CDCl$_3$) (δ, ppm): 1.64-2.30(m, 8H), 2.54(t, 2H, J=6.5 Hz), 2.70 (d, 3H, J=1 Hz), 4.06(t, 2H, J=5.9 Hz), 4.85-5.10(m, 1H), 5.65-6.25(m, 2H), 6.30(d, 1H, J=1 Hz), 6.49(d, 1H, J=3.3 Hz), 6.78-7.03(m, 3H), 7.19-7.36(m, 3H), 7.78(s, 1H), 7.94(s, 1H), 8.3-8.55(m, 1H).

Example 26

4-{2-[3-(1-benzylindol-5-yl)isocrotonoyl amino]phenoxy}butyric acid (Compound 26)

131 mg of compound 26 was obtained in a similar manner to those described in the Examples 1 and 2 using 223 mg of ethyl 4-(2-aminophenoxy)butyrate and 291 mg of 3-(1-benzylindol-5-yl)isocrotonic acid obtained according to the procedures described in the Reference Examples 1-4.

Melting point: 162°-170° C.

| Elementary analysis (%): $C_{29}H_{28}N_2O_4$ | | | |
|---|---|---|---|
| | C | H | N |
| Calculated value | 74.34 | 6.02 | 5.98 |
| Observed value | 74.07 | 6.35 | 5.79 |

IR (KBr)cm$^{-1}$: 3322, 1721, 1634, 1611, 1596, 1537, 1454.

$^1$HNMR (CDCl$_3$+DMSO-d$_6$) (δ, ppm): 2.0-2.58(m, 4H), 2.70(d, 3H, J=1.1 Hz), 4.10(t, 2H, J=5.9 Hz), 5.33(s, 2H), 6.46(d, 1H, J=1.1 Hz), 6.57(d, 1H, J=3.3 Hz), 6.8-7.5(m, 11H), 7.33(s, 1H), 8.21(s, 1H), 8.39-8.47(m, 1H).

Example 27

4-{2-[3-(1-benzylindol-5-yl)-trans-2-acryloylamino]-phenoxy}butyric acid (Compound 27)

0.49 g of compound 27 was obtained in a similar manner to those described in the Examples 1 and 2 using 1.61 g of ethyl 4-(2-aminophenoxy)butyrate and 0.99 g of 3-(1-benzylindol-5-yl)acrylic acid obtained according to the procedures described in the Reference Examples 1-4.

Melting point: 123°-132° C.

| Elementary analysis (%): $C_{28}H_{26}N_2O_4$ | | | |
|---|---|---|---|
| | C | H | N |
| Calculated value | 73.99 | 5.77 | 6.16 |
| Observed value | 73.85 | 5.84 | 5.99 |

IR (KBr)cm$^{-1}$: 3450, 3350, 1708, 1655, 1603, 1594, 1530, 1455.

$^1$HNMR (CDCl$_3$) (δ, ppm): 2.10-2.63(m, 4H), 3.98(t, 2H, J=5.7 Hz), 5.23 (s, 2H), 6.50(d, 1H, J=3.1 Hz), 6.57-7.39(m, 12H), 7.68(s, 1H), 7.70(d, 1H, J=15.4 Hz), 8.15(s, 1H), 8.25-8.5(m, 1H).

Example 28

4-{2-[3-(1-benzylindol-5-yl)methacryloylamino]-phenoxy}butyric acid (Compound 28)

0.67 g of compound 28 was obtained in a similar manner to those described in the Examples 1 and 2 using 1.69 g of ethyl 4-(2-aminophenoxy)butyrate and 1.10 g of 3-(1-benzylindol-5-yl)methacrylic acid obtained according to the procedures described in the Reference Examples 1-4.

Melting point: 135°-137°]C.

| Elementary analysis (%): $C_{29}H_{28}N_2O_4$ | | | |
|---|---|---|---|
| | C | H | N |
| Calculated value | 74.34 | 6.02 | 5.98 |
| Observed value | 74.40 | 6.18 | 5.90 |

IR (KBr)cm$^{-1}$: 3425, 1738, 1647, 1604, 1532, 1454.

$^1$HNMR (CDCl$_3$) (δ, ppm): 2.05-2.35(m, 2H), 2.28(d, 3H, J=1.1 Hz), 2.56(t, 2H, J=6.6 Hz), 4.11(t, 2H, J=6.2 Hz), 5.29(s, 2H), 6.56(d, 1H, J=3.1 Hz), 6.7-7.4(m, 11H), 7.63(s, 1H), 7.71(s, 1H), 8.33(s, 1H), 8.43-8.54(m, 1H).

Example 29

4-{2-[3-(1-benzylindol-5-yl)-2-methyl isocrotonoylamino]phenoxy}butyric acid (Compound 29)

0.84 g of compound 29 was obtained in a similar manner to those described in the Examples 1 and 2 using 1.13 g of ethyl 4-(2-aminophenoxy)butyrate and 0.78 g of 3-(1-benzylindol-5-yl)-2-methylisocrotonic acid obtained according to the procedures described in the Reference Examples 1-4.

Melting point: 132.5°-134° C.

| Elementary analysis (%): $C_{30}H_{30}N_2O_4$ | | | |
|---|---|---|---|
| | C | H | N |
| Calculated value | 74.67 | 6.27 | 5.80 |
| Observed value | 74.93 | 6.46 | 5.72 |

IR (KBr)cm$^{-1}$:3420, 3380, 1730, 1626, 1597, 1520, 1484, 1455.

$^1$HNMR (CDCl$_3$) (δ, ppm): 1.90(d, 3H, J=1.1 Hz), 2.05-2.35(m, 2H), 2.23(s, 3H), 2.55(t, 2H, J=6.4 Hz), 4.10(t, 2H, J=6 Hz), 5.28(s, 2H), 6.53(d, 1H, J=3.3 Hz), 6.75-7.32(m, 11H), 7.47(s, 1H), 7.97(s, 1H), 8.3-8.6(m, 1H).

Example 30

4-{2-[3-[1-(4-fluorobenzyl)indol-5-yl]isocrotonoylamino]phenoxy}butyric acid (Compound 30)

334 mg of compound 30 was obtained in a similar manner to those described in the Examples 1 and 2 using 654 mg of ethyl 4-(2-aminophenoxy)butyrate and 454 mg of 3-[1-(4-fluorobenzyl)indol-5-yl]isocrotonic acid obtained according to the procedures described in the Reference Examples 1-4.

Melting point: 161°-163° C.

| Elementary analysis (%): $C_{29}H_{27}FN_2O_4$ | | | |
|---|---|---|---|
| | C | H | N |
| Calculated value | 71.59 | 5.59 | 5.76 |
| Observed value | 71.55 | 5.77 | 5.63 |

IR (KBr)cm$^{-1}$: 3420, 3320, 1722, 1635, 1610, 1597, 1538, 1455.

$^1$HNMR (DMSO-d$_6$) (δ, ppm): 1.9-2.2(m, 2H), 2.3-2.5(m, 2H), 2.61(s, 3H), 4.06(t, 2H, J=6 Hz), 5.42(s, 2H), 6.55(d, 1H, J=3 Hz), 6.65(s, 1H), 6.9-7.5(m, 10H), 7.80(d, 1H, J=1 Hz), 7.9-8.2(m, 1H), 8.90(s, 1H).

Example 31

4-{2-[3-[1-(2-methylbenzyl)indol-5-yl]isocrotonoylamino]phenoxy}butyric acid (Compound 31)

291 mg of compound 31 was obtained in a similar manner to those described in the Examples 1 and 2 using 521 mg of ethyl 4-(2-aminophenoxy)butyrate and 517 mg of 3-[1-(2-methylbenzyl)indol-5-yl]isocrotonic acid obtained according to the procedures described in the Reference Examples 1-4.

Melting point: 187°-190° C.

| Elementary analysis (%): $C_{30}H_{30}N_2O_4$ | | | |
|---|---|---|---|
| | C | H | N |
| Calculated value | 74.67 | 6.27 | 5.80 |
| Observed value | 74.76 | 6.63 | 5.71 |

IR (KBr)cm$^{-1}$: 3450, 3320, 1721, 1635, 1611, 1596, 1539, 1455.

$^1$HNMR (CDCl$_3$+DMSO-d$_6$) (δ, ppm): 2.32(s, 3H), 2.72(s, 3H), 4.11(t, 3H, J=6 Hz), 5.30(s, 3H), 6.43(d, 1H, J=0.7 Hz), 6.57(d, 1H, J=3 Hz), 6.64-7.5(m, 10H), 7.84(s, 1H), 8.08(brs, 1H), 8.30-8.56(m, 1H).

Example 32

4-{2-[3-[1-(3-methylbenzyl)indol-5-yl]isocrotonoylamino]phenoxy}butyric acid (Compound 32)

327 mg of compound 32 was obtained in a similar manner to those described in the Examples 1 and 2 using 566 mg of ethyl 4-(2-aminophenoxy)butyrate and 387 mg of 3-[1-(3-methylbenzyl)indole-5-yl]isocrotonic acid obtained according to the procedures described in the Reference Examples 1-4.

Melting point: 145°-150° C.

| Elementary analysis (%): $C_{30}H_{30}N_2O_4$ | | | |
|---|---|---|---|
| | C | H | N |
| Calculated value | 74.67 | 6.27 | 5.80 |
| Observed value | 75.06 | 6.64 | 5.70 |

IR (KBr)cm$^{-1}$: 3430, 3320, 1723, 1636, 1612, 1595, 1538, 1454.

$^1$HNMR (CDCl$_3$) ($\delta$, ppm): 2.0–2.25(m, 2H), 2.27(s, 3H), 2.51(t, 2H, J=6.4 Hz), 2.68(s, 3H), 4.05(t, 2H, J=6 Hz), 5.23(s, 2H), 6.29(s, 1H), 6.55(d, 1H, J=2.9 Hz), 6.68–7.40(m, 10H), 7.78(s, 1H), 7.92(s, 1H), 8.3–8.5(m, 1H)

Example 33

4-{2-[3-[1-(4-methylbenzyl)indol-5-yl]iso-crotonoylamino]phenoxy}butyric acid (Compound 33)

425 mg of compound 33 was obtained in a similar manner to those described in the Examples 1 and 2 using 777 mg of ethyl 4-(2-aminophenoxy)butyrate and 531 mg of 3-[1-(4-methylbenzyl)indol-5-yl]isocrotonic acid obtained according to the procedures described in the Reference Examples 1–4.

Melting point: 150.5°–154° C.

| Elementary analysis (%): $C_{30}H_{30}N_2O_4$ | | | |
|---|---|---|---|
| | C | H | N |
| Calculated value | 74.67 | 6.58 | 5.80 |
| Observed value | 75.06 | 6.58 | 5.72 |

IR (KBr)cm$^{-1}$: 3450, 3320, 1726, 1636, 1615, 1595, 1538, 1455.

$^1$HNMR (DMSO-d$_6$) ($\delta$, ppm): 1.85–2.60(m, 4H), 2.25(s, 3H), 2.61(s, 3H), 4.06(t, 2H, J=6 Hz), 5.37(s, 2H), 6.53(d, 1H, J=2.9 Hz), 6.66(s, 1H), 6.8–7.5(m, 10H), 7.81(s, 1H), 7.93–8.25(m, 1H), 8.89(s, 1H).

Example 34

4-{2-[3-[1-(4-trifluoromethylbenzyl)indol-5-yl]iso-crotonoylamino]phenoxy}butyric acid (Compound 34)

267 mg of compound 34 was obtained in a similar manner to those described in the Examples 1 and 2 using 563 mg of ethyl 4-(2-aminophenoxy)butyrate and 451 mg of 3-[1-(4-trifluoromethylbenzyl)indol-5-yl]isocrotonic acid obtained according to the procedures described in the Reference Examples 1–4.

Melting point: 134°–137° C.

| Elementary analysis (%): $C_{30}H_{27}F_3N_2O_4$ | | | |
|---|---|---|---|
| | C | H | N |
| Calculated value | 67.16 | 5.07 | 5.22 |
| Observed value | 67.40 | 5.18 | 5.08 |

IR (KBr)cm$^{-1}$: 3450, 3320, 1718, 1638, 1610, 1538, 1455.

$^1$HNMR (CDCl$_3$) ($\delta$, ppm): 1.98–2.35(m, 2H), 2.54(t, 2H, J=6 Hz), 2.70(s, 3H), 4.09(t, 2H, J=6.3 Hz), 5.36(s, 2H), 6.32(s, 1H), 6.61(d, 1H, J=2.6 Hz), 6.7–7.6(m, 10H), 7.82(s, 1H), 7.94(s, 1H), 8.3–8.55(m, 1H).

Example 35

4-{2-[3-[1-(4-methoxybenzyl)indol-5-yl]iso-crotonoylamino]phenoxy}butyric acid (Compound 35)

270 mg of compound 35 was obtained in a similar manner to those described in the Examples 1 and 2 using 615 mg of ethyl 4-(2-aminophenoxy)butyrate and 443 mg of 3-[1-(4-methoxybenzyl)indol-5-yl]isocrotonic acid obtained according to the procedures described in the Reference Examples 1–4.

Melting point: 123°–130° C.

| Elementary analysis (%): $C_{30}H_{30}N_2O_5$ | | | |
|---|---|---|---|
| | C | H | N |
| Calculated value | 72.27 | 6.07 | 5.62 |
| Observed value | 72.56 | 6.25 | 5.49 |

IR (KBr)cm$^{-1}$: 3450, 1718, 1646, 1605, 1533, 1456.

$^1$HNMR (CDCl$_3$) ($\delta$, ppm): 2.07–2.60(m, 4H), 2.69(d, 3H, J=1.1 Hz), 3.76(s, 3H), 4.07(t, 2H, J=6.1 Hz), 5.22(s, 2H), 6.29(d, 1H, J=1.1 Hz), 6.54(d, 1H, J=3.1 Hz), 6.76–7.33(m, 10H), 7.79(s, 1H), 7.90(s, 1H), 8.33–8.50(m, 1H).

Example 36

4-{2-[3-[1-(4-butylbenzyl)indol-5-yl]isocrotonoylamino]-phenoxy}butyric acid (Compound 36)

224 mg of compound 36 was obtained in a similar manner to those described in the Examples 1 and 2 using 513 mg of ethyl 4-(2-aminophenoxy)butyrate and 400 mg of 3-[1-(4-butylbenzyl)indol-5-yl]isocrotonic acid obtained according to the procedures described in the Reference Examples 1–4.

Melting point: 84°–87.5° C.

| Elementary analysis (%): $C_{33}H_{36}N_2O_4 \cdot 0.5(CH_3)_2CHOCH(CH_3)_2$ | | | |
|---|---|---|---|
| | C | H | N |
| Calculated value | 75.10 | 7.53 | 4.87 |
| Observed value | 75.28 | 7.69 | 4.87 |

IR (KBr)cm$^{-1}$: 3329, 2924, 1715, 1635, 1610, 1597, 1538, 1453.

$^1$HNMR (CDCl$_3$) ($\delta$, ppm): 0.90(t, 3H, J=6.8 Hz), 1.12–1.64(m, 4H), 2.06–2.21(m, 2H), 2.45–2.64(m, 4H), 2.69(d, 3H, J=1.1 Hz), 4.06(t, 2H, J=5.9 Hz), 5.24(s, 2H), 6.30(d, 1H, J=1.1 Hz), 6.55(d, 1H, J=3.3 Hz), 6.75–7.32(m, 10H), 7.78(s, 1H), 7.93(s, 1H), 8.22–8.50(m, 1H).

Example 37

4-{2-[3-[1-(4-tert-butylbenzyl)indol-5-yl]iso-crotonoylamino]phenoxy}butyric acid (Compound 37)

177 mg of compound 37 was obtained in a similar manner to those described in the Examples 1 and 2 using 513 mg of ethyl 4-(2-aminophenoxy)butyrate and 400 mg of 3-[1-(4-tert-butylbenzyl)indol-5-yl]isocrotonic acid obtained according to the procedures described in the Reference Examples 1–4.

Melting point: 103°–105° C.

| Elementary analysis (%): C<sub>33</sub>H<sub>36</sub>N<sub>2</sub>O<sub>4</sub>.0.75CCl<sub>4</sub>.H<sub>2</sub>O | | | |
|---|---|---|---|
| | C | H | N |
| Calculated value | 61.60 | 5.82 | 4.26 |
| Observed value | 61.60 | 5.50 | 4.15 |

IR (KBr)cm$^{-1}$: 3430, 3350, 2970, 1715, 1610, 1596, 1538, 1454.

$^1$HNMR (CDCl$_3$) (δ, ppm): 1.28(s, 9H), 2.03–2.60(m, 4H), 2.69(d, 3H, J=1 Hz), 4.07(t, 2H, J=5.8 Hz), 5.26(s, 2H), 6.31(d, 1H, J=1 Hz), 6.56(d, 1H, J=2.9 Hz), 6.86–7.36(m, 10H), 7.79(s, 1H), 7.93(brs, 1H), 8.24–8.51(m, 1H).

Example 38

4-{2-[3-[1-(α-methylbenzyl)indol-5-yl]iso-crotonoylamino]phenoxy}butyric acid (Compound 38)

111 mg of compound 38 was obtained in a similar manner to those described in the Examples 1 and 2 using 393 mg of ethyl 4-(2-aminophenoxy)butyrate and 268 mg of 3-[1-(α-methylbenzyl)indol-5-yl]isocrotonic acid obtained according to the procedures described in the Reference Examples 1–4.

Melting point: 50° C.

| Elementary analysis (%): C<sub>30</sub>H<sub>30</sub>N<sub>2</sub>O<sub>4</sub> | | | |
|---|---|---|---|
| | C | H | N |
| Calculated value | 74.67 | 6.27 | 5.80 |
| Observed value | 74.35 | 6.65 | 5.69 |

IR (KBr)cm$^{-1}$: 3410, 1712, 1598, 1519, 1450.

$^1$HNMR (CDCl$_3$) (δ, ppm): 1.91(d, 3H, J=7 Hz), 2.07–2.64(m, 4H), 2.68(s, 3H), 4.07(t, 2H, J=5.7 Hz), 5.64(q, 1H, J=7 Hz), 6.30(s, 1H), 6.58(d, 1H, J=2.6 Hz), 6.7–7.4(m, 11H), 7.78(s, 1H), 7.92(s, 1H), 8.2–8.55(m, 1H).

Example 39

4-{2-[N-methyl-N-[3-[1-(α-methylbenzyl)indol-5-yl]iso-crotonoyl]amino]phenoxy}butyric acid (Compound 39) and sodium salts (Compound 39Na)

Compound 39 was obtained in a similar manner to those described in the Examples 1 and 2 using 0.76 g of ethyl 4-[2-(N-methylamino)phenoxyl]butyrate and 0.48 g of 3-[1-(α-methylbenzyl)indol-5-yl]isocrotonic acid obtained according to the procedures described in the Reference Examples 1–4. 0.62 g of amorphous compound 39 Na was obtained in a similar manner to that of the Example 19, using Compound 20.

| (Compound 39 Na) Elementary analysis (%): C<sub>31</sub>H<sub>31</sub>N<sub>2</sub>O<sub>4</sub>Na.0.4H<sub>2</sub>O | | | |
|---|---|---|---|
| | C | H | N |
| Calculated value | 70.82 | 6.20 | 5.33 |
| Observed value | 70.96 | 6.51 | 5.08 |

Compound 39

IR (KBr)cm$^{-1}$: 2872, 1705, 1659, 1549.

$^1$HNMR (DMSO-d$_6$) (δ, ppm): 1.84(d, 3H, J=7.0 Hz), 1.91–2.20(m, 4H), 2.41(s, 3H), 3.16(s, 3H), 4.00(t, 2H, J=6.3 Hz), 5.71(q, 1H, J=7.0 Hz), 5.81(brs, 1H), 6.44(d, 1H, J=3.0 Hz), 6.76–7.32(m, 11H), 7.37(brs, 1H), 7.49(d, 1H, J=3.0 Hz).

Example 40

4-{2-[3-[1-(α-ethylbenzyl)indol-5-yl]iso-crotonoylamino]phenoxy}butyric acid (Compound 40)

73 mg of compound 40 was obtained in a similar manner to those described in Examples 1 and 2 using 465 mg of ethyl 4-(2-aminophenoxy)butyrate and 333 mg of 3-[1-(α-ethylbenzyl)indol-5-yl]isocrotonic acid obtained according to the procedures described in the Reference Examples 1–4.

Melting point: 153°–160° C.

| Elementary analysis (%): C<sub>31</sub>H<sub>32</sub>N<sub>2</sub>O<sub>4</sub>.0.1(CH<sub>3</sub>)<sub>2</sub>CHOCH(CH<sub>3</sub>)<sub>2</sub>.H<sub>2</sub>O | | | |
|---|---|---|---|
| | C | H | N |
| Calculated value | 73.32 | 6.80 | 5.34 |
| Observed value | 71.96 | 6.51 | 4.95 |

IR (KBr)cm$^{-1}$: 3450, 3360, 1718, 1605, 1597, 1538, 1455.

$^1$HNMR (CDCl$_3$) (δ, ppm): 0.95(t, 3H, J=7.3 Hz), 2.03–2.64(m, 6H), 2.68(s, 3H), 4.06(t, 2H, J=5.8 Hz), 5.32(t, 1H, J=7.3 Hz), 6.28(s, 1H), 6.5 6(d, 1H, J=3.1 Hz), 6.7–7.4(m, 11H), 7.77(s, 1H), 7.92(s, 1H), 8.25–8.5(m, 1H).

Example 41

4-{2-[3-[1-(α-propylbenzyl)indol-5-yl]iso-crotonoylamino]phenoxy}butyric acid (Compound 41)

484 mg of compound 41 was obtained in a similar manner to those described in Examples 1 and 2 using 835 mg of ethyl 4-(2-aminophenoxy)butyrate and 626 mg of 3-[1-(α-propylbenzyl)indol-5-yl]isocrotonic acid obtained according to the procedures described in the Reference Examples 1–4.

Melting point: 162°–165.5° C.

| Elementary analysis (%): C<sub>32</sub>H<sub>34</sub>N<sub>2</sub>O<sub>4</sub> | | | |
|---|---|---|---|
| | C | H | N |
| Calculated value | 75.27 | 6.71 | 5.49 |
| Observed value | 75.33 | 7.06 | 5.31 |

IR (KBr)cm$^{-1}$: 3425, 3350, 2970, 1716, 1635, 1605, 1597, 1538, 1455.

$^1$HNMR (CDCl$_3$) (δ, ppm): 0.95(t, 3H, J=6.6 Hz), 1.22–1.43(m, 2H), 2.06–2.72(m, 6H), 2.68(d, 3H, J=1 Hz), 4.06(t, 2H, J=6 HZ), 5.45(t, 1H, J=7.5 Hz), 6.28(d, 1H, J=1 Hz), 6.58(d, 1H, J=3.1 Hz), 6.7–7.4(m, 11H), 7.77(s, 1H), 7.89(s, 1H), 8.3–8.55(m, 1H).

Example 42

4-{2-[3-[1-(α-butylbenzyl)indol-5-yl]iso-crotonoylamino]phenoxy}butyric acid (Compound 42)

0.61 g of compound 42 was obtained in a similar manner to those described in the Examples 1 and 2 using 1.28 g of ethyl 4-(2-aminophenoxy)butyrate and 1.0 g of 3-[1-(α-butylbenzyl)indol-5-yl]isocrotonic acid obtained according to the procedures described in the Reference Examples 1–4.

Melting point: 129°–136° C.

| Elementary analysis (%): C<sub>33</sub>H<sub>36</sub>N<sub>2</sub>O<sub>4</sub> | | | |
|---|---|---|---|
| | C | H | N |
| Calculated value | 75.55 | 6.92 | 5.34 |

-continued

| Elementary analysis (%): C₃₃H₃₆N₂O₄ | | | |
|---|---|---|---|
| | C | H | N |
| Observed value | 75.25 | 6.90 | 5.34 |

IR (KBr)cm⁻¹: 3430, 3350, 1718, 1605, 1599, 1535, 1453.

¹HNMR (CDCl₃) (δ, ppm): 0.87(t, 3H, J=6 Hz), 1.1–1.6(m, 4H), 1.9–2.4(m, 4H), 2.51(t, 2H, J=6.1 Hz), 2.68(s, 3H), 4.05(t, 2H, J=6.1 Hz), 5.39(t, 1H, J=7.5 Hz), 6.27(s, 1H), 6.59(d, 1H, J=3.5 Hz), 6.7–7.4(m, 2H), 7.78(s, 1H), 7.92(s, 1H), 8.3–8.5(m, 1H).

Example 43

4-{2-[3-[1-(α-pentylbenzyl)indol-5-yl]isocrotonoylamino]phenoxy}butyric acid (Compound 43)

1.01 g of compound 43 was obtained in a similar manner to those described in the Examples 1 and 2 using 1.54 g of ethyl 4-(2-aminophenoxy)butyric acid and 1.30 g of 3-[1-(α-pentylbenzyl)indol-5-yl]isocrotonic acid obtained according to the procedures described in the Reference Examples 1–4.

Melting point: 68°–72° C.

| Elementary analysis (%): C₃₄H₃₈N₂O₄ | | | |
|---|---|---|---|
| | C | H | N |
| Calculated value | 75.81 | 7.11 | 5.20 |
| Observed value | 75.76 | 7.25 | 5.10 |

IR (KBr)cm⁻¹: 3430, 2920, 1703, 1600, 1535, 1515, 1449.

¹HNMR (CDCl₃) (δ, ppm): 0.7–1.0(m, 3H), 1.32(brs, 8H), 2.0–2.4(m, 4H), 2.50(t, 2H, J=5.7 Hz), 2.67(d, 3H, J=1 Hz), 4.03(t, 2H, J=5.5 Hz), 5.43(t, 1H, J=7.8 Hz), 6.27(d, 1H, J=1 Hz), 6.58(d, 1H, J=3.3 Hz), 6.7–7.05(m, 3H), 7.1–7.6(m, 8H), 7.76(s, 1H), 7.93(s, 1H), 8.25–8.55(m, 1H).

Example 44

4-{2-[3-[1-[α-(2-methylethyl)benzyl]indol-5-yl]isocrotonoylamino]phenoxy}butyric acid (Compound 44)

73 mg of compound 44 was obtained in a similar manner to those described in the Examples 1 and 2 using 135 mg of ethyl 4-(2-aminophenoxy)butyrate and 101 mg of 3-[1-[α-(2-methylethyl)benzyl]indol-5-yl]isocrotonic acid obtained according to the procedures described in the Reference Examples 1–4.

Melting point: 158°–161° C.

| Elementary analysis (%): C₃₂H₃₄N₂O₄ | | | |
|---|---|---|---|
| | C | H | N |
| Calculated value | 75.27 | 6.71 | 5.49 |
| Observed value | 75.30 | 6.77 | 5.35 |

IR (KBr)cm⁻¹: 3430, 3350, 1716, 1603, 1595, 1537, 1455.

¹HNMR (CDCl₃+DMSO-d₆) (δ, ppm): 0.96(d, 6H, J=6.4 Hz), 2.1–2.95(m, 5H), 2.70(s, 3H), 4.10(t, 2H, J=6 Hz), 4.94(d, 1H, J=11 Hz), 6.40(s, 1H), 6.59(d, 1H, J=3 Hz), 6.85–7.05(m, 3H), 7.1–7.5(m, 8H), 7.78(s, 1H), 8.13(s, 1H), 8.3–8.55(m, 1H).

Example 45

4-{2-[3-[1-(1,2,3,4-tetrahydro-1-naphthyl)indol-5-yl]isocrtonoylamino]phenoxy}butyric acid (Compound 45)

402 mg of compound 45 was obtained in a similar manner to those described in the Examples 1 and 2 using 830 mg of ethyl 4-(2-aminophenoxy)butyrate and 617 mg of 3-[1-(1,2,3,4-tetrahydro-1-naphthyl)indol-5-yl]isocrotonic acid according to the procedures described in the Reference Examples 1–4.

Melting point: 140°–146° C.

| Elementary analysis (%): C₃₂H₃₂N₂O₄ | | | |
|---|---|---|---|
| | C | H | N |
| Calculated value | 75.57 | 6.34 | 5.51 |
| Observed value | 75.29 | 6.64 | 5.64 |

IR (KBr)cm⁻¹: 3430, 3300, 1709, 1652, 1600, 1519, 1451.

¹HNMR (CDCl₃) (δ, ppm): 1.7–2.35(m, 6H), 2.54(t, 2H, J=6 HZ), 2.70(s, 3H), 2.8–3.05(m, 2H), 4.08(t, 2H, J=6.2 Hz), 5.63(t, 1H, J=6.5 Hz), 6.31(s, 1H), 6.48(d, 1H, J=3 Hz), 6.73–7.32(m, 6H), 7.80(s, 1H), 7.93(s, 1H), 8.3–8.8(m, 1H).

Example 46

4-{2-[3-(1-(α-cyclohexybenzyl)indol-5-yl]isocrotonoylamino]phenoxy}butyric acid (Compound 46)

227 mg of compound 46 was obtained in a similar manner to those described in the Examples 1 and 2 using 607 mg of ethyl 4-(2-aminophenoxy)butyrate and 508 mg of 3-[1-(α-cyclohexylbenzyl)indol-5-yl]isocrotonic acid obtained according to the procedures described in the Reference Examples 1–4.

Melting point: 152°–160° C.

| Elementary analysis (%): C₃₅H₃₈N₂O₄ | | | |
|---|---|---|---|
| | C | H | N |
| Calculated value | 76.34 | 6.96 | 5.09 |
| Observed value | 76.00 | 7.20 | 4.98 |

IR (KBr)cm⁻¹: 3430, 3350, 2932, 1715, 1606, 1596, 1537, 1453.

¹HNMR (CDCl₃) (δ, ppm): 0.7–2.4(m, 13H), 2.50(t, 2H, J=6 Hz), 2.67(s, 3H), 4.04(t, 2H, J=6 Hz), 5.02(d, 1H, J=11 Hz), 6.27(d, 1H, J=1 Hz), 6.55(d, 1H, J=3 Hz), 6.7–7.05(m, 3H), 7.1–7.45(m, 8H), 7.74(s, 1H), 7.91(s, 1H), 8.25–8.6(m, 1H).

EXAMPLE 47

4-{2-[3-(1-benzhydrylindol-5-yl)isocrotonoylamino]-4-chlorophenoxy}butyric acid (Compound 47)

268 mg of compound 47 was obtained in a similar manner to those described in the Examples 1 and 2 using 773 mg of ethyl 4-(2-amino-4-chlorophenoxy)butyrate and 551 mg of 3-(1-benzhydrylindol-5-yl)isocrotonic acid obtained according to the procedures described in the Reference Examples 1–4.

Melting point: 138°–140° C.

| Elementary analysis (%): $C_{35}H_{31}ClN_2O_4$ | | | |
| --- | --- | --- | --- |
|  | C | H | N |
| Calculated value | 72.59 | 5.40 | 4.84 |
| Observed value | 72.72 | 5.44 | 4.69 |

IR (KBr)cm$^{-1}$: 3430, 1744, 1515, 1415, 1211.
$^1$HNMR (CDCl$_3$) (δ, ppm), 2.06–2.28(m, 2H), 2.52(t, 2H, J=6 Hz), 2.65(d, 3H, J=1.1 Hz), 4.02(t, 2H, J=6 Hz), 6.30(d, 1H, J=1.1 Hz), 6.50(d, 1H, J=3.3 Hz), 6.62–7.36(m, 16H), 7.76(s, 1H), 7.93(s, 1H), 8.52(d, 2H, J=2 Hz).

Example 48

4-{2-[3-(1-benzhydrylindol-5-yl)isocrotonoylamino]-5-fluorophenoxy}butyric acid (Compound 48)

284 mg of compound 48 was obtained in a similar manner to those described in the Examples 1 and 2 using 723 mg of ethyl 4-(2-amino-4-fluorophenoxy)butyrate and 551 mg of 3-(1-benzhydrylindol-5-yl)isocrotronic acid obtained according to the procedures described in the Reference Examples 1–4.
Melting point: 174°–176° C.

| Elementary analysis (%): $C_{35}H_{31}FN_2O_4$ | | | |
| --- | --- | --- | --- |
|  | C | H | N |
| Calculated value | 74.72 | 5.55 | 4.98 |
| Observed value | 74.97 | 5.66 | 4.89 |

IR (KBr)cm$^{-1}$: 3400, 1716, 1598, 1529, 1216.
$^1$HNMR (DMSO-d$_6$) (δ, ppm): 1.92–2.07(m, 2H), 2.60(s, 3H), 4.07(t, 2H, J=6 Hz), 6.55(d, 1H, J=3.1 Hz), 6.62(d, 1H, J=0.7 Hz), 6.69–7.55(m, 1 16H), 7.81(s, 1H), 8.0(dd, 1H, J=6 and 8 Hz), 8.90(s, 1H).

Example 49

4-{2-[3-(1-benzhydrylindol-5-yl)isocrotonoylamino]-4-methylphenoxy}butyric acid (Compound 49)

305 mg of compound 49 was obtained in a similar manner to those described in the Examples 1 and 2 using 558 mg of ethyl 4-(2-amino-4-methylphenoxy)butyrate and 455 mg of 3-(1-benzhydrylindol-5-yl)isocrotonic acid obtained according to the procedures described in the Reference Examples 1–4.
Melting point: 112°–115° C.

| Elementary analysis (%): $C_{36}H_{34}N_2O_4$ | | | |
| --- | --- | --- | --- |
|  | C | H | N |
| Calculated value | 77.40 | 6.13 | 5.01 |
| Observed value | 77.17 | 6.43 | 5.40 |

IR (KBr)cm$^{-1}$: 3430, 3352, 1717, 1641, 1595, 1531, 1218.
$^1$HNMR (CDCl$_3$) (δ, ppm): 2.0–2.35(m, 2H), 2.29(s, 3H), 2.51(t, 2H, J=6.5 Hz), 2.69(s, 3H), 4.03(t, 2H, J=5.5 Hz), 6.27(s, 1H), 6.51(d, 1H, J=3 Hz), 6.74–6.87(m, 3H), 7.02–7.35(m, 13H), 7.87(s, 1H), 8.28(s, 1H).

Example 50

4-{2-[3-(1-benzhydrylindol-5-yl)isocrotonoylamino]-5-methylphenoxy}butyric acid (Compound 50)

406 mg of compound 50 was obtained in a similar manner to those described in the Examples 1 and 2 using 712 mg of ethyl 4-(2-amino-5-methylphenoxy)butyrate and 551 mg of 3-(1-benzhydrylindol-5-yl)isocrotonic acid obtained according to the procedures described in the Reference Examples 1–4.
Melting point: 176°–178° C.

| Elementary analysis (%): $C_{36}H_{34}N_2O_4$ | | | |
| --- | --- | --- | --- |
|  | C | H | N |
| Calculated value | 77.40 | 6.13 | 5.01 |
| Observed value | 77.14 | 6.19 | 4.87 |

IR (KBr)cm$^{-1}$: 3430, 3354, 1718, 1635, 1604, 1538.
$^1$HNMR (CDCl$_3$+DMSO-d$_6$) (δ, ppm): 2.05–2.35(m, 2H), 2.30(s, 3H), 2.49(t, 2H, J=7 Hz), 2.70(d, 3H, J=0.7 Hz), 4.07(t, 2H, J=6 Hz), 6.37(d, 1H, J=0.7 Hz), 6.52(d, 1H, J=3 Hz), 6.69(s, 1H), 6.82–7.36(m, 14H), 7.76(s, 1H), 7.96(s, 1H), 8.27(d, 1H, J=8 Hz).

Example 51

4-{2-[3-(1-benzhydrylindol-5-yl)isocrotonoylamino]-phenylthio}butyric acid (Compound 51)

0.37 g of amorphous compound 51 was obtained in a similar manner to those described in the Examples 1 and 2 using 1.30 g of ethyl 4-(2-aminophenylthio)butyrate and 1.0 g of 3-(1-benzhydrylindol-5-yl)isocrotonic acid obtained according to the procedures described in the Reference Examples 1–4.

| Elementary Analysis (%): $C_{35}H_{32}N_2O_3S$ | | | |
| --- | --- | --- | --- |
|  | C | H | N |
| Calculated value; | 74.97 | 5.75 | 5.00 |
| Observed value; | 74.81 | 6.09 | 4.67 |

IR (KBr)cm$^{-1}$: 3450, 3330, 1705, 1661, 1603, 1511, 1505, 1433.
$^1$ HNMR (CDCl$_3$) (δ, ppm): 1.78–2.0(m,2H), 2.43(t,2H, J=6.8 Hz), 2.70 (s,3H), 2.77(t,2H, J=6.8 Hz), 6.22(s,1H), 6.52 )d,1H, J=3 Hz), 6.81–8.54(m,19H).

EXAMPLE 52

4-{2-[3-[1-(2-methylbenzhydryl)indol-5-yl]iso-crotonoylamino[phenoxy}butyric acid (Compound 52)

0.65 g of compound 52 was obtained in a similar manner to those described in the Examples 1 and 2 using 1.64 g of ethyl 4-(2-aminophenoxy)butyrate and 1.40 g of 3-[1-(2-methylbenzhydryl)indol-5-yl]isocrotonic acid obtained according to the procedures described in the Reference Examples 1–4.
Melting point: 150°–151° C.

| Elementary Analysis (%): $C_{36}H_{34}N_2O_4$ | | | |
| --- | --- | --- | --- |
|  | C | H | N |
| Calculated value; | 77.40 | 6.13 | 5.01 |
| Observed value; | 77.46 | 6.48 | 4.74 |

IR (KBr)cm$^{-1}$: 3430, 1733, 1652, 1599, 1521, 1451.
$^1$ HNMR (CDCl$_3$) (δ, ppm): 1.85–2.2(m,2H), 2.06(s,3H), 2.41(t, 2H, J=6 Hz), 2.57(d,3H, J=1 Hz), 3.95(t,2H, J=6 Hz), 6.18(d,1H, J=1 Hz), 6.40(d,1H, J=3 Hz), 6.55-7.3(m, 15H), 7.68(s,1H), 7.81(s,1H), 8.2-8.45(m,1H).

EXAMPLE 53

4-{2-[3-[1-(4-methylbenzhydryl)indol-5-yl[iso-crotonoylamino]phenoxy}butyric acid (Compound 53)

0.79 g of compound 53 was obtained in a similar manner to those described in the Example 1 and 2 using 1.80 g of ethyl 4-(2-aminophenoxy)butyrate and 1.54 g of 3-[1-(4-methylbenzhydryl)indol-5-yl]isocrotonic acid obtained according to the procedures described in the Reference Examples 1–4.

Melting point: 157°–158° C.

| Elementary Analysis (%): $C_{36}H_{34}N_2O_4$ | | | |
|---|---|---|---|
| | C | H | N |
| Calculated value; | 77.40 | 6.13 | 5.01 |
| Observed value; | 77.28 | 6.18 | 4.87 |

IR (KBr)cm$^{-1}$: 3430, 3330, 1733, 1648, 1601, 1522, 1477.

$^1$HNMR (CDCl$_3$) (δ, ppm): 2.08-2.65(m,4H), 2.33(s,3H), 2.67(s,3H), 4.06 (t,2H, J=6 Hz), 6.28(s,1H), 6.50(d,1H, J=3.3 Hz), 6.76-7.34(m,15H), 7.79(s,1H), 7.93(s,1H), 8.3-8.5(m,1H).

EXAMPLE 54

4-{2-[3-[1-(4,4′-dimethylbenzhydryl)indol-5-yl]iso-crotonoylamino]phenoxy}butyric acid (Compound 54)

0.50 g of compound 54 was obtained in a similar manner to those described in the Examples 1 and 2 using 1.96 g of ethyl 4-(2-aminophenoxy)butyrate and 1.74 g of 3-[1-(4,4′-dimethylbenzhydryl)indol-5-yl]isocrotonic acid obtained according to the procedures described in the Reference Examples 1–4.

Melting point: 139°–141° C.

| Elementary Analysis (%): $C_{37}H_{36}N_2O_4.0.25\ H_2O_4$ | | | |
|---|---|---|---|
| | C | H | N |
| Calculated value; | 76.99 | 6.37 | 4.85 |
| Observed value; | 77.11 | 6.36 | 4.62 |

IR (KBr)cm$^{-1}$: 3430, 3304, 1720, 1632, 1610, 1594, 1528, 1475.

$^1$HNMR (CDCl$_3$) (δ, ppm): 2.0-2.6(m,4H), 2.33(s,6H), 2.68(s,3H), 4.03 (t,2H, J=6 Hz), 6.28(s,1H), 6.48(d,1H, J=3 Hz), 6,6-7.25(m,14H), 7.77 (s,1H), 7.90(s,1H), 8.3-8.5(m,1H).

EXAMPLE 55

4-{2-[3-[1-(10,11-dihydrodibenzo[a,d]cyclohepten-5-yl)indol-5-yl]isocrotonoylamino]phenoxy}butyric acid (Compound 55)

200 mg of compound 55 was obtained in a similar manner to those described in the Examples 1 and 2 using 424 mg of ethyl 4-(2-aminophenoxy)butyrate and 376 mg of 3-[1-(10,11-dihydrobenzo[a,d]cyclohepten-5-yl)indol-5-yl]isocrotonic acid obtained according to the procedures described in the Reference Examples 1–4.

Melting point: 227°–230° C.

| Elementary Analysis (%): $C_{37}H_{34}N_2O_4$ | | | |
|---|---|---|---|
| | C | H | N |
| Calculated value; | 77.87 | 6.01 | 4.91 |
| Observed value; | 77.92 | 6.19 | 4.82 |

IR (KRr)cm$^{-1}$: 3374, 1727, 1657, 1599, 1538, 1455, 1444.

$^1$HNMR (CDCl$_3$+DMSO-d$_6$) (δ, ppm): 2.06-3.25(m,8H), 2.67(s,3H), 4.10 (t,2H, J=5.5 Hz), 6.31(s,2H), 6.46 )d, 1H, J=3 Hz), 6.7-7.55(m,14H), 7.77(s,1H), 8.03(s,1H), 8.35-8.55(m,1H)

EXAMPLE 56

4-{2-[3-[1-3-methylbenzhydryl)indol-5-yl]iso-crotonoylamino]phenoxy}butyric acid (Compound 56)

0.52 g of compound 56 was obtained in a similar manner to those described in the Examples 1 and 2 using 1.17 g of ethyl 4-(2-aminophenoxy)butyrate and 1.0 g of 3-[1-(3-methylbenzhydryl)indol-5-yl]isocrotonic acid obtained according to the procedures described in the Reference Examples 1–4.

Melting point: 116°–120° C.

| Elementary Analysis (%): $C_{36}H_{34}N_2O_4$ | | | |
|---|---|---|---|
| | C | H | N |
| Calculated value; | 77.40 | 6.13 | 5.01 |
| Observed value; | 77.78 | 6.29 | 4.67 |

IR (KBr)cm$^{-1}$: 3450, 1731, 1607, 1453.

$^1$HNMR (CDCl$_3$) (δ, ppm): 2.05-2.75 )m,4H), 2.28(s,3H), 2.67(d,3H, J=1 Hz), 4.05(t,2H, J=5.5 Hz), 6.28(d, 1H, J=1.5 Hz), 6.50(d, 1H, J=3 Hz), 6.68-7.40(m,16H), 7.78(s,1H), 7.92(s,1H), 8.25-8.50(m,1H).

EXAMPLE 57

4-{2-[3-[1-(4-fluorobenzhydryl)indol-5-yl]iso-crotonoylamino]phenoxy}butyric acid (Compound 57)

0.6 g of compound 57 was obtained in a similar manner to those described in the Examples 1 and 2 using 0.91 g of ethyl 4-(2-aminophenoxy)butyrate and 0.79 g of 3-[1-(4-fluorobenzhydryl)indol-5-yl]isocrotonic acid obtained according to the procedures described in the Reference Examples 1–4.

Melting point: 154.5°–155.5° C.

| Elementary Analysis (%): $C_{35}H_{31}FN_2O_4$ | | | |
|---|---|---|---|
| | C | H | N |
| Calculated value; | 74.72 | 5.55 | 4.98 |
| Observed value; | 74.52 | 5.71 | 4.83 |

IR(KBr)cm$^{-1}$: 3450, 1714, 1599, 1518, 1452.

$^1$HNMR (CDCl$_3$) (δ, ppm): 2.05-2.35(m, 2H), 2.40-2.70(m,2H), 2.68(d,3 H, J=1 Hz), 4.07(t,2H, J=6 Hz), 6.25(s,1H), 6.53(d,1H, J=3 Hz), 6.74-7.33(m,16H), 7.79(d,1H, J=1 Hz), 7.90(s,1H), 8.30-8.50(m,1H).

EXAMPLE 58

4-{2-[3-[1-(2-fluorobenzhydryl)indol-5-yl]iso-crotonoylamino]phenoxy}butyric acid (Compound 58)

0.61 g of compound 58 was obtained in a similar manner to those described in the Examples 1 and 2 using 0.99 g of ethyl 4-(2-aminophenoxy)butyrate and 0.86 g of 3-[1-(2-fluorobenzhydryl)indol-5-yl]isocrotonic acid obtained according to the procedures described in the Reference Examples 1–4.

Melting point: 164.5°–165° C.

| Elementary Analysis (%): $C_{35}H_{31}FN_2O_4$ | | | |
|---|---|---|---|
| | C | H | N |
| Calculated value; | 74.72 | 5.55 | 4.98 |
| Observed value; | 74.57 | 5.73 | 4.86 |

IR (KBr)cm$^{-1}$: 3420, 1745, 1602, 1591, 1530, 1451.
$^1$HNMR (CDCl$_3$) (δ, ppm): 1.98–2.30) (m,2H), 2.35–2.60(m,2H), 2.71(d,1H, J=1 Hz), 4.10(t,2H, J=6 Hz), 6.40(d,1H, J=1 Hz), 6.54(d,1H, J=4 Hz), 6.65–7.38(m,16H), 7.83(d,1H, J=1 Hz), 8.06(d,1H, J=1 Hz), 8.33–8.52(m,1H).

Example 59

4-{2-[3-[1-(4,4'-difluorobenzhydryl)indol-5-yl]iso-crotonoylamino]phenoxy}butyric acid (Compound 59)

0.31 g of compound 59 was obtained in a similar manner to those described in the Examples 1 and 2 using 1.11 g of ethyl 4-(2-aminophenoxy)butyrate and 1.0 g of 3-[1-(4,4'-difluorobenzhydryl)indol-5-yl]isocrotonic acid obtained according to the procedures described in the Reference Examples 1–4.

Melting point: 148.5°–149° C.

| Elementary Analysis (%): $C_{35}H_{30}F_2N_2O_4$ | | | |
|---|---|---|---|
| | C | H | N |
| Calculated value; | 72.40 | 5.21 | 4.82 |
| Observed value; | 72.23 | 5.30 | 4.66 |

IR (KBr)cm$^{-1}$: 3420, 3340, 1731, 1602, 1510, 1449.
$^1$HNMR (CDCl$_3$) (δ, ppm): 2.02–2.30(m, 2H), 2.40–2.75(m, 2H), 2.67s, 3H), 4.06t, 2H, J=6 Hz), 6.28(s, 1H), 6.52(d, 1H, J=3.5 Hz), 6.77–7.38(m, 15H), 7.78(s, 1H), 7.92(s, 1H), 8.40(br, 1H).

Example 60

4-{2-[3-[1-(4,4-dimethoxybenzhydryl)indol-5-yl]iso-crotonoylamino]phenoxy}butyric acid (Compound 60)

119 mg of compound 60 was obtained in a similar manner to those described in the Examples 1 and 2 using 249 mg of ethyl 4-(2-aminophenoxy)butyrate and 239 mg of 3-[1-(4,4'-dimethoxybenzhydryl)indol-5-yl]iso-crotonic acid obtained according to the procedures described in the Reference Examples 1–4.

Melting point: 147°–148° C.

| Elementary Analysis (%): $C_{37}H_{36}N_2O_6$ | | | |
|---|---|---|---|
| | C | H | N |
| Calculated value; | 73.49 | 6.00 | 4.63 |
| Observed value; | 73.43 | 6.20 | 4.46 |

IR (KBr)cm$^{-1}$: 3450, 1715, 1599, 1511, 1454, 1250.
$^1$HNMR (CDCl$_3$) (δ, ppm): 2.01–2.32(m, 2H), 2.40–2.75(m, 2H), 2.68(s, 3 H), 3.77(s, 6H), 4.05(t, 2H, J=6 Hz), 6.24(s, 1H), 6.43(d, 1H, J=3 Hz), 6.60–7.40(m, 15H), 7.87(s, 1H), 8.40(br, 1H).

Example 61

4-{2-[3-[1-(4,4'-dichlorobenzhydryl)indol-5-yl]iso-crotonoylamino]phenoxy}butyric acid (Compound 61)

217 mg of compound 61 was obtained in a similar manner to those described in the Examples 1 and 2 using 438 mg of ethyl 4-(2-aminophenoxy)butyrate and 429 mg of 3-[1-(4,4'-dichlorobenzhydryl)indol-5-yl]isocrotonic acid obtained according to the procedures described in the Reference Examples 1–4.

Melting point: 181°–182° C.

| Elementary Analysis (%): $C_{35}H_{30}Cl_2N_2O_4$ | | | |
|---|---|---|---|
| | C | H | N |
| Calculated value; | 68.52 | 4.93 | 4.57 |
| Observed value; | 68.77 | 4.89 | 4.51 |

IR (Kbr)cm$^{-1}$: 3400, 1708, 1599, 1513, 1450.
$^1$HNMR (CDCl$_3$) (δ, ppm): 2.02–2.30(m, 2H), 2.40–2.70(m, 2H), 2.66(s, 3H), 4.06(t, 2H, J=5.5 Hz), 6.29(d, 1H, J=1 Hz), 6.53(d, 1H, J=3.3 Hz), 6.72–7.35(m, 15H), 7.77(s, 1H), 7.94(s, 1H), 8.25–8.50(m, 1H).

Example 62

4-{-2-[3-[1-(4,4'-difluorobenzhydryl)indol-5-yl]iso-crotonoylamino]-5-fluorophenoxy}butyric acid (Compound 62)

169 mg of compound 62 was obtained in a similar manner to those described in the Examples 1 and 2 using 359 mg of ethyl 4-(2-amino-5-fluorophenoxy)butyrate and 300 mg of 3-[1-(4,4'-difluorobenzhydryl)indol-5-yl]isocrotonic acid obtained according to the procedures described in the Reference Examples 1–4.

Melting point: 137°–141° C.

| Elementary Analysis (%): $C_{35}H_{29}F_3N_2O_4$ | | | |
|---|---|---|---|
| | C | H | N |
| Calculated value; | 70.22 | 4.88 | 4.68 |
| Observed value; | 70.47 | 4.78 | 4.30 |

IR (KBr)cm$^{-1}$: 3420, 3340, 1731, 1605, 1530, 1510.
$^1$HNMR (CDCl$_3$) (δ, ppm): 2.03–2.36(m, 2H), 2.40–2.60(m, 2H), 2.64(s, 3 H), 4.03(t, 2H, J=6 Hz), 6.20–7.35(m, 16H), 7.65–7.82(m, 2H), 8.30(br. 1H).

Example 63

4-{2-[3-[1-[phenyl-(2-pyridyl)methyl]indol-5-yl]isocrotonoylamino]phenoxy}butyric acid (Compound 63)

399 mg of compound 63 was obtained in a similar manner to those described in the Examples 1 and 2 using 804 mg of ethyl 4-(2-aminophenoxy)butyrate and 715 mg of 3-{1-[phenyl-(2-pyridyl)methyl]indol-5-yl}isocrotonic acid obtained according to the procedures described in the Reference Examples 1-4.

Melting point: 186.5°-188° C.

| Elementary Analysis (%): $C_{34}H_{31}N_3O_4$ | | | |
|---|---|---|---|
| | C | H | N |
| Calculated value; | 74.84 | 5.73 | 7.70 |
| Observed value; | 74.53 | 5.79 | 7.65 |

IR (KBr) cm$^{-1}$: 3430, 3314, 1732, 1534, 1454.

$^1$HNMR (DMSO-d$_6$) (δ, ppm): 185-225(m, 2H), 2.30-2.70(m, 2H), 2.61(s, 3H), 4.06(t, 2H, J=6 Hz), 6.54(d, 1H, J=3 Hz), 6.66(s, 1H, 675-790 (m, 15H), 8.12(dd, 1H, J=1 and 9 Hz), 8.61(dd, 1H, J=1 and 3.7 Hz), 8.89 (s, 1H).

Example 64

4-{2-[3-[1-(α, 2-dimethylbenzyl)indol-5-yl]isocrotonoylamino]phenoxy}butyric acid (Compound 64)

353 mg of compound 64 was obtained in a similar manner to those described in the Examples 1 and 2 using 573 mg of ethyl 4-(2-aminophenoxy)butyrate and 410 mg of 3-[1-(α, 2-dimethylbenzyl)indol-5-yl]isocrotonic acid obtained according to the procedures described in the Reference Examples 1-4

Melting point: 148°-152° C.

| Elementary Analysis (%): $C_{31}H_{32}N_2O_4$ | | | |
|---|---|---|---|
| | C | H | N |
| Calculated value; | 74.98 | 6.50 | 5.64 |
| Observed value; | 74.87 | 6.78 | 5.35 |

IR (KBr) cm$^{-1}$: 3430, 1703, 1600, 1471.

$^1$HNMR (CDCl$_3$) (δ, ppm): 184(d, 3H, J=6.8 Hz), 2.03-2.30(m, 2H), 2.23 (s, 3H), 2.40-2.75(m, 2H), 2.67 (d, 3H, J=1 Hz), 4.05 (t, 2H, J=6 Hz), 575 (q, 1H, J=6.8 Hz), 6.28(d 1H, J=1 Hz), 6.52(d, 1H, J=3.3 Hz), 6.70-7.40(m, 10H), 7.77(d, 1H, J=1 Hz), 7.90(s, 1H), 8.40(br, 1H.

Example 65

4-{2-[3-(1-benzhydrylindol-5-yl)isocrotonoylamino]-6-fluorophenoxy}butyric acid (Compound 65)

337 mg of compound 65 was obtained in a similar manner to those described in the Examples 1 and 2 using 723 mg of ethyl 4-(6-amino2-fluorophenoxy) butyrate and 551 mg of 3-(1-benzhydrylindol-5-yl) isocrotonic acid obtained according to the procedures described in the Reference Examples 1-4.

Melting point: 179°-180° C.

| Elementary Analysis (%): $C_{35}H_{31}FN_2O_4$ | | | |
|---|---|---|---|
| | C | H | N |
| Calculated value; | 74.72 | 5.55 | 4.98 |
| Observed value; | 74.57 | 5.57 | 4.87 |

IR (KBr) cm$^{-1}$: 3450, 3300, 1716, 1597, 1474, 1451.

$^1$HNMR (CDCl$_3$) (δ, ppm): 1.95-2.30(m, 2H), 2.40-2.70(m, 2H), 2.71(s, 3H), 4.17(t, 2H, J=6 Hz), 6.45-7.45(m, 18H), 7.84(d, 1H, J=1 Hz), 8.23-8.42(m, 2H).

Example 66

4-{2-[3-(1-benzhydrylindol-5-isocrotonoylamino]-4-fluorophenoxy}butyric acid (Compound 66)

340 mg of compound 66 was obtained in a similar manner to those described in the Examples 1 and 2 using 723 mg of ethyl 4-(2-amino-4-fluorophenoxy(butyrate and 551 mg of 3-(1-benzhydrylindol-5-yl) isocrotonic acid obtained according to the procedure described in the Reference Examples 1-4.

Melting point: 193.5°-195° C.

| Elementary Analysis (%): $C_{35}H_{31}FN_2O_4$ | | | |
|---|---|---|---|
| | C | H | N |
| Calculated value; | 74.72 | 5.55 | 4.98 |
| Observed value; | 74.38 | 5.65 | 4.80 |

IR (KBr) cm$^{-1}$: 3430, 3300, 1725, 1609, 1516, 1439.

$^1$HNMR (DMSO-d$_6$) (δ, ppm): 1.83-2.20(m, 2H), 2.33-2.60(m, 2H), 2.62(s, 3H), 4.05(t, 2H, J=5.8 Hz), 6.55(d, 1H, J=3.3 Hz), 6.75-7.50(m, 16H, 7.84(s, 1H), 8.09(dd, 1H, J=3 and 12.5 Hz), 8.99(s, 1H).

Example 67

4-{2-[3-1-(1-propylbutyl)indol-5-yl]isocrotonoylamino]-5-fluorophenoxy}butyric acid (Compound 67)

0.30 g compound 67 was obtained in a similar manner of those described in the Examples 1 and 2 using 0.65 g of ethyl 4-(2-amino-5-fluorophenoxy)butyrate and 0.52 g of 3-[1-(1propylbutyl)indol-5yl]isocrotonic acid obtained according to the procedures described in the References Examples 1-4.

Melting point: 140°-143° C.

| Elementary Analysis (%): $C_{29}H_{35}FN_2O_4 \cdot 0.2\ C_2H_5OH$ | | | |
|---|---|---|---|
| | C | H | N |
| Calculated value; | 70.09 | 7.24 | 5.56 |
| Observed value; | 70.21 | 7.59 | 5.24 |

IR (KBr) cm$^{-1}$: 3320, 2870, 1732, 1651, 1545, 1526, 1331.

$^1$HNMR (CDCl$_3$) (δ, ppm): 0.68-0.96 m, 6H), 1.0-1.24 (m, 4H), 1.60-199 (m, 4H), 2.03-2.30(m, 2H), 2.46-2.68 m, 2H), 2.68 (s, 3H, 4.04(t, 2H, J=5.8 Hz), 4.08-4.28(m, 1H), 6.29 s, 1H), 6.43-6.90(m, 1H), 6.53(s, 1H, 6.54 d, 1H, J=3.1 Hz), 6.58(d, 1H J=9.2 Hz), 7.13(d, 1H, J=3.1 Hz), 7.33(brs, 2H), 7.76(s, 1H), 7.81(s, 1H), 8.27-8.40(m, 1H).

Example 68

4-{2-[3-[1-(1-ethylbutyl)indol-5- yl]isocrotonoylamino]phenoxy}butyric acid (Compound 68).

0.30 g of compound 68 was obtained in a similar manner to those described in the Examples 1 and 2 using 0.81 g of ethyl 4-(2- aminophenoxy)butyrate and 0.52 g of 3-[1-(1-ethylbutyl)indol-5-yl]isocrotonic acid obtained according to the procedures described in Reference Examples 1-4.

Melting point: 137°-140° C.

| Elementary Analysis (%): $C_{28}H_{34}N_2O_4.0.3\ C_2H_5OH$ | | | |
|---|---|---|---|
| | C | H | N |
| Calculated value; | 72.11 | 7.57 | 5.88 |
| Observed value; | 72.14 | 7.87 | 5.84 |

IR (KBr) cm$^{-1}$: 3354, 2870, 1716, 1645, 1595, 1332.
$^1$HNMR (CDCl$_3$) (δ, ppm): 0.76(t, 3H, J=7.1 Hz), 0.84(t, 3H, J=7.1 Hz), 1.0-1.35(m, 2H), 1.85(q, 4H, J=7.1 Hz), 2.0-2.36(m, 2H), 2.43-2.64(m, 2H), 2.73(s, 3H), 4.0-4.28(m, 2H), 4.12(t, 2H, J=6.1 Hz), 6.43(d, 1H, J=1.1 Hz), 6.57(d, 1H, J=3.3 Hz), 6.85-6.98(m, 2H), 7.16(d, 1H, J=3.3 Hz), 7.30-7.42(m, 4H), 7.81(s, 1H), 814(s, 1H), 835-8.52(m, 2H).

Example 69

4-{2-[3-[1-(1-propylpentyl)indol-5-yl]isocrotonoylamino]phenoxy}butyric acid (Compound 69) and sodium salts (Compound 69 Na)

Compound 69 was obtained in a similar manner to those described in the Examples 1 and 2 using 1.10 g of ethyl 4-(2-aminophenoxy)butyrate and 0.76 g of 3-[1-(1-propylpentyl)indol-5-yl]isocrotonic acid obtained according to the procedures described in the Reference Examples 1-4.

0.50 g of amorphous-like compound 69 Na was obtained in a similar manner to that of the Example 19.

| Elementary Analysis (%): $C_{30}H_{37}N_2O_4Na.H_2O$ | | | |
|---|---|---|---|
| | C | H | N |
| Calculated value; | 67.91 | 7.41 | 5.28 |
| Observed value; | 67.99 | 7.73 | 5.08 |

IR (KBr) cm$^{-1}$: 3422, 2932, 1712, 1664, 1518, 1328.
$^1$HNMR (CDCl$_3$) (δ, ppm): 0.68-0.94(m, 6H), 0.98-1.33(m, 6H), 1.70-1.99 (m, 4H), 2.05-2.29(m, 2H), 2.54(t, 2H, J=6.6 Hz), 2.71(d, 3H, J=1 Hz), 4.08(t, 2H, J=6.2 Hz), 4.05-4.40(m, 1H), 6.31(d, 1H, J=2 Hz), 6.55(d, 1H, J=3.2 Hz), 6.70-6.98 m, 3H), 7.14(d, 1H, J=3.2 Hz), 7.35(s, 2H), 7.78(s, 1H), 7.94 s, 1H), 8.40-8.81(m, 1H).

Example 70

4-{2-[3-[1-(1-pentylhexyl)indol-5-isocrotonoylamino]phenoxy}butyric acid (Compound 70) and sodium salts (Compound 70 Na)

Compound 70 was obtained in a similar manner to those described in the Examples 1 and 2 using 0.72 g of ethyl 4-(2-aminophenoxy)butyrate and 0.57 g of 3-[1-(1-pentylhexyl)indol-5-]isocrontonic acid obtained according to the procedures described Reference Examples 1-4.

0.39 g of amorphous-like compound 70 Na was obtained in a similar manner to that of Example 19.

| (Compound 70 Na) Elementary Analysis (%): $C_{33}H_{43}N_2O_4Na.H_2O$ | | | |
|---|---|---|---|
| | C | H | N |
| Calculated value; | 69.21 | 7.92 | 4.89 |
| Observed value; | 69.06 | 8.21 | 4.69 |

Compound 70

IR (KBr) cm$^{-1}$: 3426, 2930, 1711, 1664, 1600, 1328.
$^1$HNMR (CDCl$_3$) (δ, ppm): 0.73-0.93(m, 6H), 1.0-1.29(m, 12H), 1.69-196 (m, 4H), 2.08-2.30(m, 2H), 2.48-2.66(m, 2H), 2.71(s, 3H), 4.08(t, 2H, J=6.0 Hz), 4.10-4.30(m, 1), 6.31(s, 1H), 6.54 (d, 1H, J=3.2 Hz), 6.83-7.09 (m, 3H), 7.13(d, 1H, J=3.2 Hz), 7.35(s, 2H), 7.78(s, 1H), 7.93(s, 1H), 8.40-8.50(m, 1H).

Example 71

4-{2-[3-[1-[2-methyl-1-(1-methylethyl)propyl]indol-5-yl]isocrotonoylamino]phenoxy}butyric acid (Compound 71)

0.38 g of Compound 71 was obtained in a similar manner to those described in the Examples 1 and 2 using 0.85 g of ethyl 4-(2-aminophenoxy)butyrate and 0.57 g of 3-{1-[2-methyl-1-(1-methylethyl)propyl]indol-5-yl}isocrotonic acid obtained according to the the method described in the Reference Examples 1-4.

Melting point: 150°-152° C.

| Elementary Analysis (%): $C_{29}H_{36}N_2O_4.0.2\ H_2O$ | | | |
|---|---|---|---|
| | C | H | N |
| Calculated value; | 72.53 | 7.64 | 5.83 |
| Observed value; | 72.60 | 7.54 | 5.93 |

IR (KBr)cm$^{-1}$: 3342, 2870, 1726, 1593, 1322.
$^1$HNMR (CDCl$_3$) (δ, ppm): 0.81(d, 6H, J=6.7 Hz), 0.92(d, 6H, J=6.7 Hz), 2.10-2.59(m, 6H), 2.73(s, 3H), 3.88(t, 1H, J=7.3 Hz), 4.11(t, 2H, J=5.8 Hz), 6.43(s, 1H), 6.57(d, 1H, J=3.3 Hz), 6.75-6.98(m, 3H), 7.14(d, 1H, J=3.3 Hz), 7.39(s, 2H), 7.81(s, 1H), 8.12(s, 1H) 8.44-8.54(m, 1H).

Example 72

4-{2-[3-[1-[2,2'-dimethylbenzhydryl)indol-5-yl]isocrotonoylamino]phenoxy}butyric acid (Compound 72)

0.55 g of amorphous compound 72 was obtained in a similar manner to those described in the Examples 1 and 2 using 0.63 g of ethyl 4-(2-aminophenoxy)butyrate and 0.56 g of 3-[1-[2,2'-dimethylbenzhydryl)indol-5-yl] isocrotonic acid obtained according to the procedures described in the Reference Examples 1-4.

| Elementary Analysis (%): $C_{37}H_{36}N_2O_4.0.5\ H_2O$ | | | |
|---|---|---|---|
| | C | H | N |
| Calculated value; | 76.40 | 6.41 | 4.82 |
| Observed value; | 76.35 | 6.66 | 4.48 |

IR (KBr)cm$^{-1}$: 3400, 2950, 1722, 1659, 1588, 1462.
$^1$HNMR (CDCl$_3$) (δ, ppm): 2.06–2.23(m, 2H), 2.14(s, 6H), 2.68(s, 3H), 4.07 (t, 3H, J=5.5 Hz), 6.29(s, 1H), 6.49(d, 1H, J=3.2 Hz), 6.64(d, 1H, J=7.9 Hz), 6.69(s, 1H), 6.70(d, 1H, J=3.2 Hz), 6.85–7.26(m, 12H), 7.79(s, 1H), 7.94(s, 1H), 8.30–8.52(m, 1H).

Example 73

4-{2-[3-[1-[2,3'-dimethylbenzhydryl)indol-5-yl]isocrotonoylamino]phenoxy}butyric acid (Compound 73)

0.20 g of compound 73 was obtained in a similar manner to those described in the Examples 1 and 2 using 0.41 g of ethyl 4-(2-aminophenoxy)butyrate and 0.36 g of 3-[1-(2,3'-dimethylbenzhydryl)indol-5yl]isocrotonic acid obtained according to the procedures described in the Reference Examples 1–4.
Melting point: 97°–101° C.

| Elementary Analysis (%): $C_{37}H_{36}N_2O_4.0.4\ H_2O$ | | | |
|---|---|---|---|
| | C | H | N |
| Calculated value; | 76.63 | 6.40 | 4.83 |
| Observed value; | 76.59 | 6.50 | 4.71 |

IR (KBr)cm$^{-1}$: 3820, 3345, 2848, 1705, 1593, 1514, 1320.

$^1$HNMR (CDCl$_3$) (δ, ppm): 2.09–2.32(m, 2H), 2.15(s, 3H), 2.28(s, 3H), 2.44–2.64(m, 2H), 2.68(s, 3H), 4.06(t, 2H, J=5.5 Hz), 4.60–5.0(m, 1H), 6.29 (s, 1H), 6.49(d, 1H, J=Hz), 6.74(s, 1H), 6.75(d, 1H, J=3.2 Hz), 6.77–6.99(m, 4H), 7.01–7.41(m, 9H), 7.80(s, 1H), 7.93(s, 1H), 8.30–8.50 (m, 1H).

Example 74

4-{2-[3-[1-(2,4'-dimethylbenzhydryl)indol-5-yl]isocrotonoylamino]phenoxy}butyric acid (Compound 74)

0.38 g of compound 74 was obtained in a similar manner to those described in the Examples 1 and 2 using 0.51 g of ethyl 4-(2-aminophenoxy)butyrate and 0.45 g of 3-[1-(2,4'-dimethylbenzhydryl)indol-5-yl]isocrotonic acid obtained according to the procedures described in the Reference Examples 1–4.
Melting point 173°–177° C.

| Elementary Analysis (%): $C_{37}H_{36}N_2O_4.0.2\ H_2O$ | | | |
|---|---|---|---|
| | C | H | N |
| Calculated value; | 77.11 | 6.37 | 4.86 |
| Observed value; | 77.13 | 6.57 | 4.62 |

IR (KBr)cm$^{-1}$: 3340, 2862, 1714, 1592, 1318, 1249.
$^1$HNMR (CDCl$_3$)(δ, ppm): 2.10–2.28(m, 2H), 2.16(s, 3H), 2.33(s, 3H), 2.45–2.53(m, 2H), 2.67(s, 3H), 4.06(t, 2H, J=5.7 Hz), 6.29(s, 1H), 6.48(d, 1H, J=3.3 Hz), 6.70–7.78(m, 14H), 6.73(s, 1H), 6.75(d, 1H, J=3.3 Hz), 7.78(d, 1H, J=0.9 Hz), 7.92–7.95(m, 1H), 8.30–8.50(m, 1H).

Example 75

4-{2-[3-[1-[3-methyl-1-(2-methylpropyl)butyl]indol-5-yl]isocrotonoylamino]phenoxy}butyric acid (Compound 75) and sodium salts (Compound 75 Na)

Compound 75 was obtained in a similar manner to the Examples 1 and 2 using 1.20 g of ethyl 4-(2-aminophenoxy)butyrate and 0.88 g of 3-{1-[3-methyl-1-(2-methylpropyl)butyl]indol-5-yl}isocrotonic acid obtained in a similar manner to the Reference Example 1–4. 0.17 g of amorphous-like Compound 75 Na was obtained in a similar manner to the Example 19.

| (Compound 75) Elementary Analysis (%): $C_{31}H_{39}N_2O_4Na.2\ H_2O$ | | | |
|---|---|---|---|
| | C | H | N |
| Calculated value; | 65.54 | 7.74 | 4.93 |
| Observed value; | 65.52 | 7.38 | 4.80 |

Compound 75

IR (CHCl$_3$ solution)cm$^{-1}$:3408, 2952, 1657, 1451.
$^1$H-NMR (CDCl$_3$) (δ, ppm): 0.80(d, 6H, J=5.9 Hz), 0.87(d, 6H, J=7.9 Hz), 1.14–1.91(m, 6H), 2.06–2.30(m, 2H), 2.45–2.62(m, 2H), 2.70(s, 3H), 4.0–5(t, 2H, J=5.7 Hz), 4.30–4.70(m, 1H), 6.33(s, 1H), 6.55(d, 1H, J=3.2 Hz), 6.76–7.04(m, 3H), 7.12(d, 1H, J=3.2 Hz), 7.36(s, 2H), 7.77)s, 1H), 8.01(s, 1H), 8.30–8.60(m, 1H), 8.60–8.90(m, 1H).

Example 76

4-{2-[3-[1-(1,5-dimethylhexyl)indol-5-6l]isocrotonoylamino]phenoxy}butyric acid (Compound 76) and sodium salts (Compound 76 Na)

Compound 76 was obtained in a similar manner to the Examples 1 and 2 using 0.94 g of ethyl 4-(2-aminophenoxy) butyrate and 0.66 g of 3-[1-(1,5-dimethylhexyl) indol-5-yl]isocrotonic acid obtained in a similar manner to the Reference Examples 1–4. 0.41 g of amorphous-like Compound 75 Na was obtained in a similar manner to the Example 19.

| (Compound 76 Na) Elemental analysis (%): $C_{30}H_{37}N_2O_4Na$ | | | |
|---|---|---|---|
| | C | H | N |
| Calculated value | 70.30 | 7.28 | 5.46 |
| Observed value | 70.44 | 7.34 | 5.22 |

IR (CHCl$_3$ solution)cm$^{-1}$:3430, 2960, 1597, 1451, 1328, 1118.
$^1$H-NMR (CDCl$_3$) (δ, ppm) : 0.80(d, 6H, J=5.9 Hz), 1.10–1.44(m, 6H), 1.48(d, 3H, J=6.6 Hz), 1.72–1.95(m, 1H), 2.03–2.35(m, 2H), 2.46–2.61(m, 2H), 2.71(s, 3H), 4.07(t, 2H, J=7.0 Hz), 4.44(q, 1H, J=6.6 Hz), 6.32(s, 1H), 6.54(d, 1H, J=3.2 Hz), 6.83–7.02(m, 3H), 7.17(d, 1H, J=3.2 Hz), 7.35(s, 2H), 7.78(s, 1H), 7.98(s, 1H), 8.44–8.57(m, 2H).

Example 77

4-{2-[3-[1-[α-(2-methyl)-propylbenzyl]indol-5-yl]iso-crotonoylamino]phenoxy}butyric acid (Compound 77)

0.21 g of Compound 77 was obtained in a similar manner to the Examples 1 and 2 using 0.34 g of ethyl 4-(2-aminophenoxy)butyrate and 0.27 g of 3-{1-[α-(2-methyl) propylbenzyl]indol-5-yl}isocrotonic acid obtained in a similar manner to the Reference Examples 1–4.

Melting point: 68°-72° C.

| Elemental analysis(%): $C_{32}H_{36}N_2O_4 \cdot 0.5H_2O \cdot 0.2C_2H_6O$ | | | |
|---|---|---|---|
| | C | H | N |
| Calculated value | 73.90 | 7.09 | 5.16 |
| Observed value | 74.03 | 6.92 | 4.78 |

IR (KBr)cm$^{-1}$:3400, 2868, 1595, 1527, 1514, 1445, 1153, $^1$H-NMR (CDCl$_3$) (δ, ppm):0.97(d, 6H, J=6.4 Hz), 1.40–1.70(m, 1H), 2.04–2.36(m, 4H), 2.44–2.68(m, 2H), 2.68(d, 3H, J=1.0 Hz), 4.07(t, 2H, J=6.0 Hz), 5.55(dd, 1H, J=6.3 & 9.6 Hz), 6.29(d, 1H, J=a.0 Hz), 6.59(d, 1H, J=3.3 Hz), 6.82–7.03(m, 3H), 7.16–7.53(m, 9H), 7.78(s, 1H), 7.92(s, 1H), 8.27–8.52(m, 1H).

Example 78

4-{2-[3-[1-(2-methyl-α-propylbenzyl)indol-5-yl]iso-crotonoylamino]phenoxy}butyric acid (Compound 78)

0.83 g of Compound 78 was obtained in a similar manner to the Examples 1 and 2 using 1.27 g of ethyl 4-(2-aminophenoxy)butyrate and 0.99 g of 3-[1-(2-methyl-α-propylbenzyl) indol-5-yl]isocrotonic acid obtained in a similar manner to the Reference Examples 1–4.

Melting point: 156°-158° C.

| Elemental analysis (%): $C_{33}H_{36}N_2O_4$ | | | |
|---|---|---|---|
| | C | H | N |
| Calculated value | 75.55 | 6.92 | 5.34 |
| Observed value | 75.74 | 7.03 | 5.19 |

IR (KBr)cm$^{-1}$:3338, 1713, 1537, 1454, 1327.

$^1$H-NMR (CDCl$_3$) (δ, ppm) : 0.95(t, 3H, J=7.2 Hz), 2.00–2.27(m, 4H), 2.27(s, 3H), 2.45–2.60(m, 2H), 2.67(d, 3H, J=1.1 Hz), 4.05(t, 2H, J=6.0 Hz), 5.61(t, 1H, J=7.4 Hz), 6.26(s, 1H), 6.52(d, 1H, J=3.3 Hz), 6.85–6.99(m, 4H), 7.11–7.30(m, 3H), 7.12(s, 4H), 7.75(s, 1H), 7.90(s, 1H), 8.25–8.50(m, 1H).

Example 79

4-{2-[3-[1-(α-butyl-2-methylbenzyl)indol-5-yl]iso-crotonoylamino]phenoxy}butyric acid (Compound 79)

0.62 g of Compound 79 was obtained in a similar manner to the Examples 1 and 2 using 1.04 g of ethyl 4-(2-aminophenoxy)butyrate and 0.84 g of 3-[1-(α-butyl-2-methylbenzyl)indol-5-yl]isocrotonic acid obtained in a similar manner to the Reference Examples 1–4.

Melting point: 166°-168° C.

| Elemental analysis (%): $C_{34}H_{38}N_2O_4 \cdot 0.3H_2O$ | | | |
|---|---|---|---|
| | C | H | N |
| Calculated value | 75.06 | 7.15 | 5.15 |
| Observed value | 74.99 | 7.17 | 5.05 |

IR (KBr) cm$^{-1}$:3340, 1714, 1597, 1537, 1454, 1329.

$^1$H-NMR (CDCl$_3$) (δ, ppm) : 0.80–1.00(m, 3H), 1.25–1.50(m, 4H), 2.00–2.35(m, 4H), 2.31(s, 3H), 2.40–2.60(m, 2H), 2.71(d, 3H, J=1.1 Hz), 4.09(t, 2H, J=6.0 Hz), 5.61(t, 1H, J=7.4 Hz), 6.38(d, 1H, J=1.1 Hz), 6.54(d, 1H, J=3.3 Hz), 6.80–7.03(m, 3H), 7.16(s, 4H), 7.21(d, 1H, J=3.3 Hz), 7.23–7.31(m, 2H), 7.79(s, 1H), 8.05(s, 1H), 8.40–8.55(m, 1H).

Example 80

4-{2-[3-[1-(α-butyl-4-methylbenzyl)indol-5-yl]iso-crotonoylamino]phenoxy}butyric acid (Compound 80)

0.64 g of amorphous-like Compound 80 was obtained in a similar manner to the Examples 1 and 2 using 0.76 g of ethyl 4-(2-aminophenoxy)butyrate and 0.62 g of 3-[1-(α-butyl-4-methylbenzyl)indol-5-yl]isocrotonic acid obtained in a similar manner to Reference Examples 1–4.

| Elemental analysis (%): $C_{34}H_{36}N_2O_4 \cdot 0.2H_2O$ | | | |
|---|---|---|---|
| | C | H | N |
| Calculated value | 75.59 | 6.79 | 5.19 |
| Observed value | 75.67 | 7.22 | 5.10 |

IR (KBr)cm$^{-1}$: 2860, 1652, 1588, 1115.

$^-$H-NMR (CDCl$_3$) (δ, ppm) : 0.75–1.00(m, 3H), 1.20–1.50(m, 4H), 2.05–2.35(m, 4H), 2.27(s, 3H), 2.52(t, 2H, J=6.0 Hz), 2.68(s, 3H, J=1.0 Hz), 4.06(t, 2H, J=5.9 Hz), 5.38(t, 1H, J=6.9 Hz), 6.27(d, 1H, J=1.0 Hz), 6.56(d, 1H, J=3.3 Hz), 6.75–6.99(m, 3H), 7.06(s, 4H), 7.26(d, 1H, J=3.3 Hz), 7.28(s, 2H), 7.76(s, 1H), 7.91(s, 1H), 8.28–8.48(m, 1H).

EXAMPLE 81

4-{2-[3-[1-[1-(2-naphthyl)ethyl[indol-5-yl]isocrotonoyl amino]phenoxy}butyric acid (Compound 81)

1.06 g of amorphous-like compound 81 was obtained in a similar manner to the Examples 1 and 2 using 1.34 g of ethyl 4-(2-aminophenoxy)butyrate and 1.07 g of 3-{1-[1-(2-naphthyl)ethyl]indol-5-yl}isocrotonic acid obtained in a similar manner to the reference Examples 1–4+1.

| Elemental analysis (%): $C_{34}H_{32}N_2O_4 \cdot 0.5H_2O$ | | | |
|---|---|---|---|
| | C | H | N |
| Calculated value | 75.39 | 6.14 | 5.17 |
| Observed value | 75.57 | 6.39 | 4.79 |

IR (CHCl$_3$ solution ) cm$^{-1}$: 3350, 2970, 1602, 1519, 1450, 1157.

$^1$H-NMR (CDCl$_3$) (δ, ppm): 1.99(d, 3H, J=7.1 Hz), 208–2.25(m, 2H), 1.50 (t, 2H, J=6.7 Hz), 2.68(d, 3H, J=0.8 Hz), 4.04(t, 2H, J=5.9 Hz), 5.79(q, 1H, J=7.1 Hz), 6.29(d, 1H, J=0.8 Hz), 6.61(d, 1H, J=3.2 Hz), 6.81(dd, 1H, J=1.7–7.7 Hz), 6.89–7.00(m, 2H), 7.19–7.31(m 3H), 7.41–7.50(m, 2H), 7.60(s, 1H), 7.73–7.85(m, 4H), 7.94(s, 1H), 8.40–8.55(m, 1H).

EXAMPLE 82

4-{2-[3-[1-(4-methoxybenzhydryl)indol-5-yl]iso-crotonoylamino]phenoxy}butyric acid (Compound 82) and sodium salts (Compound 82 Na)

Compound 82 was obtained in a similar manner to the Examples 1 and 2 using 0.89 g of ethyl 4(2-aminophenoxy)butyrate and 0.79 g of 3-[1(4-methoxybenzhydryl)indol-5-yl]isocrotonic acid obtained in a similar manner to the Reference Examples 1–4. 0.62 g of amorphous-like Compound 82 Na was obtained in a similar manner t the Example 19.

| (Compound 82 Na) Elemental analysis (%): $C_{36}H_{33}N_2O_5Na.1.5H_2O$ | | | |
|---|---|---|---|
| | C | H | N |
| Calculated value | 69.33 | 5.82 | 4.49 |
| Observed value | 69.40 | 5.67 | 4.20 |

Compound 82

IR (CHCl$_3$ solution) cm$^{-1}$: 3414, 1649, 1600, 1514, 1451.

$^1$H-NMR (CDCl$_3$) (δ, ppm): 1.90–2.25(m, 2H), 2.38–2.60(m, 2H), 2.66(s, 3H), 3.75(s, 3H), 3.97–4.14 (, 2H), 6.29(s, 1H), 6.49(d, 1H, J=3, 1Hz, 6.65–71.0(m, 11H), 7.13–7.35(m, 5H), 7.78(s, 1H), 8.25–8.50 (m, 1H), 8.65–9.05 (, 1H).

EXAMPLE 83

4}2-[3-[1-(4-trifluoromethylbenzhydryl)indol-5-yl[iso-crotonoylamino[phenoxy}butyric acid (Compound 83)

0.49 g of Compound 83 was obtained in a similar manner to the Examples 1 and 2 using 1.70 g of ethyl 4-(2-aminophenoxy)butyrate and 1.66 g of 3-[1(4-trifluoromethylbenzhydryl)indol-5-yl]isocrotonic acid obtained in a similar manner to the Reference Examples 1–4.

Melting point: 166°–170° C.

| Elemental analysis (%): $C_{36}H_{31}N_2O_4F_3$ | | | |
|---|---|---|---|
| | C | H | N |
| Calculated value | 70.58 | 5.10 | 4.57 |
| Observed value | 70.47 | 5.19 | 4.45 |

IR (KBR) cm$^1$: 3320, 1717, 1597, 1522, 1452, 1325. $^1$H-NMR (CDCl$_3$) (δ, ppm): 2.10–2.30 (m 2H), 2.44–2.60(m, 2H), 2.66(s, 3H), 4.05(t, 2H, J=5.9 Hz), 6.28(s, 1H), 6.53(d, 1H, J=3.3 Hz), 6.83(s, 1H), 7.00–740(m, 9H), 7.57(d, 2H, J=8.4 Hz), 7.78(d, 1H, J=1.1 Hz), 7.93(s, 1H), 8.30–8.55(m, 1H).

EXAMPLE 84

4-{2-[3-[1-[phenyl-(3-pyridyl)methyl[indol-5yl]iso-crotonoylamino]phenoxyl}butyric acid (Compound 84)

0.27 g of amorphous-like Compound 84 was obtained in a similar manner to the Examples 1 and 2 using 0.72 g of ethyl 4-(2-aminophenoxy)butyrate and 0.60 g of 3-{1-[phenyl-(3-pyridyl)methyl]indol-5-yl}isocrotonic acid obtained in a similar manner to the Reference Examples 1–4.

Melting point: 171°–172° C.

| Elemental analysis (%): $C_{34}H_{31}N_3O_4.0.25H_2O$ | | | |
|---|---|---|---|
| | C | H | N |
| Calculated value | 74.23 | 5.77 | 7.64 |
| Observed value | 74.04 | 5.64 | 7.50 |

IR (KBr)cm$^{-1}$: 3400, 2940, 1599, 1525, 1475, 1214.

$^1$H-NMR (DMSO-d$_6$) (δ, ppm): 2.00–2.20(m, 2H), 2.35–2.55(m, 2H), 2.61 (d, 3H, J=0.6 Hz), 4.06(t, 2H, J=5.7 Hz), 6.58(d, 1H, J=3.3 Hz), 6.66(d, 1H, J=0.6 Hz), 6.80–7.00(m, 2H), 7.10(d, 1H, J=3.3 Hz), 7.15–7.55(m, 9H), 7.83 (d, 1H, J=1.1 Hz), 8.00–8.15 (, 1H), 8.40(s, 1H), 8.48–8.58(m, 1H), 8.8

EXAMPLE 85

4-{2-[3-[1-[phenyl-(4-pyridyl)methyl]indol-5-yl]iso-crotonoylamino]phenoxy}butyric acid (Compound 85)

0.22 g of amorphous-like Compound 85 was obtained in a similar manner to the Examples 1 and 2 using 0.45 g of ethyl 4-(2-aminophenoxy)butyrate and 0.37 g of 3{1-[phenyl-(4-pyridyl)methyl]indol-5-yl}isocrotonic acid obtained in a similar manner to the Reference Examples 1–4.

| Elemental analysis (%): $C_{34}H_{31}N_2O_4.H_2O$ | | | |
|---|---|---|---|
| | C | H | N |
| Calculated value | 72.45 | 5.90 | 7.46 |
| Observed value | 72.14 | 5.90 | 7.46 |

IR (CHCl$_3$ solution) cm$^{-1}$: 3350, 2928, 166, 1602, 1519, 1474, 1155. $^1$H-NMR (CDCl$_3$) (δ, ppm): 2.00–2.35(m, 2H), 2.40–2.70(m, 2H), 2.65(s, 3H), 4.08(t, 2H, J=5.7 Hz), 6.36(s, 1H), 6.50(d, 1H, J=3.3 Hz), 6.60–7.20 (m, 11H), 7.25–7.50(m, 4H), 7.75(s, 1H), 8.16(s, 1H), 8.30–8.60 (m; 3H).

EXAMPLE 86

4-}3-[3-[1-(1-propylbutyl)indol-5-yl]iso-crotonoylamino]phenoxy}butyric acid (Compound 86)

0.24 g of Compound 86 was obtained in a similar manner to the Example 2 using 0.35 g of compound F obtained in the reference Example 6.

Melting point: 87°–89° C.

| Elemental analysis (%): $C_{29}H_{36}N_2O_4.0.1C_6H_{14}O$ | | | |
|---|---|---|---|
| | C | H | N |
| Calculated value | 73.03 | 7.74 | 5.75 |
| Observed value | 73.18 | 8.01 | 5.88 |

IR (KBR) cm$^{-1}$: 3200, 2806, 1768, 1655, 1534, 1262, 1214.

$^1$-NMR (CDCl$_3$) (δ, ppm): 0.84(t, 6H, J=7.3 Hz), 1.04–1.26(m, 4H), 1.72–1.94(m, 4H), 2.05–2.15(m, 2H), 2.57(t, 2H, J=7.3 Hz), 2.72(d, 3H, J=1.0Hz), 4.03(t, 2H, J=6.1 Hz), 4.25–4.35(m, 1H), 6.19(d, 1H, J=1.0 Hz), 6.55 (d, 1H, J=3.1 Hz), 6.63(dd, 1H, J=2.08–8.1 Hz), 6.98(d, 1H, J=8.1 Hz), 7.15 (d, 1H, J=3.1 Hz), 7.18(t, 1H, J=8.1 Hz), 7.25(s, 1H), 7.33(s, 1H), 7.30–7.45(m, 1H), 7.76(s, 1H).

EXAMPLE 87

4-}4-[3-[1-(1-propylbutyl)indol-5-yl]isocrotonoyl]-phenoxy}butyric acid (Compound 87)

0.25 g of Compound 87 was obtained in a similar manner to the Reference Example 6 and the Example 2 using 0.45 g of ethyl 4-(4-aminophenoxy)butyrate and 0.30 g of 3-[1-(1-propylbutyl)indol-5-yl]isocrotonic acid obtained in a similar manner to the Reference Examples 1–4.

Melting point: 124°–125° C.

| Elemental analysis (%): $C_{29}H_{36}N_2O_4 \cdot 0.2H_2O$ | | | |
|---|---|---|---|
| | C | H | N |
| Calculated value | 72.98 | 7.87 | 5.64 |
| Observed value | 73.11 | 8.03 | 5.83 |

IR (KBr) cm$^{-1}$: 3300, 2930, 1712, 1608, 1516, 1240, 1164.

$^1$H-NMR (CDCl$_3$) (δ, ppm): 0.84(t, 6H, J=7.3 Hz), 1.04–1.26(m, 4H), 1.72–1.93 (m, 4H), 2.06–2.16(m, 2H), 2.58(t, 2H, J=7.3 Hz), 2.70(d, 3H, J=1.0 Hz), 4.00(t, 2H, J=5.9 Hz), 4.26–4.30(m, 1H), 6.18(d, 1H, J=1.0 Hz), 6.52 (d, 1H, J=3.0 Hz), 7.33(s, 1H), 7.40–7.55(m, 1H), 7.47(d, 2H, J=8.7 Hz), 7.76 (s, 1H).

Example 88

4-{2-[3-[1-(1-propylbutyl)indol-5-yl]-cis-2-pentenoylamino]phenoxy}butyric acid (Compound 88)

0.49 g of Compound 88 was obtained in a similar manner to the Examples 1 and 2 using 0.71 g of ethyl 4-(2-aminophenoxy)butyrate and 0.50 g of 3-[1-(1-propylbutyl)indol-5-yl]-cis-2-pentenoic acid obtained in a similar manner to the Reference Examples 3 and 5.

Melting point: 165°–166° C.

| Elemental analysis (%): $C_{30}H_{38}N_2O_4 \cdot 0.4H_2O$ | | | |
|---|---|---|---|
| | C | H | N |
| Calculated value | 72.38 | 7.86 | 5.62 |
| Observed value | 72.38 | 7.95 | 5.58 |

IR (KBr)cm$^{-1}$: 3222, 2822, 1647, 1568, 1476, 1253, 1206, 1158.

$^1$H-NMR (CDCl$_3$) (δ, ppm): 0.83(t, 6H, J=6.6 Hz), 1.03–1.37(m, 4H), 1.16 (t, 3H, J=7.5 Hz), 1.70–2.03(m, 4H), 2.05–2.28(m, 2H), 2.42–2.61(m, 2H), 3.24(q, 2H, J=7.5 Hz), 4.07(t, 2H, J=5.9 Hz), 4.28(dt, 1H, J=7.1 Hz), 5.70–5.90 (m, 1H), 6.16(s, 1H), 6.54(d, 1H, J=3.2 Hz), 6.75–7.14(m, 3H), 7.28 (d, 1H, J=3.2 Hz), 7.39(s, 2H), 7.74(s, 1H), 7.91(s, 1H), 8.25–8.55(m, 1H).

Example 89

4-{2-[3-[1-(1-propylbutyl)indol-5-yl]-cis-2-pentenoylamino]-5-fluorophenoxy}butyric acid (Compound 89)

0.30 g of Compound 89 was obtained in a similar manner to the Examples 1 and 2 using 0.77 g of ethyl 4-(2-amino-5-fluorophenoxy)butyrate and 0.50 g of 3-[1-(1-propylbutyl)indol-5-yl]-cis-2-pentenoic acid obtained in a similar manner to the Reference Examples 3 and 5.

Melting point: 122°–125° C.

| Elemental analysis (%): $C_{30}H_{37}FN_2O_4 \cdot H_2O$ | | | |
|---|---|---|---|
| | C | H | N |
| Calculated value | 70.18 | 7.41 | 5.42 |
| Observed value | 70.23 | 7.65 | 5.43 |

IR (CHCl$_3$ solution)cm$^{-1}$: 3408, 2934, 1661, 1651, 1564, 1521, 1495, 1464, 1157, 1107.

$^1$H-NMR (CDCl$_3$) (δ, ppm): 0.84(t, 6H, J=7.2 Hz), 1.02–1.25(m, 7H), 1.77–1.87 (m, 4H), 2.06–2.30(m, 2H), 2.53(t, 3H, J=6.7 Hz), 3.24(q, 2H, J=7.4 Hz), 4.04(t, 2H, J=6.4 Hz), 4.324–4.35(m, 1H), 6.16(s, 1H), 6.55(d, 1H, J=2.8 Hz), 6.56–6.58(m, 2H), 7.15(d, 1H, J=2.8 Hz), 7.34(s, 2H), 7.75(s, 1H), 8.50–8.40(m, 1H).

Example 90

4-{2-[3-[1-(1-propylpentyl)indol-5-yl]-cis-2-pentenoylamino]phenoxy}butyric acid (Compound 90) and sodium salts (Compound 90 Na)

Compound 90 was obtained in a-similar manner to the Examples 1 and 2 using 0.68 g of ethyl 4-(2-aminophenoxy)butyrate and 0.50 g of 3-[1-(1-propylpentyl)indol-5-yl]-cis-2-pentenoic acid obtained in a similar manner to the Reference Examples 3 and 5. 0.56 g of amorphous-like Compound 90 Na was obtained in a similar manner to the Example 19.

| (Compound 90 Na) Elemental analysis (%): $C_{31}H_{39}N_2O_4Na \cdot 0.2H_2O$ | | | |
|---|---|---|---|
| | C | H | N |
| Calculated value | 70.22 | 7.49 | 5.28 |
| Observed value | 70.25 | 7.81 | 5.11 |

IR (NaCl)cm$^{-1}$: 2890, 1603, 1522, 1452, 1253, 752.

$^1$H-NMR (CDCl$_3$) (δ, ppm): 0.80(t, 3H, J=7.4 Hz), 0.84(t, 3H, J=7.4 Hz), 0.99–1.31(m, 6H), 1.18(t, 3H, J=7.4 Hz), 1.74–1.91(m, 4H), 2.11–2.21(m, 2H), 2.54(t, 2H, J=6.9 Hz), 3.26(q, 2H, J=7.4 Hz), 4.08(t, 2H, J=6.2 Hz), 4.22–4.33(m, 1H), 6.19(s, 1H), 6.56(d, 1H, J=3.2 Hz), 6.84(dd, 1H, J=2.5 Hz–9.4 Hz), 7.15(d, 1H, J=3.2 Hz), 7.34(s, 2H), 7.77(s, 1H), 7.92(s, 1H), 8.45–8.5(m, 1H).

Example 91

4-{2-[3-[1-(1-propylpentyl)indol-5-yl]-cis-2-pentenoylamino]-5-fluorophenoxy}butyric acid (Compound 91) and sodium salts (Compound 91 Na)

Compound 91 was obtained in a-similar manner to the Examples 1 and 2 using 0.83 g of ethyl 4-(2-amino-5-fluorophenoxy)butyrate and 0.50 g of 3-[1-(1-propylpentyl)indol-5-yl]-cis-2-pentenoic acid obtained in a similar manner to the Reference Examples 3 and 5. 0.79 g of amorphous-like Compound 91 Na was obtained in a similar manner to the Example 19.

| (Compound 91 Na) Elemental analysis (%): $C_{31}H_{39}FN_2O_4Na \cdot 2H_2O$ | | | |
|---|---|---|---|
| | C | H | N |
| Calculated value | 64.73 | 7.25 | 4.87 |
| Observed value | 64.66 | 7.16 | 4.82 |

Compound 91 Na

IR (KBr)cm$^{-1}$: 2940, 1662, 1512, 1463, 1273, 1155.

$^1$H-NMR (CDCl$_3$) ($\delta$, ppm): 0.73–0.95(m, 6H), 1.00–1.37(m, 6H), 1.15(t, 3H, J=7.2 Hz), 1.67–1.98(m, 4H), 2.00–2.20(m, 2H), 2.25–2.50(m, 2H), 3.22(q, 2H, J=7.2 Hz), 4.02(t, 2H, J=5.3 Hz), 4.05–4.35(m, 1H), 6.17(s, 1H), 6.50–6.72(m, 2H), 6.54(d, 1H, J=3.3 Hz), 7.32(s, 2H), 7.73(s, 1H), 8.20–8.40(m, 1H).

Example 92

4-{2-[3-[1-[3-methyl-1-(2-methylpropyl)butyl]indol-5-yl]-cis-2-pentenoylamino]phenoxy}butyric acid (Compound 92) and sodium salts (Compound 92 Na)

Compound 92 was obtained in a similar manner to the Examples 1 and 2 using 0.52 g of ethyl 4-(2-aminophenoxy)butyrate and 0.40 g of 3-{1-[3-methyl-1-(2-methylpropyl)butyl]indol-5-yl}-cis-2-pentenoic acid obtained in a similar manner to the Reference Examples 3 and 5. 0.13 g of amorphous-like Compound 92 Na was obtained in a similar manner to the Example 19.

| (Compound 92 Na) Elemental analysis (%): C$_{32}$H$_{41}$N$_2$O$_4$Na.24H$_2$O | | | |
|---|---|---|---|
| | C | H | N |
| Calculated value | 65.82 | 7.91 | 4.80 |
| Observed value | 65.87 | 7.78 | 4.66 |

Compound 92

IR (KBr)cm$^{-1}$: 3420, 2958, 1670, 1601, 1516, 1463, 1117.

$^1$H-NMR (CDCl$_3$) ($\delta$, ppm): 0.81(d, 6H, J=6.4 Hz), 0.90(d, 6H, J=6.4 Hz), 1.18–1.30(m, 9H), 2.06–2.30(m, 2H), 2.51(t, 2H, J=6.9 Hz), 3.25(q, 2H, J=7.3 Hz), 4.05(t, 2H, J=6.1 Hz), 4.40–4.52(m, 1H), 6.19(s, 1H), 6.67(d, 1H, J=3.0 Hz), 6.81–6.84(m, 1H), 6.92–7.02(m, 2H), 7.14(d, 1H, J=3.0 Hz), 7.35 (s, 2H), 7.76(s, 1H), 7.94(s, 1H), 8.45–8.55(m, 1H).

Example 93

4-{2-[3-(1-benzhydrylindol-5-yl)-cis-2-pentenoylamino]phenoxy}butyric acid (Compound 93)

52 mg of Compound 93 was obtained in a similar manner to the Examples 1 and 2 using 0.12 g of ethyl 4-(2-aminophenoxy)butyrate and 0.10 g of 3-(1-benzhydrylindol-5-yl)-cis-2-pentenoic acid obtained in a similar manner to the Reference Examples 1–4.

Elemental analysis (%): 76°–78° C.

| | C | H | N |
|---|---|---|---|
| Calculated value | 76.66 | 6.18 | 4.97 |
| Observed value | 76.66 | 6.24 | 4.81 |

IR (CHCl$_3$ solution)cm$^{-1}$: 3378, 2932, 1714, 1601, 1452, 1322.

$^1$H-NMR (CDCl$_3$) ($\delta$, ppm): 1.13(t, 3H, J=7.4 Hz), 2.03–2.22(m, 2H), 2.50(t, 2H, J=6.6 Hz), 3.22(q, 2H, J=7.4 Hz), 4.05(t, 2H, J=6.0 Hz), 6.13(s, 1H), 6.51(d, 1H, J=3.2 Hz), 6.80–7.30(m, 16H), 6.80(s, 1H), 6.85(d, 1H, J=3.2 Hz), 7.76(s, 1H), 7.89(s, 1H), 8.39–8.50(m, 1H).

Example 94

4-{2-[3-[1-(4,4'-difluorobenzhydryl)indol-5-yl]-cis-2-pentenoylaminmo]phenoxy}butyric acid (Compound 94)

0.19 g of Compound 94 was obtained in a similar manner to the Examples 1 and 2 using 0.31 g of ethyl 4-(4,4-difluorobenzhydryl)butyrate and 0.29 g of 3-[1-(4,4'-difluorobenzhydryl)indol-5-yl]-cis-2-pentenoic acid obtained in a similar manner to the Reference Examples 1–4.

Melting point: 150°–152° C.

| Elemental analysis (%): C$_{36}$H$_{32}$F$_2$N$_2$O$_4$.H$_2$O | | | |
|---|---|---|---|
| | C | H | N |
| Calculated value | 70.99 | 5.56 | 4.60 |
| Observed value | 70.89 | 5.46 | 4.46 |

IR (KBr)cm$^{-1}$: 3400, 1657, 1600, 1548, 1449, 1157, 1115.

$^1$H-NMR (CDCl$_3$) ($\delta$, ppm): 1.14(t, 3H, J=7.4 Hz), 2.10–2.20(m, 2H), 2.53(t, 2H, J=6.9 Hz), 3.22(q, 2H, J=7.4 Hz), 4.07(t, 2H, J=5.9 Hz), 6.14(s, 1H), 6.53(d, 1H, J=3.2 Hz), 6.77(s, 1H), 6.80(d, 1H, J=3.2 Hz), 6.84(dd, 1H, J=2.0 Hz–7.4 Hz), 6.95–7.10(m, 10H), 7.17(d, 1H, J=9.4 Hz), 7.28(d, 1H, J=9.4 Hz), 7.77(s, 1H), 7.90(s, 1H), 8.45–8.55(m, 1H).

Example 95

4-{2-[3-[1-(4,4'-difluorobenzhydryl)indol-5-yl]-4-methyl-cis-2-pentenoylamino]phenoxy}butyric acid (Compound 95)

67 mg of amorphous-like Compound 95 was obtained in a similar manner to the Example 2 and the Reference Example 6 using 0.11 g of ethyl 4-(2-aminophenoxy)butyrate and 0.14 g of 3-[1-(4,4'-difluorobenzhydryl)indol-5-yl]-4-methyl-cis-2-pentenoic acid obtained in a similar manner to the Reference Examples 3 and 5.

| Elemental analysis (%): C$_{37}$H$_{34}$N$_2$O$_4$F$_2$.0.2C$_6$H$_{14}$O.0.4H$_2$O | | | |
|---|---|---|---|
| | C | H | N |
| Calculated value | 72.08 | 6.08 | 4.33 |
| Observed value | 72.03 | 6.06 | 4.37 |

IR (KBr)cm$^{-1}$: 3240, 2904, 1662, 1630, 1536, 1480, 1256, 1180.

$^1$H-NMR (CDCl$_3$) ($\delta$, ppm): 1.10(d, 6H, J=6.8 Hz), 1.68–1.78(m, 2H), 2.29 (t, 2H, J=7.3 Hz), 2.76(dt, 1H, J=6.8 Hz), 3.51(t, 2H, J=6.3 Hz), 6.49(d, 1H, J=3.3 Hz), 6.62(dd, 1H, J=1.4 Hz–7.8 Hz), 6.74(s, 1H), 6.79(d, 1H, J=3.3 Hz), 6.80–6.93(m, 2H), 6.93–7.02(m, 9H), 7.15(d, 1H, J=8.3 Hz), 7.42(s, 1H), 7.54(s, 1H), 8.24(d, 1H, J=7.6 Hz).

Example 96

4-{2-[3-[1-(1-propylbutyl)indol-5-yl]-cis-2-hexenoylamino]phenoxy}butyric acid (Compound 96) and sodium salts (Compound 96 Na)

Compound 96 was obtained in a similar manner to the Reference Example 6 and the Example 2 using 0.34 g of ethyl 4-(2-aminophenoxy)butyrate and 0.25 g of 3-[1-(1-propylbutyl)indol-5-yl]-cis-2-hexenoic acid obtained in a similar manner to the Reference Examples 3 and 5.

0.20 g of amorphous-like Compound 96 Na was obtained in a similar manner to the Example 19.

| (Compound 96 Na) Elemental analysis (%): $C_{31}H_{39}N_2O_4Na\cdot2H_2O$ | | | |
|---|---|---|---|
| | C | H | N |
| Calculated value | 66.17 | 7.70 | 4.98 |
| Observed value | 65.95 | 7.36 | 4.86 |

(Compound 96)

IR (CHCl$_3$ solution)cm$^{-1}$: 2932, 1713, 1601, 1520, 1481, 910.

$^1$H-NMR (CDCl$_3$) (δ, ppm): 0.85(t, 6H, J=7.3 Hz), 0.98(t, 3H, J=7.3 Hz), 1.03–1.26(m, 4H), 1.47–1.69(m, 2H), 1.72–1.88(m, 2H), 2.12–2.22(m, 2H), 2.55(t, 2H, J=6.9 Hz), 3.23(t, 2H, J=7.8 Hz), 4.09(t, 2H, J=6.1 Hz), 4.20–4.35 (m, 1H), 6.19(s, 1H), 6.56(d, 1H, J=3.3 Hz), 6.85(dd, 1H, J=3.0 Hz–6.6 Hz), 6.93–7.01(m, 2H), 7.15(d, 1H, J=3.3 Hz), 7.33(s, 2H), 7.75(s, 1H), 7.89 (brs, 1H), 8.42–8.54(m, 1H):

Example 97

4-{2-[3-[1-(4,4'-difluorobenzhydryl)indol-5-yl]-cis-2-hexenoylamino]phenoxy}butyric acid (Compound 97)

0.25 g of amorphous-like Compound 97 was obtained in a similar manner to the Reference Example 6 and the Example 2 using 0.41 g of ethyl 4-(2-aminophenoxy) butyrate and 0.40 g of 3-[1-(4,4'-difluorobenzhydryl)indol-5-yl]-cis-2-hexenoic acid obtained in a similar manner to the Reference Examples 3 and 5.

| Elemental analysis (%): $C_{37}H_{34}N_2O_4F_2\cdot0.3H_2O$ | | | |
|---|---|---|---|
| | C | H | N |
| Calculated value | 72.37 | 5.68 | 4.56 |
| Observed value | 72.30 | 5.79 | 4.57 |

IR (KBr)cm$^{-1}$: 2960, 1653, 1539, 1473, 1116.

1H-NMR (CDCl$_3$) (δ, ppm): 0.95(t, 3H, J=7.5 Hz), 1.50(dq, 2H, J=7.5 Hz), 2.12–2.20(m, 2H), 2.53(t, 2H, J=6.9 Hz), 3.20(t, 2H, J=7.5 Hz), 4.07(t, 2H, J=6.1 Hz), 6.16(s, 1H), 6.53(d, 1H, J=3.4 Hz), 6.83(dd, 1H, J=1.8 Hz–7.5 Hz), 6.88–7.08(m, 10H), 7.16(d, 1H, J=8.5 Hz), 7.27(d, 1H, J=8.5 Hz), 7.76(s, 1H), 7.89(brs, 1H), 8.47–8.50(m, 1H).

Example 98

4-{2-[3-[1-(4,4'-difluorobenzhydryl)indol-5-yl)-cis-2-hexenoylamino]-5-fluorophenoxy}butyric acid (Compound 98)

0.20 g of Compound 98 was obtained in a similar manner to the Reference Example 6 and the Example 2 using 0.45 g of ethyl 4-(2-amino-5-fluorophenoxy) butyrate and 0.40 g of 3-[1-(4,4'-difluorobenzhydryl) indol-5-yl]-cis-2-hexenoic acid obtained in a similar manner to the Reference Examples 3 and 5.

Melting point: 136°–137° C.

| Elemental analysis (%): $C_{37}H_{33}N_2O_4F_3\cdot0.3H_2O$ | | | |
|---|---|---|---|
| | C | H | N |
| Calculated value | 70.31 | 5.38 | 4.43 |
| Observed value | 70.41 | 5.55 | 4.46 |

IR (KBr)cm$^{-1}$: 2960, 1723, 1600, 1506, 1158.

1H-NMR (CDCl$_3$) (δ, ppm): 0.94(t, 6H, J=7.6 Hz), 1.50(dq, 2H, J=7.6 Hz), 2.11–2.20(m, 2H), 2.52(t, 2H, J=6.7 Hz), 3.18(t, 2H, J=7.6 Hz), 4.04(t, 2H, J=6.2 Hz), 6.13(s, 1H), 6.53(d, 1H, J=3.5 Hz), 6.58(dd, 1H, J=2.7 Hz–9.2 Hz), 6.77(s, 1H), 6.80(d, 1H, J=3.5 Hz), 6.99–7.05(m, 8H), 7.16(d, 1H, J=8.4 Hz), 7.25(d, 1H, J=8.4 Hz), 7.74(brs, 1H), 8.33–8.45(m, 1H).

Example 99

4-{2-[3-cyclopropyl-3-[1-(4,4'-difluorobenzhydryl) indol-5-yl]-trans-2-acryloylamino]phenoxy}butyric acid (Compound 99)

50 mg of Compound 99 was obtained in a similar manner to the Example 2 and the Reference Example 6 using 0.16 g of ethyl 4-(2-aminophenoxy) butyrate and 0.15 g of 3-cyclopropyl-3-[1-(4,4'-difluorobenzhydryl) indol-5-yl]-trans-2-acrylic acid obtained in a similar manner to the Reference Examples 3 and 5.

Melting point: 87°–89° C.

| Elemental analysis (%): $C_{37}H_{32}N_2O_4F_2$ | | | |
|---|---|---|---|
| | C | H | N |
| Calculated value | 72.30 | 5.30 | 4.61 |
| Observed value | 72.25 | 5.35 | 4.48 |

IR (CHCl$_3$ solution)cm$^{-1}$: 3408, 2952, 1667, 1451.

$^1$H-NMR (CDCl$_3$) (δ, ppm): 0.52–0.58(m, 2H), 0.88–0.95(m, 2H), 2.08–2.18 (m, 2H), 2.51(t, 2H, J=6.9 Hz), 3.05–3.19(m, 1H), 4.07(t, 2H, J=6.2 Hz), 5.99(s, 1H), 6.50(d, 1H, J=3.5 Hz), 6.76(s, 1H), 6.79(d, 1H, J=3.5 Hz), 6.84(dd, 1H, J=2.2 Hz–7.7 Hz), 6.94–7.09(m, 2H), 7.13(d, 1H, J=8.4 Hz), 7.51(s, 1H), 7.96(brs, 1H), 8.45–8.57(m, 1H).

| Formulation Example 1 Tablet Tablets, each containing the following ingredients, are prepared by methods known in the art. | |
|---|---|
| Compound 2 | 100 mg |
| Lactose | 60 mg |
| Potato starch | 30 mg |
| Poly(vinylalcohol) | 2 mg |
| Magnesium stearate | 1 mg |

| Formulation Example 2 Powder Powder, each containing the following ingredients, is prepared by methods known in the art. | |
|---|---|
| Compound 3 | 150 mg |
| Lactose | 280 mg |

What is claimed is:

1. An indole derivative compound represented by the formula (I):

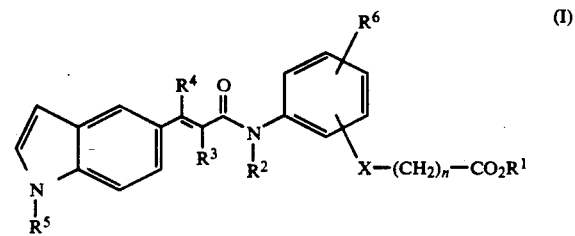

wherein:

$R^1$, $R^2$ and $R^3$ independently represent hydrogen or lower alkyl having 1-6 carbon atoms;

$R^4$ represents hydrogen, lower alkyl having 1-6 carbon atoms or cycloalkyl having 3-8 carbon atoms;

$R^5$ represents
(a) hydrogen,
(b) cycloalkyl having 3-8 carbon atoms, which cycloalkyl is unsubstituted or is substituted with 1 or 2 substituents which substituents are the same or different and are lower alkyl having 1-6 carbon atoms,
(c) cycloalkyl having 3-8 carbon atoms which cycloalkenyl is unsubstituted or is substituted with 1 or 2 substituents which are the same or different and are lower alkyl having 1-6 carbon atoms,
(d) —$CHR^7R^8$, wherein $R^7R^8$ independently represent
 (i) hydrogen,
 (ii) alkyl having 1-10 carbon atoms,
 (iii) alkenyl having 2-10 carbon atoms,
 (iv) alkynyl having 2-10 carbon atoms,
 (v) cycloalkyl having 3-8 carbon atoms, which cycloalkyl is unsubstituted or is substituted with 1 or 2 substituents which are the same or different and are lower alkyl having 1-6 carbon atoms, or
 (vi) —$(CH_2)_mOR^9$, wherein m is an integer between 1-3 and $R^9$ is lower alkyl having 1-6 carbon atoms,
 (vii) aryl which is unsubstituted or is substituted with 1-3 substituents, which substituents are independently selected from the group consisting of lower alkyl having 1-6 carbon atoms, hydroxy, lower alkoxy having 1-6 carbon atoms, lower alkylamino having 1-6 carbon atoms, trifluoromethyl and halogen,
 (viii) pyridyl which is unsubstituted or is substituted with 1-3 substituents, which substituents are independently selected from the group consisting of lower alkyl having 1-6 carbon atoms, hydroxy, lower alkoxy having 1-6 carbon atoms, lower alkylamino having 1-6 carbon atoms, trifluoromethyl and halogen,
 (ix) furyl which is unsubstituted or is substituted with 1-3 substituents, which substituents are independently selected from the group consisting of lower alkyl having 1-6 carbon atoms, hydroxy, lower alkoxy having 1-6 carbon atoms, trifluoromethyl and halogen,
 (x) thienyl which is unsubstituted or is substituted with 1-3 substituents, which substituents are independently selected from the group consisting of lower alkyl having 1-6 carbon atoms, hydroxy, lower alkoxy having 1-6 carbon atoms, lower alkylamino having 1-6 carbon atoms, trifluoromethyl and halogen,

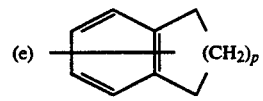

wherein p is an integer between 1 and 3, or

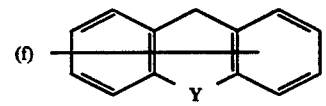

wherein Y is $CH_2$, O, S, $CH_2$—$CH_2$, CH=CH, $CH_2$—O Or $CH_2$—S;

$R^6$ represent hydrogen, lower alkyl having 1-6 carbon atoms, lower alkoxy having 1-6 carbon atoms or halogen;

X represents O or $S(O)_q$, wherein q is an integer having a value of 0, 1 or 2; and n represents an integer 1-6, or a pharmaceutically acceptable inorganic acid addition salt, organic acid addition salt, base addition salt or metal salt of said indole derivative compound.

2. A compound according to claim 1, wherein $R^5$ is —$CHR^7R^8$.

3. A compound according to claim 2 wherein $R^7$ and $R^8$ are aryl which is phenyl which is substituted with 1-3 substituents, which substituents are independently selected from the group consisting of lower alkyl having 1-6 carbon atoms, hydroxy, lower alkoxy having 1-6 carbon atoms, lower alkylamino having 1-6 carbon atoms, trifluoromethyl and halogen.

4. A compound according to claim 3 wherein said substituent of phenyl is fluorine.

5. A compound according to claim 4, wherein $R^1$, $R^2$ and $R^3$ are hydrogen, and $R^4$ is lower alkyl having 1-6 carbon atoms.

6. A compound according to claim 2, wherein $R^7$ and $R^8$ are alkyl having 1-10 carbon atoms.

7. A compound according to claim 6 wherein $R^1$, $R^2$ and $R^3$ are hydrogen, and $R^4$ is lower alkyl having 1-6 carbon atoms.

8. A compound according to claim 1, which is selected from the group consisting of 4-{2-[3-[1-(4,4'-difluorobenzhydryl)indol-5-yl]isocrotonylamino]-phenoxy}butyric acid, 4-{2-[3-[1-(1-propylbutyl)indol-5-yl]-cis-2-pentanoylamino]phenoxy}butyric acid and 4-{2-[3-[1-(4,4'-difluorobenzhydryl)indol-5-yl]-cis-2-pentenoylamino]phenoxy}butyric acid.

9. A pharmaceutical composition comprising a pharmaceutical carrier, and, as an active ingredient, an effective amount of the compound according to claim 1.

* * * * *